United States Patent [19]

Nishiyama et al.

[11] Patent Number: 5,514,773
[45] Date of Patent: May 7, 1996

[54] DEPSIPEPTIDE DERIVATIVES, PRODUCTION THEREOF AND USE THEREOF

[75] Inventors: Hitoshi Nishiyama, Neyagawa; Masaru Ohgaki, Kobe; Ryo Yamanishi, Ibaraki; Toshihiko Hara, Miura, all of Japan

[73] Assignee: Fujisawa Pharmaceutical Co., Ltd., Osaka, Japan

[21] Appl. No.: 295,782

[22] PCT Filed: Mar. 8, 1993

[86] PCT No.: PCT/JP93/00286

§ 371 Date: Sep. 12, 1994

§ 102(e) Date: Sep. 12, 1994

[87] PCT Pub. No.: WO93/19053

PCT Pub. Date: Sep. 30, 1993

[30] Foreign Application Priority Data

Mar. 17, 1992 [JP] Japan ..................... 4-092070
Oct. 15, 1992 [JP] Japan ..................... 4-305093

[51] Int. Cl.$^6$ .................. A61K 38/12; A61K 38/15; C07K 11/02
[52] U.S. Cl. ............................. 530/317; 530/323
[58] Field of Search ............... 514/11, 18; 530/323, 530/317; 930/30

[56] References Cited

U.S. PATENT DOCUMENTS 5,116,815  5/1992  Takagi et al. .................. 514/11

FOREIGN PATENT DOCUMENTS 503538  9/1992  European Pat. Off. .
35796    2/1991  Japan .

*Primary Examiner*—Jeffrey E. Russel
*Attorney, Agent, or Firm*—Oblon, Spivak, McClelland, Maier & Neustadt

[57] ABSTRACT

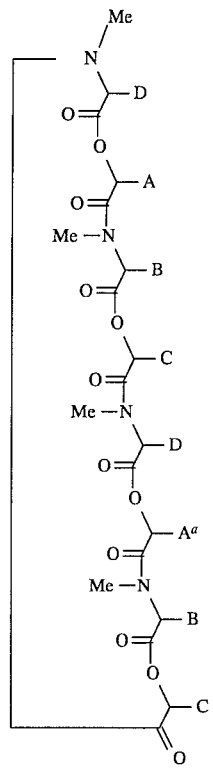

wherein

A is benzyl group which has suitable substituent(s) or phenyl group which may have suitable substituent(s), $A^a$ is benzyl group which may have suitable substituent(s) or phenyl group which may have suitable substituent(s), B and D are each lower alkyl, C is hydrogen or lower alkyl, and a pharmaceutically acceptable salt thereof. The compound or a salt thereof of the present invention has excellent parasiticidal activities as an anthelmintic agent for animals and human bodies.

12 Claims, No Drawings

DEPSIPEPTIDE DERIVATIVES, PRODUCTION THEREOF AND USE THEREOF

TECHNICAL FIELD

The present invention relates to new depsipeptide derivatives having antiparasitic activity.

BACKGROUND ART

Japanese Kokai Tokkyo Koho 3-35796 discloses depsipeptide derivative prepared by culturing microorganisms.

DISCLOSURE OF INVENTION

The object compound of the present invention, depsipeptide derivatives can be represented by the following general formula (I).

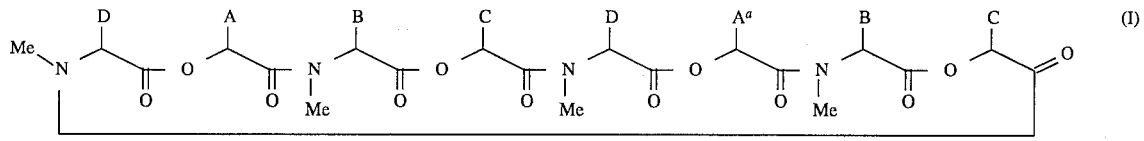

wherein
- A is benzyl group which has suitable substituent(s) or phenyl group which may have suitable substituent(s),
- $A^a$ is benzyl group which may have suitable substituent(s) or phenyl group which may have suitable substituent(s),
- B and D are each lower alkyl,
- C is hydrogen or lower alkyl.

According to the present invention, the object compound of depsipeptide derivatives (I) can be prepared by processes which are illustrated in the following schemes.

It should be indicated that any of D-configured compound, L-configured compound and/or DL-configured compound are in the extent of the present invention; however, for the convenience, only D-configured compounds and L-configured compounds are explained in the process for preparation as follows.

Process 1

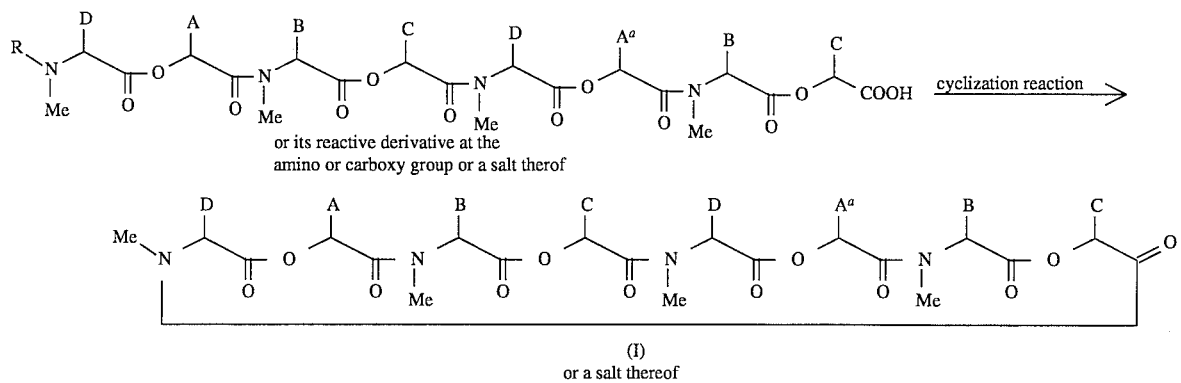

5,514,773
-continued
Process 2
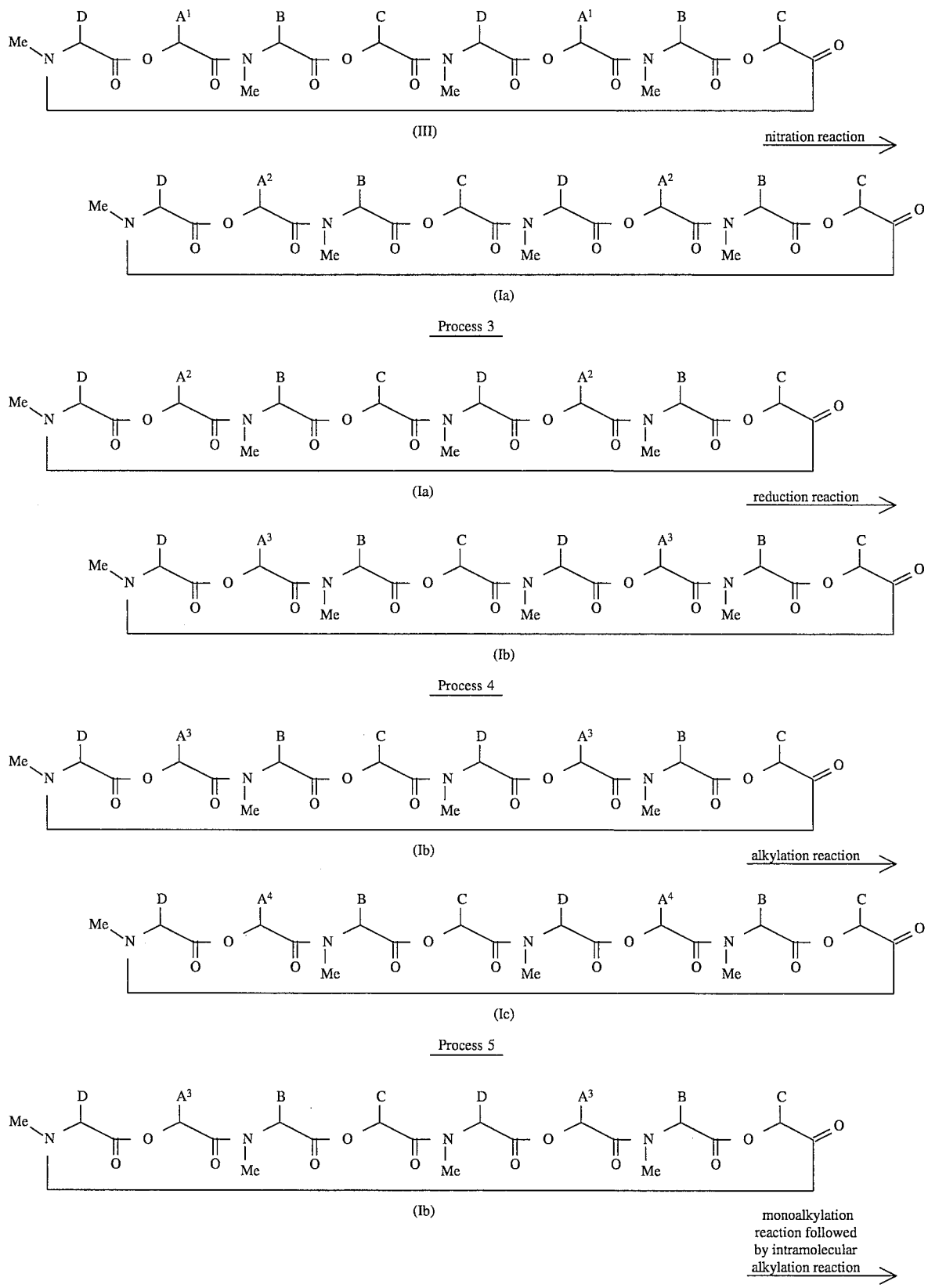

-continued

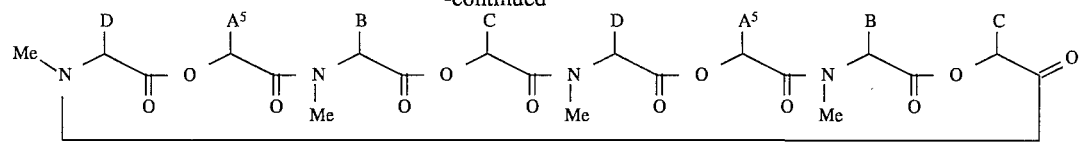

(Id)

Process 6

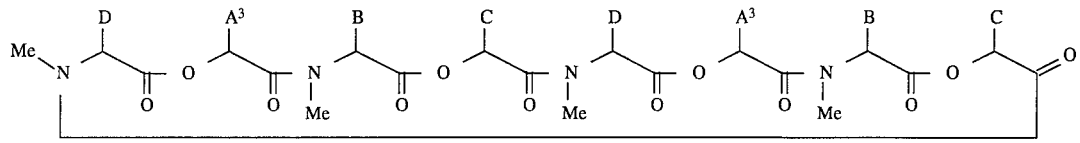

(Ib)

hydroxylation reaction via diazo compound →

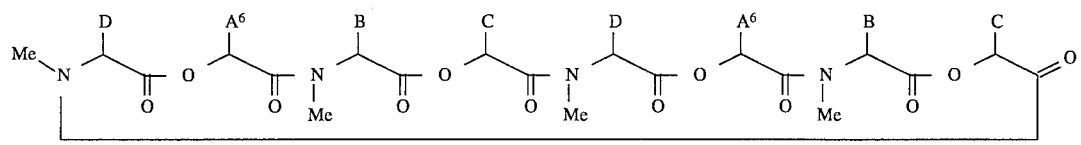

(Ie)

Process 7

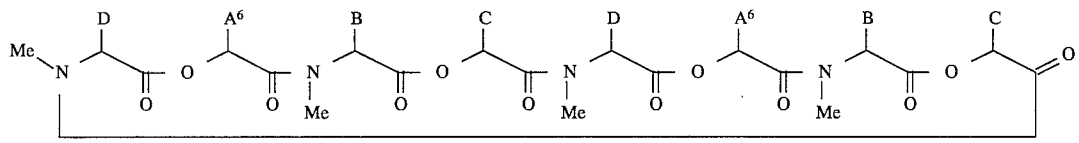

(Ie)

alkylation reaction →

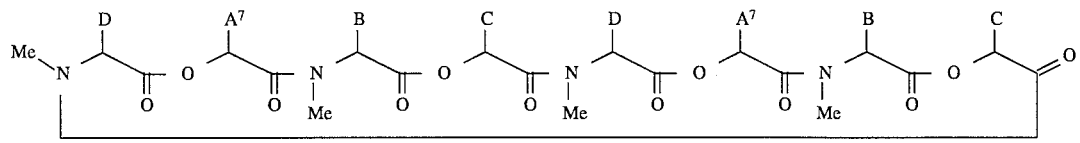

(If)

wherein

A, $A^a$, B, C and D are each as defined above,

R is hydrogen or amino protective group, $A^1$ is benzyl group which may have lower alkoxy, $A^2$ is benzyl group which has nitro, or benzyl group which has nitro and lower alkoxy, $A^3$ is benzyl group which has amino, or benzyl group which has amino and lower alkoxy, $A^4$ is benzyl group which has mono- or di-lower alkylamino, or benzyl group which has mono- or di-lower alkylamino and lower alkoxy, $A^5$ is benzyl group which has cyclic amino, or benzyl group which has cyclic amino and lower alkoxy, $A^6$ is benzyl group which has hydroxy, or benzyl group which has hydroxy and lower alkoxy, $A^7$ is benzyl group which has lower alkoxy.

Throughout the present specification, the amino acid, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues, and when shown by D- abbreviations, they are meant to be D-configured compounds and residues.

In the present invention, there are employed the following abbreviations.

p-MeOPhLac: 2-hydroxy-3-(4-methoxyphenyl) propionic acid [β-(p-methoxyphenyl)lactic acid]

Man: 2-hydroxyphenylacetic acid [mandelic acid]

p-Me$_2$NPhLac: 3-(4-dimethylaminophenyl)-2-hydroxypropionic acid [β-(p-dimethylaminophenyl)lactic acid]

p-PipPhLac: 2-hydroxy-3-(4-piperazinophenyl)propionic acid [β-(p-piperazinophenyl)lactic acid]

p-PyrPhLac: 2-hydroxy-3-(4-pyrrolidinophenyl)propionic acid [β-(p-pyrrolidinophenyl)lactic acid p-NO$_2$PhLac: 3-(4-nitrophenyl)-2-hydroxypropionic acid [β-(p-nitrophenyl)lactic acid]

p-NH$_2$PhLac: 3-(4-aminophenyl)-2-hydroxypropionic acid [β-(p-aminophenyl)lactic acid]

p-Et$_2$NPhLac: 3-(4-diethylaminophenyl)-2-hydroxypropionic acid [β-(p-diethylaminophenyl)lactic acid]

p-Hex$_2$NPhLac: 3-(4-di-n-hexylaminophenyl)-2-hydroxypropionic acid [β-(p-di-n-hexylaminophenyl)lactic acid]

p-PylPhLac: 2-hydroxy-3-(1H-pyrrol-1-yl-phenyl)propionic acid [β-(p-1H-pyrrol-1-yl)phenyl)lactic acid]

p-OHPhLac: 2-hydroxy-3-(4-hydroxyphenyl)propionic acid [β-(p-hydroxyphenyl)lactic acid]

p-EtOPhLac: 3-(4-ethoxyphenyl)2-hydroxypropionic acid [β-(p-ethoxyphenyl)lactic acid]

p-HexOPhLac: 3-(4-n-hexyloxyphenyl)-2-hydroxypropionic acid [β-(p-n-hexyloxyphenyl)lactic acid]

p-MEPhLac: 2-hydroxy-3-[4-(2-methoxyethoxy)phenyl]propionic acid [β-[p-(2-methoxyethoxy)phenyl]lactic acid]

p-MEEPhLac: 2-hydroxy-3-{4-[2-(2-methoxyethoxy)ethoxy]phenyl}propionic acid [β-{p-[2-(2-methoxyethoxy)ethoxy]phenyl}lactic acid]

o-MeOPhLac: 2-hydroxy-3-(2-methoxyphenyl)propionic acid [β-(o-methoxyphenyl)lactic acid]

m-MeOPhLac: 2-hydroxy-3-(3-methoxyphenyl)propionic acid [β-(m-methoxyphenyl)lactic acid]

3,4-DMOPhLac: 3-(3,4-dimethoxyphenyl)-2-hydroxypropionic acid [β-(3,4-dimethoxyphenyl)lactic acid]

2,4-DMOPhLac: 3-(2,4-dimethoxyphenyl)-2-hydroxypropionic acid [β-(2,4-dimethoxyphenyl)lactic acid]

3,4-MODPhLac: 2-hydroxy-3-(3,4-methylenedioxyphenyl)propionic acid [β-(3,4-methylenedioxyphenyl)lactic acid]

3-MA-4-MOPhLac: 3-(3-dimethylamino-4-methoxyphenyl)-2-hydroxypropionic acid [β-(3-dimethylamino-4-methoxyphenyl)lactic acid]

3,4-DMAPhLac: 3-[(3,4-bis(dimethylamino)phenyl]-2-hydroxyphenyl]propionic acid [β-[3,4-bis(dimethylamino)phenyl]]lactic acid]

o-FPhLac: 3-(2-fluorophenyl)-2-hydroxypropionic acid [β-(o-fluorophenyl)lactic acid]

m-FPhLac: 3-(3-fluorophenyl)-2-hydroxypropionic acid [β-(m-fluorophenyl)lactic acid]

p-FPhLac: 3-(4-fluorophenyl)-2-hydroxypropionic acid [β-(p-fluorophenyl)lactic acid]

Glycol: Glycolic acid

PhLac: 2-hydroxy-3-phenylpropionic acid [β-phenyllactic acid]

Lac: 2-hydroxypropionic acid [lactic acid]

p-MorPhLac: 2-hydroxy-3-(4-morpholinophenyl)propionic acid [β-(p-morpholinophenyl)lactic acid]

Suitable salts of the compound (I) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkali earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), preferably 1 to 4 carbon atom(s), unless otherwise indicated.

Suitable substituent(s) in the term "benzyl group which has substituent(s)", "phenyl group which may have substituent(s)" and "benzyl group which may have substituent(s)" may include hydroxy, lower alkoxy, lower alkoxy lower alkoxy, lower alkoxy lower alkoxy lower alkoxy, halogen, lower alkyl, amino, cyclic amino, nitro, halogen (e.g. fluoro, chloro, bromo, iodo, etc.) and the like. These may have 1 or more than 2 substituents.

Suitable "lower alkyl" may include straight or branched one having 1 to 6 carbon atom(s) such as methyl, ethyl, n-propyl, isopropyl, butyl, isobutyl, tert-butyl, pentyl, hexyl, and the like.

Suitable "lower alkoxy" may include methoxy, ethoxy, propoxy, isopropoxy, butoxy, isobutoxy, pentyloxy, isopentyloxy, hexyloxy, and the like.

Suitable "lower alkoxy lower alkoxy" may include methoxymethoxy, methoxyethoxy, methoxypropoxy, ethoxyisopropoxy, and the like.

Suitable "lower alkoxy lower alkoxy lower alkoxy" may include methoxymethoxyethoxy, methoxyethoxyethoxy, methoxyethoxypropoxy, ethoxymethoxyisopropoxy, and the like.

Suitable "cyclic amino group" may be aromatic ring or alicyclic compound which have more than 1 nitrogen atom(s) as hetero atom(s), and it containing monocyclic group or condensed polycyclic group which may be saturated or unsaturated. Also, cyclic amino group may further contain hetero atom(s) such as more than 1 or 2 nitrogen atom(s), oxygen atom(s), sulfur atom(s), and the like and still further the cyclic amino group may be spiro ring or bridged cyclic compound. The number of the constructive atom(s) of cyclic amino group are not limited, but for example, monocyclic group have 3 to 8-membered rings and bicyclic have 7 to 11-membered rings.

Example of such cyclic amino group may include saturated or unsaturated monocyclic group which contain one nitrogen atom as hetero atom(s) such as 1-azetidinyl, pyrrolidino, 2-pyrroline-1-yl, 1-pyrrolyl, piperidino, 1,4-dihydropyrizine-1-yl, 1,2,5,6-tetrahydropyrizine-1-yl, homopiperidino and the like, saturated or unsaturated monocyclic group which contain more than two nitrogen atom(s) as hetero atom(s) such as 1-imidazolidinyl, 1-imidazolyl, 1-pyrazolyl, 1-triazolyl, 1-tetrazolyl, 1-piperazinyl, 1-homopiperazinyl, 1,2-dihydropyridazine-1-yl, 1,2-dihydropyrimidine-1-yl, perhydropyrimidine-1-yl, 1,4-diazacyclo heptane-1-yl, saturated or unsaturated monocyclic group which contain 1 to 2 oxygen atom(s) and 1 to 3 nitrogen atom(s) as hetero atom(s) such as oxazolidine-3-yl, 2,3-dihydroisooxazole-2-yl, morpholino, saturated or unsaturated monocyclic group which contain 1 to 2 sulfur atom(s) and 1 to 3 nitrogen atom(s) as hetero atom(s) such as thiazolidine-3-yl, isothiazoline-2-yl, thiomorpholino, condensed polycyclic group such as indole-1-yl, 1,2-dihydrobenzimidazole-1-yl, perhydropyrrolo[1,2-a]pyrazine-2-yl, spirocyclic group such as 2-azaspiro[4,5]decane-2-yl, bridged cyclic heterocyclic group such as 7-azabicyclo[2,2,1]heptane-7-yl, and the like.

Said lower alkoxy, lower alkyl, amino, cyclic amino group and the like may have suitable substutuent(s), such as lower alkylamino which is mono- or di-substituted, lower alkenyl, aralkyl, aryl, hydroxy, hydroxy lower alkyl, nitro, cyano, above mentioned cyclic amino, above mentioned lower alkoxy, lower alkoxy lower alkyl, halogen, halo lower alkyl, amino, protected amino, amino lower alkyl, protected amino lower alky, cyclo lower alkylamino, and the like.

The numbers of these substituent(s) are not limited, preferably 1 to 4, and the substituent(s) may be the same or not the same. Also two of the same or not the same substituent(s) may substitute the same atom(s) on cyclic amino group.

"Mono- or di-lower alkylamino group" may include amino group which has the group of one or two lower alkyl (e.g. methyl, ethyl, isopropyl, tert-butyl, tert-pentyl, etc. ), preferably methylamino, ethylamino, dimethylamino, diethylamino, di-n-propylamino, diisopropylamino, dibutylamino, etc.

"Lower alkenyl group" may include vinyl, allyl, isopropenyl, and the like. "Aralkyl group" may include benzyl, 1-phenylethyl, and the like.

"Aryl group" may include phenyl, naphthyl, and the like.

"Hydroxy lower alkyl group, alkoxy lower alkyl group, halo lower alkyl group, amino lower alkyl group, protected amino lower alkyl group" means that optional carbon atom(s) of above mentioned lower alkyl has each hydroxy, alkoxy, halogen, amino, protected amino.

"Amino protecting group", may include acyl such as lower alkanoyl (e.g. formyl, acetyl, propionyl, pivaloyl, hexanoyl, etc.), mono- (or di- or tri-) halo (lower) alkanoyl group (e.g. chloroacetyl, bromoacetyl, dichloroacetyl, trifluoroacetyl, etc.), lower alkoxycarbonyl group, (e.g. methoxycarbonyl, ethoxycarbonyl, propoxycarbonyl, tert-butoxycarbonyl, tert-pentyloxycarbonyl, hexyloxycarbonyl, etc.), carbamoyl group, aroyl group (e.g. benzoyl, toluoyl, naphthoyl, etc.), ar (lower) alkanoyl group (e.g. phenylacetyl, phenylpropionyl, etc.), aryloxycarbonyl group (e.g. phenoxycarbonyl, naphthyloxycarbonyl, etc.), aryloxy (lower) alkanoyl group (e.g. phenoxyacetyl, phenoxypropionyl, etc.), arylglyoxyloyl group, (e.g. phenylglyoxyloyl, naphthylglyoxyloyl, etc.), ar (lower) alkoxycarbonyl group which may have suitable substituent(s), (e.g. benzyloxycarbonyl, phenethyloxycarbonyl, p-nitrobenzyloxycarbonyl, etc.), ar (lower) alkylidene group which are substituted or not substituted (e.g. benzylidene, hydroxybenzylidene etc.), ar (lower)alkyl group such as mono- (or di- or tri-) phenyl (lower) alkyl (e.g. benzyl, phenethyl, benzhydryl, trityl, etc.) and the like.

Above mentioned amino protective group contain the protective group which have the function to temporarily protect amino group which is often used in the field of amino acid and peptide chemistry.

Suitable "benzyl group which has lower alkoxy" may include lower alkoxy substituted benzyl such as 4-methoxybenzyl, 2,4-dimethoxybenzyl, 3,4-dimethoxybenzyl, 3,4,5-trimethoxybenzyl, 2,3,4-trimethoxybenzyl, 2-ethoxybenzyl, 4-hexyloxybenzyl, etc.

Suitable "benzyl group which has halogen" may include halogen substituted benzyl such as 2-fluorobenzyl, 3-fluorobenzyl, 4-fluorobenzyl, 2-chlorobenzyl, 4-chlorobenzyl, 2,4-dichlorobenzyl, 3,4-dichlorobenzyl, 2,6-dichlorobenzyl, 2-bromobenzyl, 2-bromo-4-chlorobenzyl, etc.

Suitable "benzyl group which has lower alkyl" may include lower alkyl substituted benzyl such as 4-methylbenzyl, 4-ethylbenzyl, 4-propylbenzyl, 4-isopropylbenzyl, 4-butylbenzyl, 4-isobutylbenzyl, 4-tert-butylbenzyl, 4-pentylbenzyl, 4-hexylbenzyl, 2,3-dimethylbenzyl, 2,6-dimethylbenzyl, 3,4-dimethylbenzyl, 2,4,6-trimethylbenzyl, etc.

Suitable example of phenyl group which have such substituent(s) may include lower alkoxy substituted phenyl group (e.g. 4-methoxyphenyl, 3,4-dimethoxyphenyl, 3,4,5-trimethoxyphenyl, 2,3,4-trimethoxyphenyl, 2-ethoxyphenyl, 4-hexyloxyphenyl, etc.), halogen substituted phenyl (e.g. 2-chlorophenyl, 4-chlorophenyl, 2,4-dichlorophenyl, 3,4-dichlorophenyl, 2,6-dichlorophenyl, 2-bromophenyl, 2-bromo-4-chlorophenyl, 4-fluorophenyl, 2,4-difluorophenyl etc.), hydroxy substituted phenyl (e.g. 2-hydroxyphenyl, 3-hydroxyphenyl, 4-hydroxyphenyl, etc.), lower alkoxy- and hydroxy-substituted phenyl (e.g. 2-(hydroxymethoxy) phenyl, etc.).

Suitable example of benzyl group which have such substituent(s) may include lower alkoxy substituted benzyl (e.g. 4-methoxybenzyl, 3,4-dimethoxybenzyl, 3,4,5-trimethoxybenzyl, 2,3,4-trimethoxybenzyl, 2-ethoxybenzyl, 4-hexyloxybenzyl, etc.), halogen substituted benzyl (e.g. 2-chlorobenzyl, 4-chlorobenzyl, 2,4-dichlorobenzyl, 3,4-dichlorobenzyl, 2,6-dichlorobenzyl, 2bromobenzyl, 2-bromo-4-chlorobenzyl, etc.), hydroxy substituted benzyl (e.g. 2-hydroxybenzyl, 3-hydroxybenzyl, 4-hydroxybenzyl, etc.), lower alkoxy and hydroxy substituted benzyl (e.g. 2-(hydroxymethoxy) benzyl, etc.)

More preferable example of "cyclic amino group which may have substituent(s)" may include pyrrolidino, morpholino, 1-piperazino, 4-methylpiperazino, piperidino and the like.

The processes for preparing the object compound (I) are explained in detail in the following.

Process 1

The object compound (I) or a salt thereof can be prepared by subjecting the compound (II) or its reactive derivative at the amino group or carboxy group or a salt thereof to cyclization reaction.

The starting compound (II), its reactive derivative or a salt thereof is new and such compounds can be prepared by the methods described in Preparation mentioned below or in substantially the same manner.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide, bis(trimethylsilyl)urea or the like; a derivative formed by reaction of the compound (II) with phosphorus trichloride or phosgene, and the like.

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride within acid such as a aliphatic carboxylic acid [e.g. acetic acid, propionic acid, burytic acid, trichloroacetic acid, etc.] or aromatic carboxylic acid [e.g. benzoic acid, etc.]; a symmetrical acid anhydride, and the like. These reactive derivatives can optionally be selected from them according to the kind of the compound (II) to be used. The reaction is usually carried out in the usual method which is used in cyclization reaction, under heating or in the presence of a conventional condensing agent. When R in the compound (II) is amino protective group, the elimination of the amino protective group is carried out previous to ring cyclization reaction.

Suitable condensing agent may include carbodiimide or a salt thereof [e.g. N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide or hydrochloride thereof, diphenyl phosphoryl azide, diethyl phosphorocyanidate, bis(2-oxo-3-oxazolidinyl)phosphinic chloride, etc.]; N,N'-carbonyldiimidazole, N,N'-carbonylbis-(2-methylimidazole); keteneimine compound(e.g. pentamethyleneketene-N-cyclohexylimine; diphenylketene-N-cyclohexylimine; ethoxyacetylene; 1-alkoxy-1-chloroethylen; ethyl polyphosphate; isopropyl polyphosphate; phosphorus oxychloride; phosphorus trichloride; thionyl chloride; oxalyl chloride; combining triphenylphosphine, and carbon tetrachloride or siazen carboxylate; 2-ethyl-7-hydroxybenzisoxazolium salt;

2-ethyl-5-(m-sulfophenyl)isoxazolium hydroxide intramolecular salt; 1-(p-chlorobenzenesulfonyloxy)-6-chloro-1H-benzotriazole; 1-hydroxybenzotriazol; so-called Vilsmeier reagent prepared by the reaction of N,N-dimethylformamide with thionyl chloride, phosgene, trichloromethyl chloroformate, phosphorus oxychloride, etc.; or the like.

The reaction in the presence of conventional condensing agent may be carried out in an organic solvent such as dichloromethane, methanol, ethanol, propanol, acetonitrile, pyridine, N,N-diethylformamide, 4-methyl-2-pentanone, tetrahydrofuran, benzene, toluene, xylene, etc. or any other solvent mixture which does not adversely influence the reaction.

The reaction temperature is not critical and the reaction is usually carried out under cooling to heating. Further, ring cyclization reaction under heating can be carried out to heat under boiling point in the solvent which is used in an organic solvent as above.

Process 2

The compound (Ia) or a salt thereof can be prepared by subjecting the compound (III) or a salt thereof to nitration reaction.

The starting compounds (III) contain known compounds (Japanese Kokai Tokkyo Koho No. 3-35796) and novel compounds. The novel compounds can be prepared by the procedures described in Preparations and Examples mentioned later or in substantially the same manner.

This reaction is carried out by reacting the compound (III) or a salt thereof with nitration agent (e.g. nitric acid, etc.).

The reaction can usually be carried out in a conventional solvent such as dichloromethane which does not adversely influence the reaction.

The reaction temperature is not critical and the reaction is usually carried out under cooling to heating.

This reaction can be carried out in substantially the same manner as Example 7 mentioned later.

Process 3

The object compound (Ib) or a salt thereof can be prepared by subjecting the compound (Ia) or a salt thereof to the reduction reaction.

This reaction can be carried out in a conventional manner for reducing: nitro to amino, and it may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.]. palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 4

The object compound (Ic) or a salt thereof can be prepared by subjecting the isolated or not isolated the compound (Ib) or a salt thereof, which is obtained by the Process 3, to alkylation reaction. This reaction can be carried out by combining aldehyde and reduction agent or alkylhalide and base. Suitable reduction agents are metallic hydride complex compound, [e.g. sodium borohydride, sodium cyanoborohydride, potassium borohydride, bis(2-methoxyethoxy) aluminium hydride, etc.], a combination of hydrogen, formic acid, or ammonium formate, and palladium catalysts [e.g. palladium on carbon, palladium hydroxide on carbon, palladium black, etc.].

Suitable base may include an inorganic base such as sodium bicarbonate, potassium carbonate, etc., or an organic base such as pyridine, triethylamine, etc. The reaction is usually carried out in a conventional solvent which does not adversely influence the reaction. The reaction which is combined by aldehyde and reduction agents can be carried out in substantially the same manner as Preparation 23 or Example 8 mentioned later, and the reaction which is combined by an alkyl halide and a base can be carried out in substantially the same manner as Preparation 41 mentioned later.

The reaction which is combined by the compound containing two aldehydes and reduction agents can be carried out in substantially the same manner as Example 31 mentioned later.

Process 5

The object compound (Id) or a salt thereof can be prepared by subjecting the isolated or not isolated compound (Ib) or a salt thereof, which is obtained by the Process 3, to mono alkylation reaction followed by intramolecular alkylation reaction. The reaction can be carried out by combining a compound, which has two aldehydes in the molecule, and reduction agents or by combining a compound, which has two halogens and a base.

Process 6

The object compound (Ie) or a salt thereof can be prepared by subjecting the isolated or not isolated object compound (Ib) or a salt thereof, which is obtained by the Process 3, to hydroxylation reaction by diazotization reaction followed by decomposition of diazonium salt. This reaction can be carried out by reacting the compound (Ib) or a salt thereof with sodium nitrite in the presence of an inorganic or an organic acid and decomposing a growing diazonium salt in water or an organic acid under the room temperature to heating, carrying out hydrolysis if necessary. It is possible to prepare the compound (Ie) or a salt thereof by transforming the amino group of the compound (Ib) or a salt thereof into a hydroxyl group. Suitable acid may include an inorganic acid [e.g. sulfuric acid, hydrochloric acid, borofluoric acid, etc.], and an organic acid [e.g. acetic acid, trifluoroacetic acid, etc.].

Process 7

The object compound (If) or a salt thereof can be prepared by subjecting the compound (Ie) or a salt, which is obtained by the Process 6, thereof to alkylation reaction. This reaction can be prepared by combining a alkylhalide and a base.

The reaction can be carried out substantially in the same manner as the later mentioned Example 15 and Example 16.

Suitable base may include an inorganic base [e.g. sodium bicarbonate, potassium carbonate, etc. and an organic base [e.g. pyridine, triethylamine, etc.].

The compound or its salt of the present invention has excellent parasiticidal activities as an anthelmintic agent for animals and human bodies. It is effective to nematodes which are infected particularly to the domestic animals, domestic fowls or pets such as pigs, sheep, goats, cattle, horses, dogs, cats, and chickens.

Haemonchus genus, Trichostrongylus genus, Ostertagia genus, Nematodirus genus, Cooperia genus, Ascaris genus, Bunostomum genus, Oesophagostomum genus, Chabertia genus, Trichuris genus, Strongylus genus, Trichonema genus, Dictyocaulus genus, Capillaria genus, Heterakis genus, Toxocara genus, Ascaridia genus, Oxyuris genus, Ancylostoma genus, Uncinaria genus, Toxascaris genus, Parascaris genus, Nippostrongylus genus, Metastrongylus genus, Hyostrongylus genus, Strongyloides genus, Cyathostomum genus.

The parasiticidal activities are pointed out in some kind of Nematodirus genus, Cooperia genus, and Oesophagostomum genus which attack the intestinal tract, however, just Haemonchus genus and Ostertagia genus are parasitic on the stomach, and parasites of Dictyocaulus genus are found in lungs.

The parasites of Filariidae or Setariidae activities are found in heart and blood vessels, hypodermis, or lymphatic vessel or any other organisms or organs.

It is also effective to parasites which infect human beings. The most common parasites in the alimentary canal of human beings are as follows:

Ancylostoma genus, Necator genus, Ascaris genus, Strongyloides genus, Tichinell genus, Capillaria genus, Trichuris genus, and Enterobius genus.

It is also active for other medically important parasites, which is found in the blood or other organisms or organs out side of the alimentary canal, such as Wuchereria genus, Brugia genus, Onchocerca genus and Loa genus in Filariidae, as well as parasites such as Dracunlus genus in Dracunculidae. It is also active for parasites such as Strongyloides genus and Trichinella genus in the intestinal tract in a particular conditioned parasitism out side of intestinal tract.

Test

Test 1
(1) Test Compounds
The compounds which are illustrated in Example 1, Example 3, Example 4, Example 5, Example 10, Example 17, Example 23, Example 24, Example 25, and Example 29.
(2) Test
The effect of parasiticides was examined with the rats which was infected by nematodes which are parasitic on rats, *Nippostrongylus brasilienses*.

Wistar strain rats (female 6 weeks old, 120–130 g weight) were sacrificed by infecting them and giving them subcutaneous injections of 3000 infective larvae per rat.

Test compound of 50 mg was dissolved in 0.25 ml dimethylsulfoxide, 0.5% methylcellulose solution was added, and liquid volume was adjusted to be prescribed volume of 100, 10, 5, 2.5, 1.25, 1.0, 0.63, 0.32 mg/kg to utilize. After they were infected, on each 7th, 8th, and 9th day, the test compound was administered orally with above concentration. On the 11th day, the rat was dissected and the numbers of parasites in the small intestines were measured.

The given measurement was based to calculate the reduction rate from the percentage of the numbers of the parasites of unadministered rats (control). The result of it is shown in the
Test 2
The reduction rate was calculated in a similar manner as Test 1 except when the test compound was subcutaneously administered to the rats instead of oral administration as in Test 1. The result of that is shown in the Table 2.
Test 3
For 1 rat, the 5000 infective larvae of *Strongyloides venezuelensis* were infected percutaneously to one group (2 rats) of 8 weeks old Mongolian gerbils. On the 10th day after they were infected, the suspended test compound was orally administered once with the amount of established administration. The effect was judged according to the amount of the eggs in the feces or the numbers of worms in the intestinal tract. The measurement of the numbers of the eggs were taken from O ring method, and the numbers of the eggs (EPG) in 1 g of feces were counted on the day before, on the day, and on the 1st, 2nd, 3rd, and 4th day after the administration. The numbers of the parasites were measured by dissecting Mongolian gerbils the 4th day after the administration (on the 14th day after infection). The method of measurement was followed by releasing the parasites, which live in the small intestines, into saline solution over night, and the released parasites were set to be as numbers of worms recovered.

The result (the mean number of each group) is shown in the Table 3.
Test Results

TABLE 1

| Test Compounds | Minimum Amount of Administration indicated by more than 95% of Reduction Rate |
| --- | --- |
| PF1022 (Japanese Patent Application 3 - 35796) | 10 mg/kg |
| Example - 1 | 2.5 mg/kg |
| Example - 3 | 1.25 mg/kg |
| Example - 4 | 2.5 mg/kg |
| Example - 5 | 0.63 mg/kg |
| Example - 10 | 2.5 mg/kg |
| Example - 17 | 2.5 mg/kg |
| Example - 23 | 5 mg/kg |
| Example - 24 | 5 mg/kg |
| Example - 25 | 5 mg/kg |
| Example - 29 | 5 mg/kg |

TABLE 2

| Test Compounds | Minimum Amount of Administration indicated by more than 95% of Reduction Rate |
| --- | --- |
| PF1022 (Japanese Patent Application 3 - 35796) | >100 mg/kg |
| Example - 1 | 10 mg/kg |
| Example - 3 | 5 mg/kg |
| Example - 5 | 1.25 mg/kg |
| Example - 12 | 50 mg/kg |

TABLE 3

| Test Compounds | Dose | Change in Numbers of Parasites' Number of Eggs in Feces (EPG/100) | | | | | | Numbers of the Worms recovered |
|---|---|---|---|---|---|---|---|---|
| | | −2 | 0* | 1 | 2 | 3 | 4 | |
| Unadministered control | — | 574 | 1240 | 1725 | 2343 | 1533 | 1505 | 3005 |
| PF1022 | 20 mg/kg | 332 | 1615 | 581 | 1563 | 935 | 1005 | 3088 |
| Example - 5 | 5 mg/kg | 455 | 1890 | 701 | 0 | 0 | 0 | 0 |
| Example - 5 | 2.5 mg/kg | 838 | 1665 | 452 | 0 | 0 | 0 | 0 |
| Example - 5 | 1.25 mg/kg | 551 | 2800 | 536 | 0 | 0 | 30 | 8 |

*stands for the starting day of administration.

When the compound of the present invention are used for animals and human being as an anthelmintic agent, it can be administered orally as a liquid drink. The liquid drink is usually suspended agent such as bentonite, and wetting agent, or other excipients with non-toxic solution, or solution made of water, suspension, or dispersed solution, and generally it comprises liquid drinks or antifoaming agent. The prescription of a liquid drink contains generally activated compound for 0.01–0.5 weight %, preferably 0.0–0.1 weight %. When it is preferably administered orally as a dried solid single dose, capsules, pills, or tablets, which comprise the desired amount of activated compounds are usually used. These forms of dosage are prepared by homogeneous admixtures of diluent, filler, disintegrator and/or excipient agents such as dextrine, lactose, talc, magnesium stearate, vegetable rubber, etc.

The usage of such single dose prescription can be varied broadly by kind of hosts, or kind of parasites, or weight of hosts which are to be treated and referring to the weight and containing quantity of anthelmintics.

When it is administered in animal feed, it is used as to disperse homogeneously, or as top dressing, or in the form of pellet. To achieve preferable effect of antiparasites, the activated compound of 0.0001–2% is usually contained in feed.

The dosage which was dissolved or dispersed in liquid carrier excipients can be administered to animals parenterally by giving them injections in the anterior stomach, muscle, tachea, or under the skin. The activated compound is mixed with suitable vegetable oil such as peanut oil or cottonseed oil for parenteral administration. These prescriptions generally contain the activated compound of 0.05–50 weight %. It can also be administered locally by mixing in a suitable carrier such as dimethylsulfoxide or hydrocarbon solvent. The prepared solvents can be used directly on the exterior of animals by sprays or direct injections.

The most suitable usage amount of the activated compound to achieve the most effective result depends on the kind of animals, which are to be treated, and type of parasital infection and its stage. It can be achieved by oral administration of the activated compound 0.01–100 mg, preferably 0.5–50.0 mg, per kg of the treated animal. Such dosage amount is given in a relatively short term of 1–5 days at once or separately.

The Preparations and Examples of the present invention are shown in the following.

Preparation 1

Boc-Tyr (Me)-OH (5.1 g), was dissolved in 4N-hydrogen chloride in dioxane (87.5 ml) and stirred under ice-cooling for 2 hours. After dioxane was evaporated in vacuo, the residue was dissolved in 6N-hydrochloric acid aqueous solution (45 ml) and at 0° C., sodium nitrite (1.9 g) was added by portions. After stirring for 4 hours, the reaction solution was extracted with ether (100 ml×3). After washing ether layer by saturated brine, the extract was dried over calcium chloride and the solvent was evaporated in vacuo. To the residue, benzene (30 ml), benzyl alcohol (3.4 ml) and p-toluenesulfonic acid mono hydrate (0.22 g) were added and heated under reflux for 3 hours by using Dean Stark apparatus. After cooling down to the room temperature, the crude product, which was gained by evaporating the solvent, was purified by silica gel chromatography (eluting with ethyl acetate: hexane=1:10, v/v). The fractions containing the desired product were combined and evaporated in vacuo to obtain benzyl (S)-2-chloro-3-(4-methoxyphenyl) propionate (1.79 g).

NMR (CDCl$_3$, δ): 3.12 (dd,1H), 3.29 (dd,1H), 3.78 (s,3H), 4.44 (t, 1H), 5.07–5.25 (m,2H), 6.77–7.36 (m,9H).

Preparation 2

To a solution of Boc-MeLeu-OH (1.37 g) in methanol (30 ml) and water (10 ml) was added 20% aqueous cesium carbonate solution to be pH7.0. After the solvent was evaporated in vacuo, azeotroped three times by toluene (10 ml). The residue was dissolved in dimethylformamide (20 ml), under ice-cooling, benzyl (S)-2-chloro-3-(4-methoxyphenyl) propionate (1.79) was added and stirred at room temperature for 24 hours. The reaction solution was poured into water (150 ml), extracted with ether (100 ml×3), washed with saturated brine, and dried over anhydrous magnesium sulfate. The solvent was evaporated in vacuo, the resultant crude product was purified by silica gel chromatography, and eluted with mixture of ethyl acetate and hexane (1:8, v/v). The fractions containing the desired product were combined and evaporated in vacuo to obtain Boc-MeLeu-D-p-MeOPhLac-OBzl (1.59 g).

NMR (CDCl$_3$,δ): 0.90 (d,6H), 1.41 (s) and 1.49 (s) (9H), 1.40–1.58 (m, 3H), 2.62–2.67 (m,3H), 3.06–3.15 (m,2H), 3.77 (s,3H), 4.68–4.80 (m) and, 4.97–5.29 (m) (4H), 6.78 (d,2H), 7.06 (d,2H), 7.26–7.36 (m,5H).

Preparation 3

To a solution of Boc-MeLeu-D-p-MeOPhLac-OBzl (1.36 g) in methanol (15 ml) was added 10% palladium on carbon (0.4 g), and hydrogenated at atmospheric pressure of hydrogen gas for 45 minutes at ambient temperature. The catalyst was filtered off, the solvent was evaporated to give Boc-MeLeu-D-p-MeOPhLac-OH (1.08 g).

NMR (CDCl$_3$,δ): 0.89–0.95 (m,6H), 1.44 (s,9H), 1.44–1.79 (m,3H), 2.66–2.82 (m,3H), 3.01–3.20 (m,2H), 3.79 (s,3H), 4.40–4.75 (m,1H), 5.15–5.38 (m,1H), 6.82 (d,2H), 7.14 (d,2H).

Preparation 4

Boc-MeLeu-D-Lac-OBzl (1.04 g) was dissolved in 4N-hydrogen chloride in dioxane (12.5 ml), under ice-cooling stirred for 3 hours. After the solvent was evaporated in vacuo, azeotroped twice by toluene (10 ml) to give H-MeLeu-D-Lac-OBzl.HCl (1g).

NMR (CDCl$_3$, δ): 0.94–1.00 (m,6H), 1.59 (d,3H), 1.78–2.13 (m,3H), 2.62–2.75 (m,3H), 3.78–3.85 (m,1H), 5.09–5.29 (m,3H), 7.25–7.43 (m,5H), 9.80–10.00 (m,1H), 10.30–10.55 (m,1H).

Preparation 5

To the mixture of Boc-MeLeu-D-pMeOPhLac-OH (1g), H-MeLeu-D-Lac-OBzl.HCl (1 g) in dichloromethane (20 ml) and triethylamine (15 ml) was added bis(2-oxo-3-oxazolidinyl) phosphinic chloride (0.98 g), and was stirred for 13 hours. The water (50 ml) was added to the mixture and it was extracted with ethyl acetate (50 ml×3). After it was washed with saturated brine, it was dried over anhydrous sodium sulfate. The solvent was evaporated in vacuo, the resultant crude product was purified by silica gel chromatography, and eluted with mixture of ethyl acetate and hexane (1:3, v/v). The fractions containing the desired product were combined and evaporated in vacuo to obtain Boc-MeLeu-D-p-MeOPhLac-MeLeu-D-Lac-OBzl (1.59 g).

NMR (CDCl$_3$,δ): 0.80–0.99 (m,12H), 1.42–1.80 (m,18H), 2.66–3.04 (m,8H), 3.78 (s,3H), 4.64–5.43 (m,6H), 6.81 (d,2H), 7.12–7.39 (m,7H).

Preparation 6

Boc-MeLeu-D-p-MeOPhLac-MeLeu-D-Lac-OBzl was used instead of Boc-MeLeu-D-p-MeOPhLac-OBzl. Except above matter, Boc-MeLeu-D-p-MeOPhLac-MeLeu-D-Lac-OH (0.67 g) was obtained according to a similar manner to that of Preparation 3.

NMR (CDCl$_3$,δ): 0.82–0.94 (m,12H), 1.46 (s,9H), 1.40–1.80 (m,9H), 2.67–3.29 (m,8H), 3.77 (s,3H), 4.83–5.71 (m,4H), 6.80 (d,2H), 7.15 (d,2H).

Preparation 7

Boc-MeLeu-D-p-MeOPhLac-MeLeu-D-Lac-OBzl (0.75 g) was dissolved in 4N-hydrogen chloride in ethyl acetate (5.25 ml), and it was stirred under ice-cooling for three hours. After the solvent was evaporated in vacuo, it was azeotroped twice by toluene (10 ml) to give H-MeLeu-D-p-MeOPhLac-MeLeu-D-Lac-OBzl.HCl (0.74 g).

NMR (CDCl$_3$,δ): 0.77–1.00 (m,12H), 1.21–1.98 (m,9H), 2.61–3.10 (m,8H), 3.77 (s,3H), 3.62–3.82 (m,1H), 5.04–5.55 (m,6H), 6.83 (d,2H). 7.12–7.34 (m,7H), 9.30–9.50 (m,1H), 10.40–10.59 (m,1H).

Preparation 8

Boc-MeLeu-D-p-MeOPhLac-MeLeu-D-Lac-OH (0.67 g) was used instead of Boc-MeLeu-D-p-MeOPhLac-OH. H-MeLeu-D-p-MeOPhLac-MeLeu-D-Lac-OBzl.HCl (0.74 g) was used instead of H-MeLeu-D-Lac-OBzl.HCl. Except above matter, Boc-MeLeu-D-p-MeOPhLac-MeLeu-D-Lac-MeLeu-D-p-MeOPhLac-MeLeu-D-Lac-OBzl (0.94 g) was obtained according to a similar manner to that of Preparation 5.

NMR (CDCl$_3$,δ): 0.80–0.99 (m,24H), 1.10–1.70 (m,2.7H), 2.65–3.10 (m,16H), 3.77 (s,6H), 4.61–5.49 (m,10H), 6.78–6.85 (m,4H), 7,12–7.40 (m,9H).

Preparation 9

Boc-MeLeu-D-p-MeOPhLac-MeLeu-D-Lac-MeLeu-D-p-MeOPhLac-MeLeu-D-Lac-OBzl (0.92 g) was used instead of Boc-MeLeu-D-p-MeOPhLac-OBzl. Except above matter, Boc-MeLeu-D-p-MeOPhLac-MeLeu-D-Lac-MeLeu-D-pMeOPhLac-MeLeu-D-Lac-OH (0.89 g) was obtained according to a similar manner to that of Preparation 3.

NMR (CDCl$_3$,δ): 0.79–0.99 (m,24H), 1.10–1.80 (m,2.7H), 2.65–3.10 (m,16H), 3.77 (s,6H), 4.60–5.65 (m,8H), 6.78–6.90 (m,4H), 7.13–7.25 (m,4H).

Preparation 10

To a solution of Boc-MeLeu-D-p-MeOPhLac-MeLeu-D-Lac-MeLeu-D-p-MeOPhLac-MeLeu-D-Lac-OH (0.89 g) and pentafluorophenol (0.14 g) in dichloromethane (10 ml) were added under ice-cooling, 1-ethyl-3-(3-dimethylaminopropyl) carbodiimide-hydrochloride (0.22 g), and stirred for 3 hours. The solvent was evaporated in vacuo, the resultant crude product was purified by silica gel chromatography, and eluted with mixture of ethyl acetate and hexane (1:1, v/v). The fractions containing the desired product were combined and evaporated in vacuo to obtain Boc-MeLeu-D-p-MeOPhLac-MeLeu-D-Lac-MeLeu-D-pMeOPhLac-MeLeu-D-Lac-OC$_6$F$_5$ (0.8 g).

NMR (CDCl$_3$,δ): 0.80–0.99 (m,24H), 1.10–1.80 (m,2.7H), 2.65–3.18 (m,16H), 3.77 (s,6H), 4.60–5.55 (m,8H), 6.78–6.90 (m,4H), 7.10–7.22 (m,4H).

Preparation 11

To a solution of H-D-Man-OH (1 g) and triethylamine (0.92 ml) in ethyl acetate (50 ml) was added phenacyl bromide (1.31 g) under ice-cooling. After the mixture was stirred for 48 hours at room temperature, the reaction mixture was poured into water and was extracted with ethyl acetate (50 ml×3). After the extract was dried over anhydrous magnesium sulfate, it was concentrated in vacuo to give H-D-Man-OPac (1.7 g).

NMR (CDCl$_3$,δ): 5.30 (d,1H), 5.41 (s,1H), 5.47 (d,1H), 7.31–7.88 (m,10H).

Preparation 12

To a solution of Boc-MeLeu-OH (1.54 g), and H-D-Man-OPac (1.7 g) in methylene chloride (50 ml) were added dimethylaminopyridine (77mg) and 1-ethyl-3-(3-dimethylaminopropyl) carbodiimide.hydrochloride (1.32 g) under ice-cooling, The mixture was stirred for 3 hours successively. After methylene chloride was evaporated in vacuo, ethyl acetate (200 ml) was added, and washed with water, the solution was dried over anhydrous magnesium sulfate. The solvent was evaporated in vacuo, the resultant crude product was purified by silica gel chromatography, and eluted with mixture of ethyl acetate and hexane (1:3, v/v). The fractions containing the desired product were combined and evaporated in vacuo to obtain Boc-MeLeu-D-Man-OPac (3 g).

NMR (CDCl$_3$,δ): 0.91–0.97 (m,6H), 1.39 (s) and 1.43 (s) (9H),1.40–1.86 (m,3H), 2.85 (s) and 2.88 (s) (3H), 4.80–4.88 (m) and 5.04–5.12 (m) (1H), 5.29 (d,1H), 5.40 (d,1H),6.11 (s) and 6.15 (s) (1H), 7.40–7.86 (m,10H).

Preparation 13

To 90% aqueous acetic acid (30 ml) of Boc-MeLeu-D-Man-OPac (3 g) was added zinc powder (3 g) and stirred for 1 hour at room temperature. After filtering the zinc residue, the solvent was evaporated in vacuo. Ethyl acetate (200 ml) was added to the residue, and washed with 10% aqueous citric acid, water, and saturated brine. After drying over anhydrous magnesium sulfate. The solvent was evaporated in vacuo, the resultant crude product was purified by silica gel chromatography, and eluted with mixture of methylene chloride, ethanol and acetic acid (20:1:0.1, v/v). The fractions containing the desired product were combined and evaporated in vacuo to obtain Boc-MeLeu-D-Man-OH (2.22 g).

NMR (CDCl$_3$,δ): 0.91–0.97 (m,6H), 1.28 (s) and 1.44 (s) (9H),1.40–1.80 (m,3H), 2.86 (s,3H), 4.80–4.98 (m,1H), 5.95 (s,1H), 7.39–7.50 (m,5H).

Preparation 14

Trichloroethyl (S)-2-chloropropionate (4.8 g) was used instead of benzyl (S)-2-chloro-3-(4-methoxyphenyl) propionate. Except above matter, Boc-MeLeu-D-Lac-OTce (7.98 g) was obtained according to a similar manner to that of Preparation 2.

NMR (CDCl$_3$,δ): 0.93–0.98 (m,6H), 1.47 (s,9H), 1.59 (d,3H), 1.50–1.78 (m,3H), 2.81 (s) and 2.84 (s) (3H), 4.64–5.05 (m,3H), 5.19 (q,1H).

Preparation 15

Boc-MeLeu-D-Lac-OTce (2.7 g) was used instead of Boc-MeLeu-D-Lac-OBzl. Except above matter, H-MeLeu-D-Lac-OTce.HCl (2.45 g) was obtained according to a similar manner to that of Preparation 4.

NMR (CDCl$_3$,δ): 0.95–1.03 (m,6H), 1.68 (d,3H), 1.80–2.16 (m,3H), 2.74–2.80 (m,3H), 3.80–3.99 (m,1H), 4.67 (d,1H), 4.96 (d,1H), 5.32 (q,1H), 9.80–10.10 (m,1H), 10.30–10.60 (m,1H).

Preparation 16

Boc-MeLeu-D-Man-OH (2.22 g) was used instead of Boc-MeLeu-D-p-MeOPhLac-OH. H-MeLeu-D-Lac-OTce.HCl (2.4 g) was used instead of H-MeLeu-D-Lac-OBzl.HCl. Except above matter, Boc-MeLeu-D-Man-MeLeu-D-Lac-OTce (3.33 g) was obtained according to a similar manner to that of Preparation 5.

NMR (CDCl$_3$,δ): 0.77–0.99 (m,12H), 1.35 (s,9H), 1.26–1.84 (m,9H), 2.79–2.98 (m,6H), 4.53–5.55 (m,5H), 6.15–6.24 (m,1H), 7.39–7.46 (m,5H).

Preparation 17

Boc-MeLeu-D-Man-MeLeu-D-Lac-OTce (1.5 g) was used instead of Boc-MeLeu-D-Man-OPac. Except above matter, Boc-MeLeu-D-Man-MeLeu-D-Lac-OH (1.46 g) was obtained according to a similar manner to that of Preparation 13.

NMR (CDCl$_3$,δ): 0.79–0.99 (m,12H), 1.37 (s,9H), 1.20–1.83 (m,9H), 2.79–2.96 (m,6H), 4.53–5.40 (m,3H), 6.14–6.26 (m,1H), 7.39–7.44 (m,5H).

Preparation 18

Boc-MeLeu-D-Man-MeLeu-D-Lac-OTce (1.5 g) was used instead of Boc-MeLeu-D-p-MeOPhLac-MeLeu-D-Lac-OBzl. Except above matter, H-MeLeu-D-Man-MeLeu-D-Lac-OTce.HCl (1.3 g) was obtained according to a similar manner to that of Preparation 7.

NMR (CDCl$_3$,δ): 0.78–0.98 (m,12H), 1.30–2.24 (m,9H), 2.78–2.97 (m,6H), 3.79–3.99 (m,1H), 4.52–5.56 (m,4H), 6.27–6.31 (m,1H),7.40–7.52 (m,5H), 9.52–9.90 (m,1H), 10.10–10.42 (m,1H).

Preparation 19

Boc-MeLeu-D-Man-MeLeu-D-Lac-OH (1.4 g) was used instead of Boc-MeLeu-D-p-MeOPhLac-OH. H-MeLeu-D-Man-MeLeu-D-Lac-OTce.HCl (1.3 g) was used instead of H-MeLeu-D-Lac-OBzl.HCl. Except above matter, Boc-MeLeu-D-Man-MeLeu-D-Lac-OTce (1.7 g) was obtained according to a similar manner to that of Preparation 5.

NMR (CDCl$_3$,δ): 0.76–1.18 (m,24H), 1.21–1.98 (m,2.7H), 2.79–3.10 (m,12H), 4.52–5.59 (m,8H), 6.13–6.25 (m,2H), 7.15–7.55 (m,10H).

Preparation 20

Boc-MeLeu-D-Man-MeLeu-D-Lac-MeLeu-D-Man-MeLeu-D-Lac-OTce was used instead of Boc-MeLeu-D Man-OPac. Except above matter, Boc-MeLeu-D-Man-MeLeu-D-Lac-MeLeu-D-Man-MeLeu-D-Lac-OH (1.07 g) was obtained according to a similar manner to that of Preparation 13.

NMR (CDCl$_3$,δ): 0.70–1.10 (m,24H), 1.35 (s,9H), 1.25–1.98 (m,18H), 2.78–3.09 (m,12H), 4.20–5.59 (m,6H), 6.10–6.37 (m,2H), 7.26–7.59 (m,10H).

Preparation 21

Boc-MeLeu-D-Man-MeLeu-D-Lac-MeLeu-D-Man-MeLeu-D-Lac-OH was used instead of Boc-MeLeu-D-p-MeOPhLac-MeLeu-D-Lac-MeLeu-D-p-MeOPhLac-MeLeu-D-Lac-OH. Except above matter, Boc-MeLeu-D-Man-MeLeu-D-Lac-MeLeu-D-Man-MeLeu-D-Lac-OC$_6$F$_5$ (0.96 g) was obtained according to a similar manner to that of Preparation 10.

NMR (CDCl$_3$,δ): 0.72–1.00 (m,24H), 1.10–1.95 (m,2.7H), 2.77–3.09 (m,12H), 4.40–5.68 (m,6H), 6.12–6.24 (m,2H), 7.22–7.58 (m,10H).

Preparation 22

To a solution of ethyl (R)-2-acetoxy-3-(4-nitrophenyl) propionate (5.62 g) in ethanol (50 ml) were added concentrated hydrochloric acid (2.5 ml) and 10% palladium on carbon (0.6 g). The mixture was hydrogenated under atmospheric pressure of hydrogen gas for 3 hours at room temperature. The catalyst was filtered off and the solvent was evaporated in vacuo. To the residue was added 0.05N hydrochloric acid (200 ml) and washed with ether (100 ml×2). Saturated aqueous sodium hydrogencarbonate was added to water layer until pH10, and extracted with ether (100 ml×4). After the ether layer was washed with saturated brine, it was dried over anhydrous magnesium sulfate and evaporated in vacuo. To the residue, benzene (40 ml), benzylalcohol (21 ml) and p-toluenesulfonic acid-mono hydrate (4.76 g) were added, and the mixture was heated under reflux for 4 hours. After ice-cooling down to room temperature, the solvent was evaporated in vacuo. To the residue was added water (200 ml) and washed with ether (100 ml×2). Saturated aqueous sodium hydrogencarbonate was added to water layer until pH10, extracted with ether (100 ml×4). After the ether layer was washed with saturated brine, it was dried over anhydrous magnesium sulfate and the solvent was evaporated in vacuo to give benzyl (R)-3-(4-aminophenyl)-2-hydroxypropionate (2.84 g).

NMR (CDCl$_3$,δ) 2.85 (dd,1H),2.6–3.6 (m,3H),3.00 (dd, 1H),4.38 (dd,1H), 5.15 (s,2H),6.53 (d,2H),6.90 (d,2H), 7.25–7.4 (m,5H)

IR (neat): 1740 cm$^{-1}$

Preparation 23

To a solution of benzyl (R)-3-(4-aminophenyl)-2-hydroxypropionate (0.26 g) in acetic acid (6 ml) was added paraformaldehyde (0.3 g), and further sodium cyanoborohydride (0.3 g) was added gradually, and stirred for 3 hours. To the solution of sodium bicarbonate (25 ml) and ice (25 g) was added reaction mixture gradually and was extracted with ethyl acetate (50 ml×2). After washing the ethyl acetate layer with saturated brine, it was dried over anhydrous magnesium sulfate. The solvent was evaporated in vacuo, the resultant crude product was purified by silica gel chromatography, and eluted with mixture of ethyl acetate and hexane (7:3, v/v). The fractions containing the desired product were combined and evaporated in vacuo to obtain benzyl (R)-3(4-dimethylaminophenyl)-2-hydroxypropionate (0.22 g). NMR (CDCl$_3$,δ) 2.64 (d,1H),2.91 (s,6H), 2.90 (dd,1H),3.04 (dd,1H),4.43 (ddd,1H), 5.18 (s,2H),6.63 (d,2H),7.01 (d,2H),7.35 (bs,5H)

IR (neat): 1733, 1612 cm$^{-1}$

Preparation 24

To a solution of Boc-MeLeu-OH (1.27 g), H-D-p-Me$_2$NPhLac-OBzl (1.47 g) in methylene chloride (20 ml)

were added under ice-cooling, dimethylaminopyridine (0.15 g), 1-ethyl-3-(3-dimethylaminopropyl) carbodiimide-hydrochloride (1.01 g), and stirred for 15 hours successively. The solvent was evaporated in vacuo. The water (50 ml) was added to residue and extracted with ethyl acetate (50 ml×3). After the ethyl acetate layer was washed with saturated brine, and dried over anhydrous sodium sulfate. The solvent was evaporated in vacuo, the resultant crude product was purified by silica gel chromatography, and eluted with mixture of ethyl acetate and hexane (4:1, v/v). The fractions containing the desired product were combined and evaporated in vacuo to give Boc-MeLeu-D-p-Me$_2$NPhLac-OBzl (1.69 g).

NMR (CDCl$_3$,δ) 0.90 (d,6H),1.4–1.65 (m,12H),2.63 (s) and 2.68 (s) (3H),2.93 (s,6H),3.05–3.15 (m,6H),4.65–4.80 (m) and 4.95–5.20 (m) (4H),6.62 (d,2H),7.03 (d,2H),7.1–7.2 (m,5H)

IR (KBr): 1747,1730,1693,1675, cm$^{-1}$

Preparation 25

To a solution of Boc-MeLeu-D-p-Me$_2$NPhLac-OBzl (1.67 g) in methanol (30 ml) and tetrahydrofuran (5 ml) was added 10% palladium on carbon (0.3 g), and hydrogenation was done in hydrogen gas under atmospheric pressure for 1 and 0.5 hour. After catalyst was filtrated, the solvent was evaporated in vacuo to give Boc-MeLeu-D-p-Me$_2$NPhLac-OH (1.44 g).

IR (KBr): 1741,1694 cm$^{-1}$

Preparation 26

To a mixture of Boc-MeLeu-D-p-Me$_2$NPhLac-OH (1.44 g) in triethylamine (1.92 ml) and dichloromethane (15 ml) was added under ice-cooling, bis(2-oxo-3-oxazolidinyl)phosphinic chloride (1.30 g) and stirred successively for 15 and ½ hours. The solvent was evaporated in vacuo, and water (50 ml) was added and extracted with ethyl acetate (50 ml×3). The ethyl acetate layer was washed with saturated brine, dried over anhydrous sodium sulfate. The solvent was evaporated in vacuo, the resultant crude product was purified by silica gel chromatography, and eluted with mixture of ethyl acetate and hexane (7:3, v/v). The fractions containing the desired product were combined and evaporated in vacuo to obtain Boc-MeLeu-D-p-Me$_2$NPhLac-MeLeu-D-Lac-OBzl (1.55 g).

NMR (CDCl$_3$,δ) 0.8–1.0 (m,12H),1.4–1.7 (m,18H), 2.7–3.1 (m,8H),2.90 (s,6H),5.65–6.5 (m,6H),6.65 (d,2H), 7.08 (d,2H),7.3–7.4 (m,5H)

IR (KBr): 1740,1695,1663 cm$^{-1}$

Preparation 27

Boc-MeLeu-D-p-Me$_2$NPhLac-MeLeu-D-Lac-OBzl (0.77 g) was used instead of Boc-MeLeu-D-p-Me$_2$NPhLac-OBzl. Except above matter, Boc-MeLeu-D-p-Me$_2$NPhLac-MeLeu-D-Lac-OH (637 mg) was obtained according to a similar manner to that of Preparation 25.

IR (KBr): 1739,1694,1663 cm$^{-1}$

Preparation 28

Boc-MeLeu-D-p-Me$_2$NPhLac-MeLeu-D-Lac-OBzl (765 mg) was dissolved in 4N hydrogen chloride in ethyl acetate (5 ml), and stirred for 2 hours at room temperature. After the solvent was evaporated in vacuo, it was azeotroped twice with toluene (10 ml) to obtain 2HCl.H-MeLeu-D-p-Me$_2$NPhLac-MeLeu-D-Lac-OBzl (783 mg)

IR (KBr): 1744,1647 cm$^{-1}$

Preparation 29

Boc-MeLeu-D-p-Me$_2$NPhLac-MeLeu-D-Lac-OH (0.64 g) was used instead of Boc-MeLeu-D-p-Me$_2$NPhLac-OH, 2HCl.H-MeLeu-D-p-Me$_2$NPhLac-MeLeu-D-Lac-OBzl (0.78 g) was used instead of HCl.H-MeLeu-D-Lac-OBzl. Except above matter, Boc-MeLeu-D-p-Me$_2$NPhLac-MeLeu-D-Lac-MeLeu-D-p-Me$_2$NPhLac-MeLeu-D-Lac-OBzl (0.88 g) was obtained according to a similar manner to that of Preparation 26.

NMR (CDCl$_3$,δ) 0.75–1.0 (m,24H),1.2–1.8 (m,2.7H), 2.65–3.1 (m,16H), 2.91 (s,12H),4.65–5.5 (m,10H),6.6–6.75 (m,4H),7.0-7.15 (m,4H),7.3–7.7 (m,5H)

IR (KBr): 1740,1694,1662 cm$^{-1}$

FAB-MS: 1243 [M+H]$^+$

Preparation 30

Boc-MeLeu-D-p-Me$_2$NPhLac-MeLeu-D-Lac-MeLeu-D-p-Me$_2$NPhLac-MeLeu-D-Lac-OBzl (0.87 g) was used instead of Boc-MeLeu-D-p-Me$_2$NPhLac-OBzl. Except above matter, Boc-MeLeu-D-p-Me$_2$NPhLac-MeLeu-D-Lac-MeLeu-D-p-Me$_2$NPhLac-MeLeu-D-Lac-OH (0.81 g) was obtained according to a similar manner to that of Preparation 25.

IR (KBr): 1735,1695,1662 cm$^{-1}$

Preparation 31

Boc-MeLeu-D-p-Me$_2$NPhLac-MeLeu-D-Lac-MeLeu-D-p-Me$_2$NPhLac-MeLeu-D-Lac-OH (0.81 g) was used instead of Boc-MeLeu-D-p-Me$_2$NPhLac-MeLeu-D-Lac-OBzl. Except above matter, 3HCl.H-MeLeu-D-p-Me$_2$NPhLac-MeLeu-D-Lac-MeLeu-D-p-Me$_2$NPhLac-MeLeu-D-Lac-OH (0.826 g) was obtained according to a similar manner to that of Preparation 28.

IR (KBr): 1743,1646 cm$^{-1}$

Preparation 32

The suspended solution of benzyl R)-3-(4-aminophenyl)-2-hydroxypropionate (0.27 g), bis(2-chloroethyl)ether (0.12 ml), potassium carbonate (0.28 g), and sodium iodide (0.075 g) in dimethylformamide (1 ml) were heated at 70°–90° C. for 7 hours. After cooling it down to room temperature, water (50 ml) was added and extracted with ether (25 ml×3). After the ether layer was washed with saturated brine, it was dried over anhydrous sodium sulfate. The solvent was evaporated in vacuo, the resultant crude product was purified by silica gel column chromatography, and eluted with mixture of hexane, ethyl acetate and ethanol (60:35:5, v/v). The fractions containing the desired product were combined and evaporated in vacuo to obtain benzyl (R)-2-hydroxy-3-(4-morpholinophenyl)propionate (0.14 g)

NMR (CDCl$_3$,δ) 2.66 (d,1H),2.91 (dd,1H),3.05 (dd,1H), 3.0–3.15 (m,4H), 3.8–3.95 (m,4H),4.45 (ddd,1H),5.18 (s,2H),6.79 (d,2H),7.05 (d,2H),7.3–7.4 (m,5H)

IR (neat): 1734 cm$^{-1}$

EI-MS: 341 [M]$^+$

Preparation 33

H-D-p-MorPhLac-OBzl (0.90 g) was used instead of H-D-p-Me$_2$NPhLac-OBzl. Except above matter, Boc-MeLeu-D-p-MorPhLac-MeLeu-D-Lac-OBzl (1.36 g) was obtained according to a similar manner to that of Preparation 24.

NMR (CDCl$_3$,δ) 0.9 (d,6H),1.4–1.65 (m,12H),2.63 (s) and 2.66 (s) (3H), 3.05–3.2 (m,6H),3.85–3.95 (m,4H), 4.7–4.8 (m) and 4.95–5.25 (m) (4H),6.80 (d,2H),7.07 (d,2H),7.1–7.2 (m,5H)

IR (KBr): 1740,1695 cm$^{-1}$

Preparation 34

Boc-MeLeu-D-p-MorPhLac-OBzl (1.35 g) was used instead of Boc-MeLeu-D-p-Me$_2$NPhLac-OBzl. Except above matter, Boc-MeLeu-D-p-MorPhLac-OH (1.08 g) was obtained according to a similar manner to that of Preparation 25.

IR (KBr): 1742,1695 cm$^{-1}$

Preparation 35

Boc-MeLeu-D-p-MorPhLac-OH (1.08 g) was used instead of Boc-MeLeu-D-p-Me$_2$NPhLac-OH. Except above matter, Boc-MeLeu-D-p-MorPhLac-MeLeu-D-Lac-OBzl (1.49 g) was obtained according to a similar manner to that of Preparation 26.

NMR (CDCl$_3$,δ) 0.85–0.95 (m,12H),1.4–1.7 (m,18H), 2.78 (s),2.81 (s) and 2.88 (s) (6H),3.0–3.1 (m,2H),3.1–3.15 (m,4H),3.85–3.9 (m,4H),4.65–4.75 (m) and 4.9–5.5 (m) (6H),6.82 (d,2H),7.13 (d,2H),7.3–7.4 (m,5H)

IR (KBr): 1740,1694,1662 cm$^{-1}$

Preparation 36

Boc-MeLeu-D-p-MorPhLac-MeLeu-D-Lac-OBzl (0.74 g) was used instead of Boc-MeLeu-D-p-Me$_2$NPhLac-OBzl. Except above matter, Boc-MeLeu-D-p-MorPhLac-MeLeu-D-Lac-OH (0.64 g) was obtained according to a similar manner to that of Preparation 25.

IR (KBr): 1741,1694,1664 cm$^{-1}$

Preparation 37

Boc-MeLeu-D-p-MorPhLac-MeLeu-D-Lac-OBzl (0.74 g) was used instead of Boc-MeLeu-D-p-Me$_2$NPhLac-MeLeu-D-Lac-OBzl. Except above matter, 2HCl.H-MeLeu-D-p-MorPhLac-MeLeu-D-Lac-OBzl (0.73 g) was obtained according to a similar manner to that of Preparation 28.

IR (KBr): 1744,1648 cm$^{-1}$

Preparation 38

Boc-MeLeu-D-p-MorPhLac-MeLeu-D-Lac-OH (0.64 g) was used instead of Boc-MeLeu-D-p-Me$_2$NPhLac-OH, 2HCl.H-MeLeu-D-p-MorPhLac-MeLeu-D-Lac-OBzl (0.73 g) was used instead of HCl.H-MeLeu-D-Lac-OBzl. Except above matter, Boc-MeLeu-D-p-MorPhLac-MeLeu-D-Lac-MeLeu-D-p-MorPhLac-MeLeu-D-Lac-OBzl (1.08 g) was obtained according to a similar manner to that of Preparation 26.

NMR (CDCl$_3$,δ) 0.8–1.05 (m,24H),1.15–1.8 (m,2.7H), 2.65–3.2 (m,24H), 3.8–3.95 (m,8H),4.65–4.75 (m) and 4.9–5.5 (m) (10H),6.75–6.9 (m,4H), 7.05–7.2 (m,4H), 7.3–7.4 (m,5H)

IR (KBr): 1738,1694,1663 cm$^{-1}$

FAB-MS: 1227 [M+H]$^+$

Preparation 39

Boc-MeLeu-D-p-MorPhLac-MeLeu-D-Lac-MeLeu-D-p-MorPhLac-MeLeu-D-Lac-OBzl (1.07 g) was used instead of Boc-MeLeu-D-p-Me$_2$NPhLac-OBzl. Except above matter, Boc-MeLeu-D-p-MorPhLac-MeLeu-D-Lac-MeLeu-D-p-MorPhLac-MeLeu-D-Lac-OH (0.96 g) was obtained according to a similar manner to that of Preparation 25.

IR (KBr): 1739,1694,1663 cm$^{-1}$

Preparation 40

Boc-MeLeu-D-p-MorPhLac-MeLeu-D-Lac-MeLeu-D-p-MorPhLac-MeLeu-D-Lac-OH (0.96 g) was used instead of Boc-MeLeu-D-p-Me$_2$NPhLac-MeLeu-D-Lac-OBzl. Except above matter, 3HCl.H-MeLeu-D-p-MorPhLac-MeLeu-D-Lac-MeLeu-D-p-MorPhLac-MeLeu-D-Lac-OH (1.02 g) was obtained according to a similar manner to that of Preparation 28.

IR (KBr): 1741,1646 cm$^{-1}$

Preparation 41

The suspended solution of benzyl (R)-3-(4-aminophenyl)-2-hydroxypropionate (1.53 g), 1,4-dibromobutane (0.61 ml), potassium carbonate (2.07 g) and sodium iodide (0.37 g) in dimethylformamide (5 ml) were stirred at room temperature for 71 hours. To the solution was added water (50 ml) and extracted with ether (50 ml, 25 ml×2). After the ether layer was washed with saturated brine, it was dried over anhydrous sodium sulfate. The solvent was evaporated in vacuo, the resultant crude product was purified by silica gel column chromatography, and eluted with mixture of hexane and ethyl acetate (4:1, v/v). The fractions containing the desired product were combined and evaporated in vacuo to obtain benzyl (R)-2-hydroxy-3-(4-pyrrolidinophenyl) propionate (1.35 g).

NMR (CDCl$_3$,δ) 1.95–2.05 (m,4H),2.61 (d,1H),2.90 (dd, 1H),3.03 (dd,1H), 3.2–3.3 (m,4H),4.43 (ddd,1H),5.18 (s,2H),6.45 (d,2H),6.99 (d,2H),7.3–7.4 (m,5H)

IR (neat): 1732 cm$^{-1}$

Preparation 42

H-D-p-PyrPhLac-OBzl (1.34 g) was used instead of H-D-p-Me$_2$NPhLac-OBzl. Except above matter, Boc-MeLeu-D-p-PyrPhLac-OBzl (1.79 g) was obtained according to a similar manner to that of Preparation 24.

NMR (CDCl$_3$,δ) 0.92 (d,6H),1.4–1.65 (m,12H),1.95–2.1 (m,4H),2.47 (s) and 2.52 (s) (3H),3.0–3.15 (m,2H),3.2–3.35 (m,4H),4.7–4.8 (m) and 5.0–5.25 (m) (4H),6.46 (d,2H),7.02 (d,2H), 7.1–7.2 (m,5H)

IR (KBr): 1750,1740,1692,1672 cm$^{-1}$

Preparation 43

Boc-MeLeu-D-p-PyrPhLac-OBzl (1.78 g) was used instead of Boc-MeLeu-D-p-Me$_2$NPhLac-OBzl. Except above matter, Boc-MeLeu-D-p-PyrPhLac-OH (1.44 g) was obtained according to a similar manner to that of Preparation 25.

IR (KBr): 1740,1695 cm$^{-1}$

Preparation 44

Boc-MeLeu-D-p-PyrPhLac-OH (1.44 g) was used instead of Boc-MeLeu-D-p-Me$_2$NPhLac-OH. Except above matter, Boc-MeLeu-D-p-PyrPhLac-MeLeu-D-Lac-OBzl (1.53 g) was obtained according to a similar manner to that of Preparation 26.

NMR (CDCl$_3$,δ) 0.8–0.95 (m,12H),1.4–1.7 (m,18H), 1.95–2.05 (m,4H), 2.7–3.05 (m,8H),3.2–3.3 (m,4H), 5.65–5.75 (m) and 5.9–6.5 (m) (6H), 6.47 (d,2H),7.06 (d,2H),7.3–7.4 (m,5H)

IR (KBr): 1741,1695,1662 cm$^{-1}$

Preparation 45

Boc-MeLeu-D-p-PyrPhLac-MeLeu-D-Lac-OBzl (0.76 g) was used instead of Boc-MeLeu-D-p-Me$_2$NPhLac-OBzl. Except above matter, Boc-MeLeu-D-p-PyrPhLac-MeLeu-D-Lac-OH (0.65 g) was obtained according to a similar manner to that of Preparation 25.

IR (KBr): 1740,1695,1664 cm$^{-1}$

Preparation 46

Boc-MeLeu-D-p-PyrPhLac-MeLeu-D-Lac-OBzl (0.76 g) was used instead of Boc-MeLeu-D-p-Me$_2$NPhLac-MeLeu-D-Lac-OBzl. Except above matter, 2HCl.H-MeLeu-D-p-PyrPhLac-MeLeu-D-Lac-OBzl (0.77 g) was obtained according to a similar manner to that of Preparation 28.

IR (KBr): 1743,1646 cm$^{-1}$

Preparation 47

Boc-MeLeu-D-p-PyrPhLac-MeLeu-D-Lac-OH (0.65 g) was used instead of Boc-MeLeu-D-p-Me$_2$NPhLac-OH, 2HCl.H-MeLeu-D-p-PyrPhLac-MeLeu-D-Lac-OBzl (0.76 g) was used instead of HCl.H-MeLeu-D-Lac-OBzl. Except above matter, Boc-MeLeu-D-p-PyrPhLac-MeLeu-D-Lac-MeLeu-D-p-PyrPhLac-MeLeu-D-Lac-OBzl (0.82 g) was obtained according to a similar manner to that of Preparation 26.

NMR (CDCl$_3$,δ) 0.75–1.05 (m,24H),1.1–1.75 (m,2.7H), 1.9–2.1 (m,8H), 2.65–3.1 (m,28H),3.1–3.3 (m,8H),4.6–4.8 (m) and 4.9–5.5 (m) (10H), 6.35–6.55 (m,4H),7.0–7.2 (m,4H),7.3–7.4 (m,5H)

IR (KBr): 1740,1695,1664 cm$^{-1}$

FAB-MS: 1295 [M+H]$^+$

Preparation 48

Boc-MeLeu-D-p-PyrPhLac-MeLeu-D-Lac-MeLeu-D-p-PyrPhLac-MeLeu-D-Lac-OBzl (0.80 g) was used instead of Boc-MeLeu-D-p-Me$_2$NPhLac-OBzl. Except above matter, Boc-MeLeu-D-p-PyrPhLac-MeLeu-D-Lac-MeLeu-D-p-PyrPhLac-MeLeu-D-Lac-OH (0.74 g) was obtained according to a similar manner to that of Preparation 25.

IR (KBr): 1740,1695,1664 cm$^{-1}$

Preparation 49

Boc-MeLeu-D-p-PyrPhLac-MeLeu-D-Lac-MeLeu-D-p-PyrPhLac-MeLeu-D-Lac-OH (0.74 g) was used instead of Boc-MeLeu-D-p-Me$_2$NPhLac-MeLeu-D-Lac-OBzl. Except above matter, 3HCl.H-MeLeu-D-p-PyrPhLac-MeLeu-D-Lac-MeLeu-D-p-PyrPhLac-MeLeu-D-Lac-OH (0.81 g) was obtained according to a similar manner to that of Preparation 28.

IR (KBr): 1741,1647 cm$^{-1}$

Preparation 50

1,4-dibromobutane (0.56 ml) was used instead of 1,5-dibromopentane. Except above matter, benzyl (R)-2-hydroxy-3-(4-piperidinophenyl) propionate (1.05 g). was obtained according to a similar manner to that of Preparation 41.

NMR (CDCl$_3$,δ): 1.50–1.80 (m,6H),2.65 (d,1H),2.90 (dd, 1H),3.05 (dd,1H), 3.05–3.2 (m,4H),4.44 (ddd,1H),5.17 (s,2H),6.82 (d,2H),7.01 (d,2H),7.3–7.4 (m,5H)

IR (neat): 1720cm$^{-1}$

Preparation 51

H-D-p-PipPhLac-OBzl (0.79 g) was used instead of H-D-p-Me$_2$NPhLac-OBzl. Except above matter Boc-MeLeu-D-p-PipPhLac-MeLeu-D-Lac-OBzl (1.71 g) was obtained according to a similar manner to that of Preparation 24.

NMR (CDCl$_3$,δ): 0.90 (d,6H),1.4–1.8 (m,18H),2.62 (s) and 2.66 (s) (3H),3.0–3.15 (m,6H),4.65–4.75 (m) and 4.95–5.25 (m) (4H),6.82 (d,2H), 7.03 (d,2H),7.2–7.35 (m,5H)

IR (KBr): 1741,1695 cm$^{-1}$

Preparation 52

Boc-MeLeu-D-p-PipPhLac-OBzl (1.68 g) was used instead of Boc-MeLeu-D-p-Me$_2$NPhLac-OBzl. Except above matter, Boc-MeLeu-D-p-PipPhLac-OH (1.38 g) was obtained according to a similar manner to that of Preparation 25.

IR (KBr): 1740,1694 cm$^{-1}$

Preparation 53

Boc-MeLeu-D-p-PipPhLac-OH (1.38 g) was used instead of Boc-MeLeu-D-p-Me$_2$NPhLac-OH. Except above matter, Boc-MeLeu-D-p-PipPhLac-MeLeu-D-Lac-OBzl (2.01 g) was obtained according to a similar manner to that of Preparation 26

NMR (CDCl$_3$,δ): 0.8–0.95 (m,12H),1.3–1.75 (m,24H), 2.7–3.15 (m,12H), 4.65–4.75 (m) and 4.9–6.4 (m,6H),6.84 (d,2H),7.09 (d,2H),7.3–7.4 (m,5H)

IR (KBr): 1740,1695,1664 cm$^{-1}$

Preparation 54

Boc-MeLeu-D-p-PipPhLac-MeLeu-D-Lac-OBzl (0.99 g) was used instead of Boc-MeLeu-D-p-Me$_2$NPhLac-OBzl. Except above matter, Boc-MeLeu-D-p-PipPhLac-MeLeu-D-Lac-OH (0.84 g) was obtained according to a similar manner to that of Preparation 25.

IR (KBr): 1740,1695,1665 cm$^{-1}$

Preparation 55

Boc-MeLeu-D-p-PipPhLac-MeLeu-D-Lac-OBzl (0.98 g) was used instead of Boc-MeLeu-D-p-Me$_2$NPhLac-MeLeu-D-Lac-OBzl. Except above matter, 2HCl.H-MeLeu-D-p-PipPhLac-MeLeu-D-Lac-OBzl (1.06 g) was obtained according to a similar manner to that of Preparation 28.

IR (KBr): 1744,1649 cm$^{-1}$

Preparation 56

Boc-MeLeu-D-p-PipPhLac-MeLeu-D-Lac-OH (0.84 g) was used instead of Boc-MeLeu-D-p-Me$_2$NPhLac-OH, 2HCl.H-MeLeu-D-p-PipPhLac-MeLeu-D-Lac-OBzl (1.06 g) was used instead of HCl.H-MeLeu-D-Lac-OBzl. Except above matter, Boc-MeLeu-D-p-PipPhLac-MeLeu-D-Lac-MeLeu-D-p-PipPhLac-MeLeu-D-Lac-OBzl (1.18 g) was obtained according to a similar manner to that of Preparation 26.

NMR (CDCl$_3$,δ): 0.75–1.0 (m,24H),1.05–1.8 (m,39H), 2.65–3.2 (m,24H), 4.65–4.75 (m) and 4.9–5.5 (m) (10H), 6.8–6.9 (m,4H),7.0–7.15 (m,4H),7.3–7.4 (m,5H)

IR (KBr): 1738,1694,1663 cm$^{-1}$

FAB-MS: 1323 [M+H]$^+$

Preparation 57

Boc-MeLeu-D-p-PipPhLac-MeLeu-D-Lac-MeLeu-D-p-PipPhLac-MeLeu-D-Lac-OBzl (1.17 g) was used instead of Boc-MeLeu-D-p-Me$_2$NPhLac-OBzl. Except above matter, Boc-MeLeu-D-p-PipPhLac-MeLeu-D-Lac-MeLeu-D-p-PipPhLac-MeLeu-D-Lac-OH (1.11 g) was obtained according to a similar manner to that of Preparation 25.

IR (KBr): 1739,1693,1662 cm$^{-1}$

Preparation 58

Boc-MeLeu-D-p-PipPhLac-MeLeu-D-Lac-MeLeu-D-p-PipPhLac-MeLeu-D-Lac-OH (1.10 g) was used instead of Boc-MeLeu-D-p-Me$_2$NPhLac-MeLeu-D-Lac-OBzl. Except above matter 3HCl.H-MeLeu-D-p-PipPhLac-MeLeu-D-Lac-MeLeu-D-p-PipPhLac-MeLeu-D-Lac-OH (1.24 g) was obtained according to a similar manner to that of Preparation 28.

IR (KBr): 1742,1652 cm$^{-1}$

Preparation 59

Under nitrogen atmosphere, to a suspended solution of anhydrous tetrahydrofuran (1 ml) and metal magnesium (0.3 g) was added dropwise a solution of 4-(2-methoxyethoxy) bromobenzene (2.9 g) in anhydrous tetrahydrofuran (15 ml) at room temperature. After the dropping, the solution was heated under reflux at 100° C. for 15 minutes, and then the residue was cooled down to –10° C., added to cuprous bromide.dimethylsulfide complex (1.29 g), and stirred for 30 minutes at –5° C.~3° C. Further, it was cooled down to –60° C., and the solution (5 ml) of benzyl (R)-2,3-epoxypropionate (0.74 g) in anhydrous tetrahydrofuran was added dropwise for 30 minutes and stirred for 1 and ½ hour successively. To the solution were added saturated aqueous ammonium chloride (10 ml), and water (50 ml), and was extracted with ethyl acetate (100 ml×2). After washing the ethyl acetate layer with saturated brine, the solution was dried over sodium sulfate and evaporated in vacuo. The solvent was evaporated in vacuo, the resultant crude product was purified by silica get chromatography, and eluted with mixture of ethyl acetate and hexane (1:3, v/v). The fractions containing the desired product were combined and evaporated in vacuo to obtain benzyl (R)-4-(2-methoxyethoxy) phenyl lactic acid (1.09 g).

NMR (CDCl$_3$,δ): 2.92 (dd,1H),3.06 (dd,1H),3.47 (s,3H), 3.74 (t,2H),4.08 (t,2H),4.45 (dd,1H),5.17 (s,2H),6.8 (d,2H), 7.0 (d,2H),7.29–7.48 (m,5H)

Preparation 60

H-D-p-MEPhLac-OBzl (0.92 g) was used instead of H-D-p-Me$_2$NPhLac-OBzl. Except above matter, Boc-MeLeu-D-p-MEPhLac-MeLeu-D-Lac-OBzl (1.15 g) was obtained according to a similar manner to that of Preparation 24.

NMR (CDCl$_3$,δ): 0.90 (d,6H),1.4–1.65 (m,12H),2.6–2.7 (m,3H),3.01–3.12 (m,2H),3.45 (s,3H),3.67–3.78 (m,2H), 4.02–4.12 (m,2H),4.62–5.22 (m,4H),6.77–6.86 (m,2H), 7.02–7.12 (m,2H),7.22–7.4 (m,5H)

FAB-MS: 458 [M-Boc+H]$^+$

Preparation 61

Boc-MeLeu-D-p-MEPhLac-OBzl (1.5 g) was used instead of Boc-MeLeu-D-p-Me$_2$NPhLac-OBzl. Except above matter Boc-MeLeu-D-p-MEPhLac-OH (1.29 g) was obtained according to a similar manner to that of Preparation 25.

NMR (CDCl$_3$,δ): 0.82–1.03 (m,6H),1.38–1.8 (m,12H), 2.7–2.9 (m,3H), 3.0–3.3 (m,2H),3.45 (s,3H),3.65–3.78 (m,2H),4.05–4.17 (m,2H),4.4–4.51 (m) and 4.63–4.77 (m) (1H),5.2–5.38 (m,1H),6.85 (d,2H),7.13 (d,2H)

Preparation 62

Boc-MeLeu-D-p-MEPhLac-OH (1.29 g) was used instead of Boc-MeLeu-D-p-Me$_2$NPhLac-OH. Except above matter Boc-MeLeu-D-p-MEPhLac-MeLeu-D-Lac-OBzl (1.87 g) was obtained according to a similar manner to that of Preparation 26.

NMR (CDCl$_3$,δ): 0.80–0.95 (m,12H),1.4–1.7 (m,18H), 2.79–2.97 (m,6H), 3.01–3.09 (m,2H),3.45 (s,3H),3.64–3.79 (m,2H),4.02–4.17 (m,2H), 4.6–4.8 (m) and 4.9–5.43 (m) (6H),6.85 (d,2H),7.07–7.19 (m,2H),7.3–7.42 (m,5H)

FAB-MS: 657 [M-Boc+H]$^+$

Preparation 63

Boc-MeLeu-D-p-MEPhLac-MeLeu-D-Lac-OBzl (0.85 g) was used instead of Boc-MeLeu-D-p-Me$_2$NPhLac-OBzl. Except above matter, Boc-MeLeu-p-MEPhLac-MeLeu-D-Lac-OH (0.67 g) was obtained according to a similar manner to that of Preparation 25.

NMR (CDCl$_3$,δ): 0.80–0.99 (m,12H),1.4–1.7 (m,18H), 2.76–2.95 (m,6H), 3.0–3.19 (m,2H),3.45 (s,3H),3.74—3.8 (m,2H),4.04–4.18 (m,2H),4.65–4.9 (m) and 5.12–5.39 (m) (4H),6.83 (d,2H),7.15 (d,2H)

Preparation 64

Boc-MeLeu-D-p-MEPhLac-MeLeu-D-Lac-OBzl (0.86g) was used instead of Boc-MeLeu-D-p-Me$_2$NPhLac-MeLeu-D-Lac-OBzl. Except above matter HCl.H-MeLeu-D-p-MEPhLac-MeLeu-D-Lac-OBzl (0.86 g) was obtained according to a similar manner to that of Preparation 28.

NMR (CDCl$_3$,δ): 0.79–1.03 (m,12H),1.21–2.18 (m,9H), 2.56–2.72 (m,3H), 2.83–2.99 (m,3H),2.99–3.12 (m,2H), 3.45 (s,3H),3.63–3.8 (m,3H),4.03–4.17 (m,2H),5.03–5.58 (m,5H),6.86 (d,2H),7.07–7.43 (m,7H)

Preparation 65

Boc-MeLeu-D-p-MEPhLac-MeLeu-D-Lac-OH (0.66 g) was used instead of Boc-MeLeu-D-p-Me$_2$NPhLac-OH, HCl.H-MeLeu-D-p-MEPhLac-MeLeu-D-Lac-OBzl (0.84 g) was used instead of HCl.H-MeLeu-D-Lac-OBzl. Except above matter Boc-MeLeu-D-p-MEPhLac-MeLeu-D-Lac-MeLeu-D-p-MEPhLac-MeLeu-D-Lac-OBzl (1.24 g) was obtained according to a similar manner to that of Preparation 26.

NMR (CDCl$_3$,δ): 0.77–1.0 (m,24H),1.15–1.79 (m,2.7H), 2.7–3.17 (m,16H), 3.45 (s,6H),3.66–3.78 (m,4H),4.02–4.14 (m,4H),4.6–4.78 (m) and 4.9–5.5 (m) (10H),6.78–6.95 (m,4H),7.03–7.18 (m,4H),7.3–7.42 (m,5H)

FAB-MS: 1205 [M-Boc+H]$^+$

Preparation 66

Boc-MeLeu-D-p-MEPhLac-MeLeu-D-Lac-MeLeu-D-p-MEPhLac-MeLeu-D-Lac-OBzl (1.22 g) was used instead of Boc-MeLeu-D-p-Me$_2$NPhLac-OBzl. Except above matter Boc-MeLeu-D-p-MEPhLac-MeLeu-D-Lac-MeLeu-D-p-MEPhLac-MeLeu-D-Lac-OH (1.03 g) was obtained according to a similar manner to that of Preparation 25.

NMR (CDCl$_3$,δ): 0.77–1.02 (m,24H),1.18–1.8 (m,2.7H), 2.7–3.09 (m,16H), 3.45 (s,6H),3.65–3.8 (m,4H),3.98–4.17 (m,4H),4.58–5.77 (m,5H), 6.84 (d,4H),7.14 (d,4H)

Preparation 67

Under nitrogen atmosphere, at −15° C., to dichloromethane solution of (R)-isopropylidene glycerol (2 g) and triethylamine (5.05 ml) was added dropwise dichloromethane solution of trifluoromethanesulfonic anhydride (3.05 ml). After stirring for half an hour successively, dichloromethane was added and the mixture was washed with water, saturated aqueous sodium bicarbonate, saturated brine and dried over anhydrous sodium sulfate and filtrated with silica gel. The solvent was evaporated in vacuo and azeotroped by toluene to gain the crude product of triflate. To tetrahydrofuran solution of magnesium (0.61 g) was added dropwise tetrahydrofuran solution of 2-bromoanisole (2.82 ml), and for half an hour it was heated under reflux. Under ice-cooling, the copper bromide dimethylsulfide complex (0.99 g) was then added. Further tetrahydrofuran solution of the above crude product of triflate was added dropwise and stirred for 2 hours successively, aqueous ammonium chloride was added, and was extracted with ethyl acetate. The extract was dried magnesium over sodium sulfate. The solvent was evaporated in vacuo, the resultant crude product was purified by silica gel column chromatography, and eluted with mixture of ethyl acetate and hexane (4:1, v/v). The fractions containing the desired product were combined and evaporated in vacuo to obtain (R)-4-(2-methoxybenzyl)-2,2-dimethyl-1,3-dioxolane (2.25 g).

NMR (CDCl$_3$,δ): 1.35 (s,3H),1.44 (s,3H),2.81 (dd,1H), 3.02 (dd,1H),3.66 (dd,1H),3.81 (s,3H),3.88 (dd,1H),4.37 (dt, 1H),6.79–6.93 (m,2H),7.13–7.25 (m,2H)

Preparation 68

(R)-4-(2-methoxybenzyl)-2,2-dimethyl-1,3-dioxolane (2.2 g) was dissolved in ethanol (20 ml) and to 6N-aqueous hydrochloric acid solution was added and stirred for 2 hours at room temperature. After evaporating ethanol in vacuo, water was added and extracted with ethyl acetate. After washing with aqueous saturated sodium bicarbonate solution, it was dried over sodium sulfate and evaporated in vacuo to give (R)-3-(2- methoxyphenyl)propane-1,2-diol (1.62 g).

NMR (CDCl$_3$,δ): 2.75–2.93 (m,2H),3.40–4.00 (m,3H), 3.85 (s,3H),6.82–6.97 (m,2H),7.12–7.28 (m,2H)

Preparation 69

Under ice-cooling, to a solution of (R)-3-(2-methoxyphenyl)propane-1,2-diol (1.62 g) and imidazole (0.92 g) in dimethylformamide was added t-butyldimethylsilyl chloride (1.36 g), and stirred for 15minutes successively. The reaction solution was poured into water, extracted with ethyl acetate, and dried over sodium sulfate. After the solvent was evaporated in vacuo, the gained crude product was purified by silica gel column chromatography, and it was eluted with a mixed solvent of hexane and ethyl acetate (7:1, v/v). The fractions containing the desired product were combined and evaporated in vacuo to obtain (R)-1-t-butyldimethylsiloxy-3-(2-methoxyphenyl)-2-propanol (2.22 g).

NMR (CDCl$_3$,δ): 0.063 (s,6H),0.91 (s,9H),2.59 (d,1H), 2.78–2.84 (m,2H), 3.45–3.68 (m,2H),3.88 (s,3H),3.89–3.97 (m,1H),6.83–6.94 (m,2H),7.16–7.26 (m,2)

Preparation 70

Under ice-cooling, to a dichloromethane solution of (R)1-t-butyldimethylsiloxy-3-(2-methoxyphenyl)-2-propanol (2.2 g) were added diisopropylethylamine (2.59 ml) and methoxymethylchloride (0.85 ml) and stirred at room temperature for 18 hours. After evaporating dichloromethane in vacuo, water was added, extracted with ethyl acetate, and dried over magnesium sulfate. The solvent was evaporated in vacuo and the resultant crude product was purified by silica gel column chromatography, and it was eluted with a mixed solvent of hexane and ethyl acetate (6:1, v/v). The fractions containing the desired product were combined and evaporated in vacuo to obtain (R)-1-t-butyldimethylsiloxy-2-methoxymethoxy-3-(2-methoxyphenyl)propane (2.22 g).

NMR (CDCl$_3$,δ): 0.04 (s,6H),0.89 (s,9H),2.68 (dd,1H), 2.91 (dd,1H),3.15 (s,3H),3.63 (d,2H),3.79 (s,3H),3.82–3.99 (m,1H),4.52 (d,1H),4.67 (d,1H), 6.80–6.91 (m,2H), 7.11–7.26 (m,2H)

Preparation 71

Under ice-cooling, to a tetrahydrofuran solution of (R)-1-t-butyldimethylsiloxy-2-methoxymethoxy-3-(2-methoxyphenyl) propane (2.2 g) was added a solution of n tetrabutylammonium fluoride (1 mol/l, 6.46 ml) in tetrahydrofuran and stirred for 2 hours successively. After tetrahydrofuran was evaporated in vacuo, water was added, extracted with ethyl acetate, and dried over magnesium sulfate. The solvent was evaporated in vacuo, the gained crude product was purified by silica gel column chromatography, and eluted with a mixed solvent of hexane and ethyl acetate (1:1, v/v). The fractions containing the desired product were combined and evaporated in vacuo to obtain (R)-2-methoxymethoxy-3-(2-methoxyphenyl)-1-propanol (1.51 g).

NMR (CDCl$_3$,δ): 2.85 (d,2H),3.36 (s,3H),3.41–3.70 (m,2H),3.83 (s,3H), 3.82–3.98 (m,1H),4.62 (d,1H),4.68 (d,1H),6.83–6.92 (m,2H),7.12–7.26 (m,2H)

Preparation 72

To dimethylformamide solution (17.5 ml) of (R)-2-methoxymethoxy-3-(2-methoxyphenyl)-1-propanol (1.5 g) was added pyridinium dichromate (8.73 g) and stirred for 15 hours at room temperature. To the reaction solution was added silica gel and ethyl acetate. The mixture was filtered through silica gel. The solvent was evaporated in vacuo, ethyl acetate-benzene (1:1) was added, washed with water and dried over magnesium sulfate. After the solvent was evaporated in vacuo, tetrahydrofuran (6 ml), 6N-aqueous hydrochloric acid (6 ml) was added and stirred for 2 hours at 50° C. After tetrahydrofuran was evaporated in vacuo, water was added, extracted with ethyl acetate, washed with water, and dried over magnesium sulfate. After the solvent was evaporated in vacuo, dimethylformamide, potassium carbonate (0.7 g) was added and under ice-cooling, benzyl bromide was added dropwise. After the mixture was stirred for 1 and ½ hour, water was added, extracted with ethyl acetate, and dried over magnesium sulfate. The solvent was evaporated in vacuo, the resultant crude product was purified by silica gel column chromatography, and eluted with mixture of hexane and ethyl acetate (3:1, v/v). The fractions containing the desired product were combined and evaporated in vacuo to obtain benzyl (R)-2-hydroxy-3-(2-methoxyphenyl)propionate (1.02 g).

NMR (CDCl$_3$,δ): 2.92 (d,1H),3.03 (dd,1H),3.18 (dd,1H), 3.83 (s,3H),4.46–4.58 (m,1H),5.11 (d,1H),5.19 (d,1H), 6.83–6.91 (m,2H),7.18–7.38 (m,7H)

EI-MS:286 [M]$^+$

Preparation 73

H-D-o-MeOPhLac-OBzl (1 g) was used instead of H-D-p-Me$_2$NPhLac-OBzl. Except above matter, Boc-MeLeu-D-o-MeOPhLac-OBzl (1.73 g) was obtained according to a similar manner to that of Preparation 24.

NMR (CDCl$_3$,δ): 0.88 (d,6H),1.18–1.65 (m,12H), 2.58–2.78 (m,3H),2.98–3.38 (m,2H),3.79 (s,3H),4.66–5.00 (m,1H),5.08–5.18 (m,2H),5.20–5.40 (m,1H),6.76–6.89 (m,2H),7.07–7.40 (m,7H)

Preparation 74

Boc-MeLeu-D-o-MeOPhLac-OBzl (1.7 g) was used instead of Boc-MeLeu-D-p-Me$_2$NPhLac-OBzl. Except above matter, Boc-MeLeu-D-o-MeOPhLac-OH (1.54 g) was obtained according to a similar manner to that of Preparation 25.

NMR (CDCl$_3$,δ): 0.80–0.95 (m,6H),1.20–1.62 (m,12H), 2.69–2.74 (m,3H), 3.02 (dd,1H),3.31–3.43 (m,1H),3.82 (s,3H),4.51–4.72 (m,1H),5.25–5.43 (m,1H),6.80–6.92 (m,2H),7.11–7.26 (m,2H)

Preparation 75

Boc-MeLeu-D-o-MeOPhLac-OH (1.5 g) was used instead of Boc-MeLeu-D-p-Me$_2$NPhLac-OH. Except above matter, Boc-MeLeu-D-o-MeOPhLac-MeLeu-D-Lac-OBzl (2.09 g) was obtained according to a similar manner to that of Preparation 26.

NMR (CDCl$_3$,δ): 0.82–0.99 (m,12H),1.20–1.80 (m,18H), 2.70–3.34 (m, 8H),3.84 (s) and 3.79 (s) (3H),4.59–5.58 (m,6H),6.81–6.92 (m,2H),7.13–7.35

Preparation 76

Boc-MeLeu-D-o-MeOPhLac-MeLeu-D-Lac-OBzl (1 g) was used instead of Boc-MeLeu-D-p-Me$_2$NPhLac-OBzl. Except above matter, Boc-MeLeu-D-o-MeOPhLac-MeLeu-D-Lac-OH (0.98 g) was obtained according to a similar manner to that of Preparation 25.

NMR (CDCl$_3$,δ): 0.82–1.01 (m,12H),1.10–1.78 (m,18H), 2.69–3.21 (m,8H), 3.86 (s,3H),4.62–5.92 (m,4H),6.81–6.92 (m,2H),7.12–7.26 (m,2H)

Preparation 77

Boc-MeLeu-D-o-MeOPhLac-MeLeu-D-Lac-OBzl (1 g) was used instead of Boc-MeLeu-D-p-Me$_2$NPhLac-MeLeu-D-Lac-OBzl. Except above matter, HCl.H-MeLeu-D-o MeOPhLac-MeLeu-D-Lac-OBzl (0.94 g) was obtained according to a similar manner to that of Preparation 28.

NMR (CDCl$_3$,δ): 0.68–1.01 (m,12H),1.10–1.98 (m,9H), 2.56–3.40 (m,8H), 3.67–3.82 (m,1H),3.84 (s,3H),4.95–5.72 (m,5H),6.81–6.93 (m,2H), 7.15–7.36 (m,7H)

Preparation 78

Boc-MeLeu-D-o-MeOPhLac-MeLeu-D-Lac-OH (0.98 g) was used instead of Boc-MeLeu-D-p-Me$_2$NPhLac-OH, and HCl.H-MeLeu-D-o-MeOPhLac-MeLeu-D-Lac-OBzl (0.94 g) was used instead of HCl.H-MeLeu-D-Lac-OBzl. Except above matter, Boc-MeLeu-D-o-MeOPhLac-MeLeu-D-Lac-MeLeu-D-o-MeOPhLac-MeLeu-D-Lac-OBzl (1.26 g) was obtained according to a similar manner to that of Preparation 26.

NMR (CDCl$_3$,δ): 0.79–1.00 (m,24H),1.19–1.82 (m,2.7H),2.72–3.19 (m,16H), 3.79–3.92 (m,6H),4.61–5.62 (m,10H),6.77–6.93 (m,4H),7.17–7.38 (m,9H)

Preparation 79

Boc-MeLeu-D-o-MeOPhLac-MeLeu-D-Lac-MeLeu-D-o-MeOPhLac-MeLeu-D-Lac-OBzl (1.25g) was used instead of Boc-MeLeu-D-p-Me$_2$NPhLac-OBzl. Except above matter, Boc-MeLeu-D-o-MeOPhLac-MeLeu-D-Lac-MeLeu-D-o-MeOPhLac-MeLeu-D-Lac-OH (1.24 g) was obtained according to a similar manner to that of Preparation 25.

NMR (CDCl$_3$,δ): 0.78–1.00 (m,24H),1.15–1.82 (m,2H), 2.62–3.22 (m,16H), 3.85 (s,6H),4.42–5.90 (m,8H), 6.80–6.92 (m,4H),0.15–7.26 (m,4H)

Preparation 80

3-bromoanisole (2.82 ml) was used instead of 2-bromoanisole. Except above matter, (R)-4-(3-methoxybenzyl)-2,2-dimethyl-1,3-dioxolane (2.25 g) was obtained according to a similar manner to that of Preparation 67.

NMR (CDCl$_3$,δ): 1.36 (s,3H),1.44 (s,3H),2.73 (dd,1H), 3.00 (dd,1H),3.61 (dd,1H),3.79 (s,3H),3.97 (dd,1H),4.32 (dt,1H),6.76–6.82 (m,3H),7.17–7.23 (m,1H)

Preparation 81

(R)-4-(3-methoxybenzyl)-2,2-dimethyl-1,3-dioxolane (1.3 g) was used instead of (R)-4-(2-methoxybenzyl)-2,2-dimethyl-1,3-dioxolane. Except above matter, (R)-3-(3-methoxyphenyl)propane-1,2-diol (1 g) was obtained according to a similar manner to that of Preparation 68.

NMR (CDCl$_3$,δ): 1.93 (t,1H),2.06 (d,1H),2.67–2.82 (m,2H),3.47–3.79 (m,2H),3.81 (s,3H),3.90–4.02 (m,1H), 6.77–6.84 (m,3H),7.20–7.28 (m,1H)

Preparation 82

(R)-3-(3-methoxyphenyl)propane-1,2-diol (0.99 g) was used instead of (R)-3-(2-methoxyphenyl)propane-1,2-diol. Except above matter, (12)-1-t-butyldimethylsiloxy-3-(3-methoxyphenyl)-2-propanol (1.4 g) was obtained according to a similar manner to that of Preparation 69.

NMR (CDCl$_3$,δ): 0.065 (s,6H),0.91 (s,9H),2.40 (d,1H), 2.75 (d,2H),3.45 (dd,1H),3.61 (dd,1H),3.79 (s,3H), 3.85–4.00 (m,1H),6.75–6.83 (m,3H),7.17–7.26 (m,1H)

Preparation 83

(R)-1-t-butyldimethylsiloxy-3-(3-methoxyphenyl)-2-propanol (1.4 g) was used instead of (R)-1-t-butyldimethylsiloxy-3-(2-methoxyphenyl)-2-propanol. Except above matter (R)-1-t-butyldimethylsiloxy-2-methoxymethoxy 3-(3-methoxyphenyl)propane (1.5 g) was obtained according to a similar manner to that of Preparation 70.

NMR (CDCl$_3$,δ): 0.07 (s,6H),0.91 (s,9H),2.71 (dd,1H), 2.89 (dd,1H),3.16 (s,3H),3.53–3.68 (m,2H),3.80 (s,3H), 3.79–3.90 (m,1H),4.51 (d,1H),4.68 (d,1H),6.72–6.85 (m,3H),7.11–7.20 (m,1H)

Preparation 84

(R)-1-t-butyldimethylsiloxy-2-methoxymethoxy-3-(3-methoxyphenyl)propane (1.5 g) was used instead of (R)-1t-butyldimethylsiloxy-2-methoxymethoxy-3-(2-methoxyphenyl)propane. Except above matter, (R)-2-methoxymethoxy-3-(3-methoxyphenyl)-1-propanol (0.93 g) was obtained according to a similar manner to that of Preparation 71.

NMR (CDCl$_3$,δ): 2.69–2.92 (m,2H),3.35 (s,3H), 3.45–3.68 (m,2H),3.79 (s,3H),3.70–3.86 (m,1H),4.57 (d,1H),4.68 (d,1H),6.73–6.83 (m,3H),7.16–7.26 (m,1H)

Preparation 85

(R)-2-methoxymethoxy-3-(3-methoxyphenyl)-1-propanol (0.93 g) was used instead of (R)-2-methoxymethoxy-3-(2-methoxyphenyl)-1-propanol. Except above matter, benzyl (R)-2-hydroxy-3-(3-methoxyphenyl)propionate (0.61 g) was obtained according to a similar manner to that of Preparation 72.

NMR (CDCl$_3$,δ): 2.72 (d,1H),2.95 (dd,1H),3.10 (dd,1H), 3.77 (s,3H),4.41–4.55 (m,1H),5.18 (s,2H),6.71–6.80 (m,3H),7.13–7.39 (m,6H)

Preparation 86

H-D-m-MeOPhLac-OBzl (0.6 g) was used instead of HD-p-Me$_2$NPhLac-OBzl. Except above matter, Boc-MeLeu-D-m-MeOPhLac-OBzl (1.06 g) was obtained according to a similar manner to that of Preparation 24.

NMR (CDCl$_3$,δ): 0.89 (d,6H),1.26–1.57 (m,12H), 2.62–2–2.75 (m,3H),3.02–3.22 (m,2H),3.76 (s,3H), 4.62–5.30 (m,4H),6.73–6.79 (m,3H),7.14–7.34 (m,6H)

Preparation 87

Boc-MeLeu-D-m-MeOPhLac-OBzl (1g) was used instead of Boc-MeLeu-D-p-Me$_2$NPhLac-OBzl. Except above matter, Boc-MeLeu-D-m-MeOPhLac-OH (0.93 g) was obtained according to a similar manner to that of Preparation 25.

NMR (CDCl$_3$,δ): 0.82–0.98 (m,6H),1.30–1.80 (m,12H), 2.64–2.80 (m,3H), 3.03–3.32 (m,2H),3.79 (s,3H),4.42–5.40 (m,2H),6.76–6.84 (m,3H), 7.16–7.26 (m,1H)

Preparation 88

Boc-MeLeu-D-m-MeOPhLac-OH (0.93 g) was used instead of Boc-MeLeu-D-p-Me$_2$NPhLac-OH. Except above matter, Boc-MeLeu-D-m-MeOPhLac-MeLeu-D-Lac-OBzl (1.28 g) was obtained according to a similar manner to that of Preparation 26.

NMR (CDCl$_3$,δ): 0.82–0.99 (m,12H),1.20–1.75 (m,18H), 2.75–2.92 (m,6H), 3.00–3.20 (m,2H),3.78 (s,3H),4.62–5.50 (m,6H),6.76–6.84 (m,3H), 7.17–7.39 (m,6H)

Preparation 89

Boc-MeLeu-D-m-MeOPhLac-MeLeu-D-Lac-OBzl (0.64 g) was used instead of Boc-MeLeu-D-p-Me$_2$NPhLac-OBzl. Except above matter, Boc-MeLeu-D-m-MeOPhLac-MeLeu-D-Lac-OH (0.6 g) was obtained according to a similar manner to that of Preparation 25.

NMR (CDCl$_3$,δ): 0.80–0.98 (m,12H),1.10–1.75 (m,18H), 2.73–3.22 (m,8m), 3.78 (s,3H),4.60–5.85 (m,4H),6.75–6.85 (m,3H),7.18–7.25 (m,1H)

Preparation 90

Boc-MeLeu-D-m-MeOPhLac-MeLeu-D-Lac-OBzl (0.61 g) was used instead of Boc-MeLeu-D-p-Me$_2$NPhLac-MeLeu-D-Lac-OBzl. Except above matter, HCl.H-MeLeu-D-m-MeOPhLac-MeLeu-D-Lac-OBzl (0.6 g) was obtained according to a similar manner to that of Preparation 28.

NMR (CDCl$_3$,δ): 0.62–1.00 (m,12H),1.10–1.98 (m,9H), 2.56–3.10 (m,8H), 3.70–3.82 (m,1H),3.79 (s,3H),5.02–5.59 (m,5H),6.75–6.90 (m,3H), 7.15–7.40 (m,6H)

Preparation 91

Boc-MeLeu-D-m-MeOPhLac-MeLeu-D-Lac-OH (0.6 g) was used instead of Boc-MeLeu-D-p-Me$_2$NPhLac-OH and HCl.H-MeLeu-D-m-MeOPhLac-MeLeu-D-Lac-OBzl (0.6 g) was used instead of HCl.H-MeLeu-D-Lac-OBzl. Except above matter, Boc-MeLeu-D-m-MeOPhLac-MeLeu-D-Lac-MeLeu-D-m-MeOPhLac-MeLeu-D-Lac-OBzl (0.82 g) was obtained according to a similar manner to that of Preparation 26.

NMR (CDCl$_3$,δ): 0.70–1.02 (m,24H),1.20–1.79 (m,2.7H),2.70–3.19 (m,16), 3.78 (s,6H),5.01–5.60 (m,10H), 6.70–6.92 (m,6H),7.18–7.34 (m,7H)

Preparation 92

Boc-MeLeu-D-m-MeOPhLac-MeLeu-D-Lac-MeLeu-D-m-MeOPhLac-MeLeu-D-Lac-OBzl (0.82 g) was used instead of Boc-MeLeu-D-p-Me$_2$NPhLac-OBzl. Except above matter, Boc-MeLeu-D-m-MeOPhLac-MeLeu-D-Lac-MeLeu-D-m-MeOPhLac-MeLeu-D-Lac-OH (0.79 g) was obtained according to a similar manner to that of Preparation 25.

NMR (CDCl$_3$,δ): 0.75–1.00 (m,24H),1.10–1.80 (m,2.7H),2.60–3.19 (m,16H), 3.78 (s,6H),4.58–5.78 (m,8H),6.71–6.90 (m,6H),7.12–7.35 (m,2H)

Preparation 93

1-bromo-3,4-dimethoxybenzene (1.83 g) was used instead of 4-(2-methoxyethoxy) bromobenzene. Except above matter, benzyl (R)-2-hydroxy-3-(3,4-dimethoxyphenyl)propionate (0.23 g) was obtained according to a similar manner to that of Preparation 59.

NMR (CDCl$_3$,δ): 2.71 (d,1H),2.93 (dd,1H),3.08 (dd,1H), 3.79 (s,3H),3.85 (s,3H),4.42–4.55 (m,1H),5.19 (s,2H), 6.65–6.76 (m,3H),7.26–7.40 (m,5H)

Preparation 94

H-D-3,4-DMOPhLac-OBzl (0.23 g) was used instead of H-D-p-Me$_2$NPhLac-OBzl. Except above matter, Boc-MeLeu-D-3,4-DMOPhLac-OBzl (0.34 g) was obtained according to a similar manner to that of Preparation 24.

NMR (CDCl$_3$,δ): 0.89 (d,6H),1.39–1.62 (m,12H), 2.62–2.73 (m,3H),3.0–3.19 (m,2H),3.82 (s,3H),3.85 (s,3H), 4.62–5.32 (m,4H),6.65–6.80 (m,3H), 7.20–7.40 (m,5H)

Preparation 95

Boc-MeLeu-D-3,4-DMOPhLac-OBzl (0.34 g) was used instead of Boc-MeLeu-D-p-Me$_2$NPhLac-OBzl. Except above matter, Boc-MeLeu-D-3,4-DMOPhLac-OH (0.3 g) was obtained according to a similar manner to that of Preparation 25.

NMR (CDCl$_3$,δ): 0.85–0.96 (m,6H),1.42 (s,9H), 1.22–1.69 (m,3H),2.73–2.82 (m,3H),2.95–3.22 (m,2H),3.85 (s,3H),3.87 (s,3H),4.38–4.70 (m,1H), 5.21–5.39 (m,1H), 6.72–6.83 (m,3H)

Preparation 96

Boc-MeLeu-D-3,4-DMOPhLac-OH (0.3 g) was used instead of Boc-MeLeu-D-p-Me₂NPhLac-OH. Except above matter, Boc-MeLeu-D-3,4-DMOPhLac-MeLeu-D-Lac-OBzl (0.41 g) was obtained according to a similar manner to that of
Preparation 26.

NMR (CDCl$_3$,δ): 0.82–0.98 (m,12H),1.35–1.69 (m,18H), 2.77–3.15 (m,8H), 3.85 (s,3H),3.87 (s,3H),4.62–5.48 (m,6H),6.72–6.80 (m,3H),7.26–7.39 (m,5H)

Preparation 97

Boc-MeLeu-D-3,4-DMOPhLac-MeLeu-D-Lac-OBzl (0.2 g) was used instead of Boc-MeLeu-D-p-Me₂NPhLac-OBzl. Except above matter, Boc-MeLeu-D-3,4-DMOPhLac-MeLeu-D-Lac-OH (0.2 g) was obtained according to a similar manner to that of Preparation 25.

NMR (CDCl$_3$,δ): 0.79–1.00 (m,12H),1.24–1.80 (m,18H), 2.74–3.16 (m,8H), 3.85 (s,3H),3.87 (s,3H),4.59–5.78 (m,4H),6.77 (s,3H)

Preparation 98

Boc-MeLeu-D-3,4-DMOPhLac-MeLeu-D-Lac-OBzl (0.2 g) was used instead of Boc-MeLeu-D-p-Me₂NPhLac-MeLeu-D-Lac-OBzl. Except above matter, HCl.H-MeLeu-D-3,4-DMOPhLac-MeLeu-D-Lac-OBzl (0.18 g) was obtained according to a similar manner to that of Preparation 28.

NMR (CDCl$_3$,δ): 0.78–0.98 (m,12H),1.20–2.00 (m,9H), 2.62–3.15 (m,8H), 3.69–3.82 (m,1H),3.85 (s,3H),3.87 (s,3H),5.02–5.60 (m,5H),6.74–6.82 (m,3H),7.22–7.38 (m,5H)

Preparation 99

Boc-MeLeu-D-3,4-DMOPhLac-MeLeu-D-Lac-OH (0.2 g) was used instead of Boc-MeLeu-D-p-Me₂NPhLac-OH, and HCl.H-MeLeu-D-3,4-DMOPhLac-MeLeu-D-Lac-OBzl (0.18 g) was used instead of HCl.H-MeLeu-D-Lac-OBzl. Except above matter, Boc-MeLeu-D-3,4-DMOPhLac-MeLeu-D-Lac-MeLeu-D-3,4-DMOPhLac-MeLeu-D-Lac-OBzl (0.27 g) was obtained according to a similar manner to that of Preparation 26.

NMR (CDCl$_3$,δ): 0.70–1.00 (m,24H),1.20–1.79 (m,2.7H),2.72–3.18 (m,16H), 3.84 (s,6H),3.86 (s,6H), 4.62–5.48 (m,10H),6.72–6.83 (m,6H),7.21–7.40 (m,5H)

Preparation 100

Boc-MeLeu-D-3,4-DMOPhLac-MeLeu-D-Lac-MeLeu-D-3,4-DMOPhLac-MeLeu-D-Lac-OBzl (0.26 g) was used instead of Boc-MeLeu-D-p-Me₂NPhLac-OBzl. Except above matter, Boc-MeLeu-D-3,4-DMOPhLac-MeLeu-D-Lac-MeLeu-D-3,4-DMOPhLac-MeLeu-D-Lac-OH (0.26 g) was obtained according to a similar manner to that of Preparation 25.

NMR (CDCl$_3$,δ): 0.76–1.02 (m,24H),1.32–1.75 (m,2.7H),2.72–3.20 (m,16H), 3.85 (s,6H),3.87 (s,6H), 4.60–5.70 (m,8H),6.72–6.80 (m,6H)

Preparation 101

1-bromo-2,4-dimethoxybenzene (2.93 g) was used instead of 4-(2-methoxyethoxy)bromobenzene. Except above matter, benzyl (R)-2-hydroxy-3-(2,4-dimethoxyphenyl)propionate (1.28 g) was obtained according to a similar manner to that of
Preparation 59.

NMR (CDCl$_3$,δ): 2.87 (d,1H),2.96 (dd,1H),3.10 (dd,1H), 3.76 (s,3H),3.78 (s,3H),4.43–4.53 (m,1H),5.12 (d,1H),5.19 (d,1H),6.36–6.43 (m,2H),6.99 (d,1H),7.21–7.40 (m,5H)

Preparation 102

H-D-2,4-DMOPhLac-OBzl (1.27 g) was used instead of H-D-p-Me₂NPhLac-OBzl. Except above matter, Boc-MeLeu-D-2,4-DMOPhLac-OBzl (2.16 g) was obtained according to a similar manner to that of Preparation 24.

NMR (CDCl$_3$,δ): 0.89 (d,6H),1.36–1.60 (m,12H), 2.61–2.70 (m,3H),2.92–3.29 (m,2H),3.76 (s,3H),3.77 (s,3H),4.60–5.35 (m,4H),6.31–16.40 (m, 2H),6.97 (d,1H), 7.19–7.40 (m,5H)

Preparation 103

Boc-MeLeu-D-2,4-DMOPhLac-OBzl (2.15 g) was used instead of Boc-MeLeu-D-p-Me₂NPhLac-OBzl. Except above matter, Boc-MeLeu-D-2,4-DMOPhLac-OH (1.61 g) was obtained according to a similar manner to that of Preparation 25.

NMR (CDCl$_3$,δ): 0.82–0.93 (m,6H),1.38–1.62 (m,12H), 2.73 (brs,3H), 2.91–3.39 (m,2H),3.78 (s,6H),4.58–4.70 (m,1H),5.20–5.39 (m,1H),6.37–6.44 (m,2H),7.03 (d,1H)

Preparation 104

Boc-MeLeu-D-2,4-DMOPhLac-OH (1.6 g) was used instead of Boc-MeLeu-D-p-Me₂NPhLac-OH. Except above matter, Boc-MeLeu-D-2,4-DMOPhLac-MeLeu-D-Lac-OBzl (2.2 g) was obtained according to a similar manner to that of Preparation 26.

NMR (CDCl$_3$,δ): 0.80–1.05 (m,12H),1.32–1.65 (m,18H), 2.75–3.15 (m,8H), 3.78 (s,3H),3.81 (s,3H),4.60–5.60 (m,6H),6.30–6.46 (m,2H),7.00–7.09 (m,1H),7.25–7.40 (m,5H)

Preparation 105

Boc-MeLeu-D-2,4-DMOPhLac-MeLeu-D-Lac-OBzl (1.1 g) was used instead of Boc-MeLeu-D-p-Me₂NPhLac-OBzl. Except above matter, Boc-MeLeu-D-2,4-DMOPhLac-MeLeu-D-Lac-OH (1 g) was obtained according to a similar manner to that of Preparation 25.

NMR (CDCl$_3$,δ): 0.80–1.00 (m,12H),1.15–1.78 (m,18H), 2.70–3.12 (m,8H), 3.78 (s,3H),3.83 (s,3H),4.60–5.87 (m,4H),6.30–6.42 (m,2H),7.04 (d,1H)

Preparation 106

Boc-MeLeu-D-2,4-DMOPhLac-MeLeu-D-Lac-OBzl (1 g) was used instead of Boc-MeLeu-D-p-Me₂NPhLac-MeLeu-D-Lac-OBzl. Except above matter, HCl.H-MeLeu-D-2,4-DMOPhLac-MeLeu-D-Lac-OBzl (0.98 g) was obtained according to a similar manner to that of Preparation 28.

NMR (CDCl$_3$,δ): 0.69–1.02 (m,12H),1.20–2.00 (m,9H), 2.58–3.20 (m,8H), 3.70–3.80 (m,1H),3.78 (s,3H),3.81 (s,3H),5.00–5.71 (m,5H),6.37–6.46 (m,2H),7.07 (d,1H), 7.20–7.42 (m,5H)

Preparation 107

Boc-MeLeu-D-2,4-DMOPhLac-MeLeu-D-Lac-OH (1 g) was used instead of Boc-MeLeu-D-p-Me₂NPhLac-OH, and HCl.H-MeLeu-D-2,4-DMOPhLac-MeLeu-D-Lac-OBzl (0.98 g) was used instead of HCl.H-MeLeu-D-Lac-OBzl. Except above matter, Boc-MeLeu-D-2,4-DMOPhLac-MeLeu-D-Lac-MeLeu-D-2,4-DMOPhLac-MeLeu-D-Lac-OBzl (1.48 g) was obtained according to a similar manner to that of Preparation 26.

NMR (CDCl$_3$,δ): 0.82–1.00 (m,24H),1.15–1.80 (m,2.7H),2.75–3.21 (m,16H), 3.72–3.84 (m,12H),4.60–5.60 (m,10H),6.31–6.49 (m,4H),7.00–7.17 (m,2H),7.21–7.40 (m,5H)

Preparation 108

Boc-MeLeu-D-2,4-DMOPhLac-MeLeu-D-Lac-MeLeu-D-2,4-DMOPhLac-MeLeu-D-Lac-OBzl (1.45 g) was used instead of Boc-MeLeu-D-p-Me₂NPhLac-OBzl. Except above matter, Boc-MeLeu-D-2,4-DMOPhLac-MeLeu-D-Lac-MeLeu-D-2,4-DMOPhLac-MeLeu-D-Lac-OH (1.49 g) was obtained according to a similar manner to that of Preparation 25.

NMR (CDCl$_3$,δd): 0.80–1.02 (m,24H),1.20–1.90 (m,2.7H),2.71–3.22 (m,16H), 3.81 (s) and 3.78 (s) (12H), 4.60–5.80 (m,8H),6.33–6.46 (m,4H), 7.01–7.15 (m,2H)

Preparation 109

1-bromo-3,4-methylenedioxybenzene (2.05 ml) was used instead of 2-bromoanisole. Except above matter, (R)-4-(3,4-methylenedioxybenzyl)-2,2-dimethyl-1,3-dioxolane (1.64 g) was obtained according to a similar manner to that of Preparation 67.

NMR (CDCl₃,δ): 1.35 (s,3H),1.43 (s,3H),2.69 (dd,1H), 2.91 (dd,1H),3.62 (dd,1H),3.97 (dd,1H),4.27 (dt,1H),5.93 (s,2H),6.58–6.78 (m,3H)

Preparation 110

(R)-2,2-dimethyl-5-(3,4-methylenedioxybenzyl)-1,3-dioxolane (1.63 g) was used instead of (R)-2,2-dimethyl-5-(2-methoxybenzyl)-1,3-dioxolane. Except above matter, (R)-3-(3,4-methylenedioxyphenyl)propane-1,2-diol (1.37 g) was obtained according to a similar manner to that of Preparation 68.

NMR (CDCl₃,δ): 2.63 (dd,1H),2.72 (dd,1H),3.48 (dd, 1H),3.67 (dd,1H), 3.80–3.96 (m,1H),5.92 (s,2H),6.58–6.78 (m,3H)

Preparation 111

(R)-3-(3,4-methylenedioxyphenyl)-propane-1,2-diol (1.25 g) was used instead of (R)-3-(2-methoxyphenyl)propane-1,2-diol. Except above matter, (R)-1-t-butyldimethylsiloxy-3-(3,4-methylenedioxyphenyl)-2-propanol (1.77 g) was obtained according to a similar manner to that of Preparation 69.

NMR (CDCl₃,δ): 0.07 (s,6H),0.91 (s,9H),2.69 (d,2H), 3.46 (dd,1H),3.61 (dd,1H),3.79–3.85 (m,1H),5.93 (s,2H), 6.63–6.77 (m,3H)

Preparation 112

(R)-1-t-butyldimethylsiloxy-3-(3,4-methylenedioxyphenyl)-2-propanol (1.77 g) was used instead of (R)-1-t-butyldimethylsiloxy-3-(2-methoxyphenyl)-2-propanol. Except above matter, (R)-1-t-butyldimethylsiloxy-2-methoxymethoxy-3-(3,4-methylenedioxyphenyl)propane (1.79 g) was obtained according to a similar manner to that of Preparation 70.

NMR (CDCl₃,δ): 0.07 (s,6H),0.90 (s,9H),2.65 (dd,1H), 2.83 (dd,1H),3.20 (s,3H),3.52–3.62 (m,2H),3.71–3.83 (m,1H),4.52 (d,1H),4.68 (d,1H),5.92 (s,2H),6.64–6.75 (m,3H)

Preparation 113

(R)-1-t-butyldimethylsiloxy-3-(3,4-methylenedioxyphenyl)-2-methoxymethoxypropane (1.77 g) was used instead of (R)-1-t-butyldimethylsiloxy-3-(2-methoxyphenyl)-2-methoxymethoxypropane. Except above matter, (R)-2-methoxymethoxy-3-(3,4-methylenedioxyphenyl)-1-propanol (1.17 g) was obtained according to a similar manner to that of Preparation 71.

NMR (CDCl₃,δ): 2.69 (dd,1H),2.79 (dd,1H),3.37 (s,3H), 3.49 (dd,1H),3.63 (dd,1H),3.71–3.82 (m,1H),4.58 (d,1H), 4.68 (d,1H),5.93 (s,2H),6.62–6.78 (m,3H)

Preparation 114

(R)-2-methoxymethoxy-3-(3,4-methylenedioxyphenyl)-1-propanol (0.92 g) was used instead of (R)-2-methoxymethoxy-3-(2-methoxyphenyl)-1-propanol. Except above matter, benzyl (R)-2-hydroxy-3-(3,4-methylenedioxyphenyl)propionate (0.33 g) was obtained according to a similar manner to that of Preparation 72.

NMR (CDCl₃,δ): 2.72 (d,1H),2.88 (dd,1H),3.04 (dd,1H), 4.38–4.55 (m,1H), 5.19 (s,2H),5.92 (s,2H),6.53–6.70 (m,3H),7.25–7.40 (m,5H)

Preparation 115

H-D-3,4-MODPhLac-OBzl (0.5 g) was used instead of H-D-p-Me₂NPhLac-OBzl. Except above matter, Boc-MeLeu-D-3,4-MODPhLac-OBzl (0.74 g) was obtained according to a similar manner to that of Preparation 24.

NMR (CDCl₃,δ): 0.91 (d,6H),1.38–1.70 (m,12H), 2.62–2.83 (m,3H),2.98–3.20 (m,2H),4.55–5.26 (m,4H),5.92 (s,2H),6.52–6.75 (m,3H),7.21–7.40 (m,5H)

Preparation 116

Boc-MeLeu-D-3,4-MODPhLac-OBzl (0.73 g) was used instead of Boc-MeLeu-D-p-Me₂NPhLac-OBzl. Except above matter, Boc-MeLeu-D-3,4-MODPhLac-OH (0.63 g) was obtained according to a similar manner to that of Preparation 25.

NMR (CDCl₃,δ): 0.80–1.00 (m,6H),1.20–1.80 (m,12H), 2.63–2.93 (m,3H), 2.95–3.25 (m,2H),4.43–4.90 (m,1H), 5.09–5.36 (m,1H),5.93 (s,2H),6.60–6.82 (m,3H)

Preparation 117

Boc-MeLeu-D-3,4-MODPhLac-OH (0.63 g) was used instead of Boc-MeLeu-D-p-Me₂NPhLac-OH. Except above matter, Boc-MeLeu-D-3,4-MODPhLac-MeLeu-D-Lac-OBzl (0.85 g) was obtained according to a similar manner to that of Preparation 26.

NMR (CDCl₃,δ): 0.80–1.00 (m,12H),1.20–1.82 (m,18H), 2.69–3.06 (m,8H), 4.60–5.60 (m,6H),5.88–5.97 (m,2H), 6.68–6.80 (m,3H),7.26–7.40 (m,5H)

Preparation 118

Boc-MeLeu-D-3,4-MODPhLac-MeLeu-D-Lac-OBzl (0.42 g) was used instead of Boc-MeLeu-D-p-Me₂NPhLac-OBzl. Except above matter, Boc-MeLeu-D-3,4-MODPhLac-MeLeu-D-Lac-OH (0.393)was obtained according to a similar manner to that of Preparation 25.

NMR (CDCl₃,δ): 0.80–1.00 (m,12H),1.20–1.80 (m,18H), 2.65–3.20 (m,8H), 4.60–5.80 (m,4H),5.93 (s,2H),6.62–6.78 (m,3H)

Preparation 119

Boc-MeLeu-D-3,4-MODPhLac-MeLeu-D-Lac-OBzl (0.43 g) was used instead of Boc-MeLeu-D-p-Me₂NPhLac-MeLeu-D-Lac-OBz. Except above matter, HCl.H-MeLeu-D-3,4-MODPhLac-MeLeu-D-Lac-OBzl (0.4 g) was obtained according to a similar manner to that of Preparation 28.

NMR (CDCl₃,δ):0.78–1.05 (m,12H),1.20–2.40 (m,9H), 2.60–3.25 (m,8H), 3.60–3.90 (m,1H),5.02–5.58 (m,5H), 5.85–5.98 (m,2H),6.65–6.92 (m,3H),7.20–7.42 (m,5H)

Preparation 120

Boc-MeLeu-D-3,4-MODPhLac-MeLeu-D-Lac-OH (0.39 g) was used instead of Boc-MeLeu-D-p-Me₂NPhLac-OH, and HCl.H-MeLeu-D-3,4-MODPhLac-MeLeu-D-Lac-OBzl (0.4 g) was used instead of HCl.H-MeLeu-D-Lac-OBz. Except above matter. Boc-MeLeu-D-3,4-MODPhLac-MeLeu-D-Lac-MeLeu-D-3,4-MODPhLac-MeLeu-D-Lac-OBzl (0.59 g) was obtained according to a similar manner to that of Preparation 26.

NMR (CDCl₃,δ): 0.75–1.05 (m,24H),1.15–1.90 (m,2.7H),2.62–3.15 (m,16H), 4.60–5.60 (m,10H),5.85–5.96 (m,4H),6.60–6.80 (m,6H),7.26–7.40 (m,5H)

Preparation 121

Boc-MeLeu-D-3,4-MODPhLac-MeLeu-D-Lac-MeLeu-D-3,4-MODPhLac-MeLeu-D-Lac-OBzl (0.59 g) was used instead of Boc-MeLeu-D-p-Me₂NPhLac-OBz. Except above matter, Boc-MeLeu-D-3,4-MODPhLac-MeLeu-D-Lac-MeLeu-D-3,4-MODPhLac-MeLeu-D-Lac-OH (0.59 g) was obtained according to a similar manner to that of Preparation 25.

NMR (CDCl₃,δ): 0.75–1.00 (m,24H),1.15–1.82 (m,2.7H),2.62–3.20 (m,16H), 4.56–5.63 (m,8H),5.92 (s,4H),6.60–6.80 (m,6H)

Preparation 122

To a solution of 3-nitro-L-tyrosine (4.52 g) in dioxane (40 ml) was added 1N sodium hydroxide solution (40 ml), and further di-t-butyldicarbonate (4.8 g) was added and stirred for 1 hour at room temperature. To the reaction was added water (200 ml) and extracted with ethyl acetate (100 ml×3).

After the ethyl acetate layer was washed with saturated sodium chloride, dried over anhydrous sodium sulfate, and the solvent was evaporated in vacuo. To the residue was added hexane and ether and it was crystallized to give N-(t-butoxycarbonyl)-3-nitro-L-tyrosine (6.50 g).

NMR (CDCl$_3$,δ):1.42 (s,9H),2.9–3.3 (m,3H),4.6–4.65 (m) and 5.05 –5.15 (m) (1H),7.09 (d,1H),7.44 (dd,1H),7.93 (d,1H),10.4–10.6 (m,1H)

IR (KBr): 1713,1683 cm$^{-1}$

Preparation 123

To a solution of N-(t-butoxycarbonyl)-3-nitro-L-tyrosine (6.49 g) in dimethylformamide (50 ml) was added potassium carbonate (11.05 g). Further methyl iodide (3.7 ml) was added and stirred for 15 hours at room temperature. To the reaction solution was added water (500 ml) and extracted with ethyl acetate (100 ml×3). After ethyl acetate layer was washed with saturated brine, the residue was dried over anhydrous sodium sulfate. The solvent was evaporated in vacuo. To the residue was added hexane and ether and it was crystallized to give methyl N-(t-butoxycarbonyl)-O-methyl-3-nitro-L-tyrosine (6.76 g).

NMR (CDCl$_3$,δ): 1.42 (s,9H),3.00 (dd,1H)),3.17 (dd,1H), 3.75 (s,3H),3.95 (s,3H),4.5–4.65 (m) and 5.0–5.1 (m) (1H), 7.02 (d,1H),7.33 (dd,1H),7.62 (d,1H)

IR (KBr): 1742,1710,1695 cm$^{-1}$

Preparation 124

To a ethanol solution of methyl N-(t-butoxycarbonyl)-O-methyl-3-nitro-L-tyrosine (6.74 g) was added 1N sodium hydroxide solution (25 ml) and was stirred for 2 hours at room temperature. The solvent was evaporated and water (70 ml) and 1N hydrochloric acid solution (27.5 ml) was added, extracted with ethyl acetate (50 ml×3). After ethyl acetate layer was washed with saturated brine, the residue was dried over anhydrous sodium sulfate. The solvent was evaporated in vacuo. To the residue was added hexane and ether and it was crystallized to give N-(t-butoxycarbonyl)-O-methyl-3-nitro-L-tyrosine (6.61 g).

NMR (CDCl$_3$,δ): 1.42 (s,9H),2.9–3.3 (m,2H),3.95 (s,3H), 4.5–4.65 (m) and 5.0–5.1 (m) (1H),7.27 (d,1H),7.39 (dd, 1H)),7.69(bs,1H)

IR (KBr): 1727,1652 cm$^{-1}$

Preparation 125

To N-(t-butoxycarbonyl)-O-methyl-3-nitro-L-tyrosine (6.60 g) was added 4N hydrogen chloride in ethyl acetate solution and was stirred for 1 hour at room temperature. The solvent was evaporated and further it was azeotroped by toluene to give O-methyl-3-nitro-L-tyrosine hydrochloride (4.95 g).

NMR (DMSO-d$_6$,δ): 3.1–3.2 (m,2H),3.92 (s,3H),4.21 (t,1H),7.35 (d,1H), 7.59 (dd,1H),7.83 (d,1H)

IR (KBr): 1729 cm$^{-1}$

Preparation 126

To suspension solution of O-methyl-3-nitro-L-tyrosine.hydrochloride (4.93 g) in 6N aqueous hydrochloric acid was added under ice-cooling, sodium nitrite (1.97 g) and was stirred at the same temperature for 1 and ½ hour and further at room temperature for 3 hours. The resultant suspension solution was extracted with ethyl acetate (50 ml×3). After the ethyl acetate layer was washed with saturated brine, dried over anhydrous sodium sulfate. The solvent was evaporated in vacuo to give (S)-2-chloro-3-(4-methoxy-3-nitrophenyl)propionic acid (4.46 g).

NMR (CDCl$_3$,δ): 3.21 (dd,1H),3.39 (dd,1H),3.96 (s,3H), 4.49 (dd,1H) 7.06 (d,1H),7.45 (dd,1H),7.77 (d,1H)

IR (neat): 1726 cm$^{-1}$

Preparation 127

To a ethanol solution of (S)-2-chloro-3-(4-methoxy-3-nitrophenyl)propionic acid (4.46 g) was added p toluene-sulfonic acid (0.38 g) and heated under reflux for 5 hours. After cooled it down, the solvent was evaporated in vacuo. The resultant suspension solution was extracted by ethyl acetate (50 ml×3). After the ethyl acetate layer was washed with saturated brine, dried over anhydrous sodium sulfate. The solvent was evaporated in vacuo, the resultant crude product was purified by silica gel column chromatography, and eluted with mixture of hexane or ethyl acetate (4:1, v/v). The fractions containing the desired product were combined and evaporated in vacuo to obtain ethyl (S)-2-chloro-3-(4-methoxy-3-nitrophenyl)propionate (4.51 g)

NMR (CDCl$_3$,δ): 1.26 (t,3H),3.17 (dd,1H),3.36 (dd,1H)), 3.96 (s,3H),4.15 (q,2H),4.41 (dd,1H) 7.03 (d,1H),7.43 (dd, 1H),7.74 (d,1H)

IR (neat): 1735 cm$^{-1}$

Preparation 128

To a ethanol solution (50 ml) which contain acetic acid (2.3 ml) was added cesium carbonate (6.5 g) and stirred for a half an hour at room temperature, and the solvent was evaporated to give cesium acetate. Cesium acetate was added to dimethylformamide solution of ethyl (S)-2-chloro-3-(4-methoxy-3-nitrophenyl)propionate (4.51 g) and stirred for 4 hours. To the mixture, water (200 ml) was added and extracted with ether (100 ml×1, 50 ml×2). After ether layer was washed with saturated brine, the residue was dried over anhydrous sodium sulfate and evaporated in vacuo. The resultant crude product was purified by silica gel column chromatography, eluting with a mixed solvent of hexane and ethyl acetate (7:3, v/v). The fractions containing the desired product were combined and evaporated in vacuo to obtain ethyl (R)-2-acetoxy-3-(4-methoxy-3-nitrophenyl)propionate (1.58 g).

NMR (CDCl$_3$,δ): 1.26 (t,3H),2.11 (s,3H),3.05–3.25 (m,2H),3.95 (s,3H), 4.20 (q,2H),5.19 (dd,1H) 7.03 (d,1H), 7.42 (dd,1H),7.74 (d,1H)

IR (neat): 1742 cm$^{-1}$

Preparation 129

To a ethanol solution (50 ml) which contain 37% aqueous formalin solution (4.0 ml) of ethyl (R)-2-acetoxy-3-(4-methoxy-3-nitrophenyl)propionate (1.56 g) was added 10% palladium on carbon (0.5 g) and under atmospheric pressure hydrogenated at room temperature for 4 hours. The catalyst was filtered off and the solvent was evaporated in vacuo. The resultant crude product was purified by silica gel column chromatography, eluting with a mixed solvent of hexane and ethyl acetate (7:3, v/v). The fractions containing the desired product were combined and evaporated in vacuo to obtain ethyl (R)-2-acetoxy-3-(4-methoxy-3-dimethylaminophenyl)propionate (1.58 g).

NMR (CDCl$_3$,δ): 1.23 (t,3H),2.09 (s,3H),2.77 (s,6H), 2.95–3.15 (m,2H), 3.87 (s,3H),4.18 (q,2H),5.15 (dd,1H) 6.75–6.9 (m,3H)

IR (neat): 1742 cm$^{-1}$

Preparation 130

To a solution of ethyl (R)-2-acetoxy-3-(4-methoxy-3-dimethylaminophenyl)propionate (1.56 g) in benzyl alcohol (3.7 ml) and benzene (7.4 ml) was added p-toluenesulfonic acid (0.82 g) and heated under reflux for 6 hours. After cooling, the solvent was evaporated in vacuo, and the gained crude product was purified by silica gel column chromatography. The residue was eluted with mixed solvent of hexane, ethyl acetate, and ethanol (60:35:5, v/v). The fractions containing the desired product were combined and evaporated in vacuo to obtain benzyl (R)-2-hydroxy-3-(4-methoxy-3-dimethylaminophenyl)propionate (0.93 g).

NMR (CDCl$_3$,δ): 2.68 (d,1H),2.74 (s,6H),2.92 (dd,1H), 5.19 (s,2H) 6.7–6.8 (m,3H),7.3–7.4 (m,5H)

IR (KBr): 1738 cm⁻¹

Preparation 131

H-D-3MA-4MOPhLac-OBzl (0.90 g) was used instead of H-D-p-Me₂NPhLac-OBz. Except above matter, Boc-Me-Leu-D-3MA-4MOPhLac-MeLeu-D-Lac-OBzl (1.40 g) was obtained according to a similar manner to that of Preparation 24.

NMR (CDCl₃,δ): 0.89 (d,6H),1.41 (s) and 1.47 (s) (9H), 1.4–1.6 (m,3H), 2.65 (s) and 2.68 (s) (3H),2.75 (s,6H), 3.1–3.2 (m,2H),3.85 (s,3H),4.6–4.75 (m) and 4.95–5.3 (m) (4H),6.7–6.8 (m,3H),7.2–7.4 (m,5H)

IR (KBr): 1741,1695 cm⁻¹

Preparation 132

Boc-MeLeu-D-3MA-4MOPhLac-OBzl (1.38 g) was used instead of Boc-MeLeu-D-p-Me₂NPhLac-OBz. Except above matter, Boc-MeLeu-D-3MA-4MOPhLac-OH (1.16 g) was obtained according to a similar manner to that of Preparation 25., IR (KBr): 1740,1694 cm⁻¹

Preparation 133

Boc-MeLeu-D-3MA-4MOPhLac-OH (1.16 g) was used instead of Boc-MeLeu-D-p-Me₂NPhLac-OH. Except above matter, Boc-MeLeu-D-3MA-4MOPhLac-MeLeu-D-Lac-OBzl (1.80 g) was obtained according to a similar manner to that of Preparation 26.

NMR (CDCl₃,δ): 0.8–1.1 (m,12H),1.35–1.7 (m,18H), 2.65–3.1 (m,12H), 3.0–3.1 (m,2H),3.85 (s,3H),4.60–3.8 (m) and 4.9–5.5 (m) (6H), 6.7–6.85 (m,3H),7.3–7.4 (m,5H)

IR (KBr): 1740,1694,1664 cm⁻¹

Preparation 134

Boc-MeLeu-D-3MA-4MOPhLac-MeLeu-D-Lac-OBzl (0.90 g) was used instead of Boc-MeLeu-D-p-Me₂NPhLac-OBzl. Except above matter, Boc-MeLeu-D-3MA-4MOPhLac-MeLeu-D-Lac-OH (0.85 g) was obtained according to a similar manner to that of Preparation 25.

IR (KBr): 1740,1696,1662 cm⁻¹

Preparation 135

Boc-MeLeu-D-3MA-4MOPhLac-MeLeu-D-Lac-OBzl (0.90 g) was used instead of Boc-MeLeu-D-p-Me₂NPhLac MeLeu-D-Lac-OBzl. Except above matter, 2HCl.H-MeLeu-D-MA-4MOPhLac-MeLeu-D-Lac-OBzl (0.97 g) was obtained according to a similar manner to that of Preparation 28.

IR (KBr): 1744,1648 cm⁻¹

Preparation 136

Boc-MeLeu-D-3MA-4MOPhLac-MeLeu-D-Lac-OH (0.84 g) was used instead of Boc-MeLeu-D-p-Me₂NPhLac-OH, and 2HCl.H-MeLeu-D-3MA-4MOPhLac-MeLeu-D-Lac-OBzl (0.96 g) was used instead of HCl.H-MeLeu-D-Lac-OBzl. Except above matter, Boc-MeLeu-D-3MA-4MOPhLac-MeLeu-D-Lac-MeLeu-D-3MA-4MOPhLac-MeLeu-D-Lac-OBzl (1.15 g) was obtained according to a similar manner to that of Preparation 26.

NMR (CDCl₃,δ): 0.75–1.05 (m,24H),1.3–1.8 (m,2.7H), 2.6–3.2 (m,16H), 2.77 (s,12H),3.85 (s,6H),4.65–4.75 (m) and 4.9–5.5 (m) (10H),6.7–6.9 (m,6H),7.3–7.4 (m,5H)

IR (KBr): 1740,1694,1663 cm⁻¹

FAB-MS: 1303 [M+H]⁺

Preparation 137

Boc-MeLeu-D-3MA-4MOPhLac-MeLeu-D-Lac MeLeu-D-3MA-4MOPhLac-MeLeu-D-Lac-OBzl (1.14 g) was used instead of Boc-MeLeu-D-p-Me₂NPhLac-OBzl. Except above matter, Boc-MeLeu-D-3MA-4MOPhLac-MeLeu-D-Lac-MeLeu-D-3MA-4MOPhLac-MeLeu-D-Lac-OH (1.09 g) was obtained according to a similar manner to that of Preparation 25.

IR (KBr): 1740,1694,1663 cm⁻¹

Preparation 138

Boc-MeLeu-D-3MA-4MOPhLac-MeLeu-D-Lac MeLeu-D-3MA-4MOPhLac-MeLeu-D-Lac-OH (1.08 g) was used instead of Boc-MeLeu-D-p-Me₂NPhLac-MeLeu-D-Lac-OBzl. Except above matter, 3HCl.H-MeLeu-D-3MA-4MOPhLac-MeLeu-D-Lac-MeLeu-D-3MA-4MOPhLac-MeLeu-D-Lac-OH (1.19 g) was obtained according to a similar manner to that of Preparation 28.

IR (KBr): 1741,1646 cm⁻¹

Preparation 139

To a dichloromethane solution of ethyl D-2-hydroxy-3-(4-aminophenyl)propionate (4.2 g) were added under ice-cooling, triethylamine (7.36 ml), acetyl chloride (2.5 g) at room temperature for 2 and ½ hours. The reaction solution was poured into aqueous saturated sodium bicarbonate solution, and extracted with dichloromethane. After drying by magnesium sulfate, the solvent was evaporated in vacuo and then purified by silica gel column chromatography, eluting with a mixed solvent of hexane and ethyl acetate (1:1, v/v). The fractions containing the desired product were combined and evaporated in vacuo to obtain ethyl (R)-3-(4-acetamidephenyl)-2-acetoxypropionate (3.42 g).

NMR (CDCl₃,δ): 1.24 (t,3H),2.08 (s,3H),2.16 (s,3H), 3.06–3.20 (m,2H), 4.17 (q,2H),5.12–5.20 (m,1H),7.17 (d,2H),7.43 (d,2H)

Preparation 140

To an anhydrous acetic acid solution of ethyl (R)-3-(4-acetamidephenyl)-2-acetoxypropionate (3.12 g) was added dropwise under ice-cooling, fuming nitric acid (3 ml)—acetic anhydride (7.5 ml), and stirred for a half an hour successively. The reaction solution was poured into aqueous saturated sodium bicarbonate solution, after the neutralization, extracted with ethyl acetate, and washed with saturated brine. After drying by magnesium sulfate, the solvent was evaporated in vacuo to give ethyl (R)-3-(4-acetamide-3-nitrophenyl)-2-acetoxypropionate (3.98 g)

NMR (CDCl₃,δ): 1.25 (t,3H),2.11 (s,3H),2.29 (s,3H), 3.10–3.25 (m,2H), 4.50 (q,2H),5.17–5.24 (m,1H),7.52 (dd, 1H),8.10 (d,1H),8.72 (d,1H)

Preparation 141

To a solution of ethyl (R)-3-(4-acetamide-3-nitrophenyl)-2-acetoxypropionate (3.9 g) in ethanol (120 ml) was added concentrated hydrochloric acid and heated under reflux for 75 minutes. After ethanol was evaporated in vacuo, aqueous saturated sodium bicarbonate solution was added, extracted with ethyl acetate, and washed with saturated sodium chloride. After drying by magnesium sulfate, the solvent was evaporated in vacuo to give ethyl (R)-3-(4-amino-3-nitrophenyl)-2-hydroxypropionate (2.59 g).

NMR (CDCl₃,δ): 1.32 (t,3H),2.89 (dd,1H),3.05 (dd,1H), 4.23 (q,2H),4.35–4.50 (m,1H),6.74 (d,1H),7.30 (dd,1H)), 7.30 (d,1H)

Preparation 142

To a solution of ethyl (R)-3-(4-amino-3-nitrophenyl)-2-hydroxypropionate (0.8 g) in methanol (8 ml) and water (5 ml) were added iron powder (1 g), acetic acid (0.8 ml) and heated under reflux for a half an hour. After the reaction solution was filtered through celite, methanol was evaporated in vacuo. After the residue was neutralized with aqueous sodium bicarbonate solution, the residue was extracted with ethyl acetate. After drying by magnesium sulfate, the solvent was evaporated in vacuo, and dissolved in acetic acid. To the mixture paraformaldehyde (0.56 g), and sodium cyanoborohydride (0.59 g) were added and stirred for 19 hours at room temperature. The reaction solution was added to aqueous solution saturated with sodium bicarbonate, and after the residue was neutralized with aqueous sodium bicarbonate solution, extracted with ethyl acetate, and dried over sodium sulfate. The solvent was evaporated in vacuo and then purified by silica gel column chromatography, eluting with a mixed solvent of hexane and ethyl acetate (3:2, v/v). The fractions containing the desired product were combined and evaporated in vacuo to obtain ethyl (R)-3-[3,4-bis (dimethylamino)phenyl]-2-hydroxypropionate (0.3 g).

NMR (CDCl$_3$,δ): 1.29 (t,3H),2.65 (s,6H),2.77 (s,6H), 2.75–3.16 (m,2H), 4.23 (q,2H),4.35–4.50 (m,1H),6.70–6.83 (m,2H),7.21–7.26 (m,1H)

EI-MS: 281 [M]$^+$

Preparation 143

To a solution of ethyl (R)-3-[3,4-bis(dimethylamino)phenyl]-2-hydroxypropionate (0.54 g) in benzene were added benzyl alcohol (2 ml) and 13-toluenesulfonic acid (0.8 g) and heated under reflux for 5 hours. The reaction solution was added to aqueous dilute hydrochloric acid, after washing with ethyl acetate, the water layer was neutralized with aqueous saturated sodium bicarbonate, and extracted with ethyl acetate. After washing with saturated sodium chloride, dried over sodium sulfate. After the solvent was evaporated in vacuo, purified by silica gel column chromatography, eluting with a mixed solvent of hexane and ethyl acetate (3:1, v/v). The fractions containing the desired product were combined and evaporated in vacuo to obtain benzyl (12)-3-[3,4-bis(dimethylamino)phenyl]-2-hydroxypropionate (0.3 g).

NMR (CDCl$_3$,δ): 2.74 (s,6H),2.75 (s,6H),2.91 (dd,1H), 3.05 (dd,1H),4.40–4.55 (m,1H),5.15 (d,1H),5.22 (d,1H), 6.60–6.80 (m,3H),7.25–7.40 (m,5H)

IR (KBr): 1734 cm$^{-1}$

Preparation 144

H-D-3,4-DMAPhLac-OBzl (0.32 g) was used instead of H-D-p-Me$_2$NPhLac-OBzl. Except above matter, Boc-MeLeu-D-3,4-DMAPhLac-OBzl (0.59 g) was obtained according to a similar manner to that of Preparation 24.

NMR (CDCl$_3$,δ): 0.89 (d,6H),1.32–1.60 (m,12H), 2.60–2.70 (m,3H),2.75 (s,12H),3.00–3.20 (m,2H),4.62–5.30 (m,4H),6.65–6.78 (m,3H),7.20–7.40 (m,5H)

Preparation 145

Boc-MeLeu-D-3,4-DMAPhLac-OBzl (0.59 g) was used instead of Boc-MeLeu-D-p-Me$_2$NPhLac-OBzl. Except above matter, Boc-MeLeu-D-3,4-DMAPhLac-OH (0.47 g) was obtained according to a similar manner to that of Preparation 25.

NMR (CDCl$_3$,δ): 0.89 (d,6H),1.20–1.80 (m,12H), 2.60–2.85 (m,15H), 3.00–3.28 (m,2H),4.30–4.80 (m) and 5.18–5.37 (m) (2H),6.78–6.90 (m,3H)

Preparation 146

Boc-MeLeu-D-3,4-DMAPhLac-OH (0.47 g) was used instead of Boc-MeLeu-D-p-Me$_2$NPhLac-OH. Except above matter, Boc-MeLeu-D-3,4-DMAPhLac-MeLeu-D-Lac-OBzl (0.67 g) was obtained according to a similar manner to that of
Preparation 26.

NMR (CDCl$_3$,δ): 0.77–1.00 (m,12H),1.38–1.70 (m,18H), 2.71–3.18 (m,20H), 4.60–5.57 (m,6H),6.66–6.80 (m,3H), 7.22–7.38 (m,5H)

Preparation 147

Boc-MeLeu-D-3,4-DMAPhLac-MeLeu-D-Lac-OBzl (0.34 g) was used instead of Boc-MeLeu-D-p-Me$_2$NPhLac-OBzl. Except above matter, Boc-MeLeu-D-3,4-DMAPhLac-MeLeu-D-Lac-OH (0.30 g) was obtained according to a similar manner to that of Preparation 25.

NMR (CDCl$_3$,δ): 0.78–1.08 (m,12H),1.20–1.75 (m,18H), 2.62–3.23 (m,20H), 4.60–5.82 (m,4H),6.72–6.84 (m,3H)

Preparation 148

Boc-MeLeu-D-3,4-DMAPhLac-MeLeu-D-Lac-OBzl (0.33 g) was used instead of Boc-MeLeu-D-p-Me$_2$NPhLac-MeLeu-D-Lac-OBzl. Except above matter, 3HCl.H-MeLeu-D-3,4-DMAPhLac-MeLeu-D-Lac-OBzl (0.30 g) was obtained according to a similar manner to that of Preparation 28.

NMR (CDCl$_3$,δ): 0.76–1.12 (m,12H),1.25–2.20 (m,9H), 2.60–4.20 (m,21H), 5.05–5.60 (m,5H),7.20–7.62 (m,7H), 8.30–8.50 (m,1H),9.42–9.70 (m,1H),10.92–11.20 (m,1H)

Preparation 149

Boc-MeLeu-D-3,4-DMAPhLac-MeLeu-D-Lac-OH (0.30 g) was used instead of Boc-MeLeu-D-p-Me$_2$NPhLac-OH, 3HCl.H-MeLeu-D-3,4-DMAPhLac-MeLeu-D-Lac-OBzl (0.30 g) was used instead of HCl.H-MeLeu-D-Lac-OBzl. Except above matter, Boc-MeLeu-D-3,4-DMAPhLac-MeLeu-D-Lac MeLeu-D-3,4-DMAPhLac-MeLeu-D-Lac-OBzl (0.35 g) was obtained according to a similar manner to that of Preparation 26.

NMR (CDCl$_3$,δ): 0.78–1.00 (m,24H),1.20–1.80 (m,2.7H),2.63–3.18 (m,40H), 4.90–5.60 (m,10H),6.65–6.80 (m,6H),7.22–7.38 (m,5H)

FAB-MS: 1330 [M+H]$^+$

Preparation 150

Boc-MeLeu-D-3,4-DMAPhLac-MeLeu-D-Lac-MeLeu-D-3,4-DMAPhLac-MeLeu-D-m-Lac-OBzl (0.34 g) was used instead of Boc-MeLeu-D-p-Me$_2$NPhLac-OBzl. Except above matter, Boc-MeLeu-D-3,4-DMAPhLac-MeLeu-D-Lac-MeLeu-D-3,4-DMAPhLac-MeLeu-D-Lac-OH (0.35 g) was obtained according to a similar manner to that of Preparation 25.

NMR (CDCl$_3$,δ): 0.78–1.07 (m,24H),1.10–1.80 (m,27H), 2.30–3.20 (m, 40H),4.60–5.74 (m,8H),6.70–6.82 (m,6H)

Preparation 151

(S)-2-fluorophenyl alanine (3.00 g) was dissolved in 6N -aqueous hydrochloric acid (80 ml) and at 0° C. sodium nitrite (3.01 g) was added gradually. After the mixture was stirred for 4 hours successively, the temperature was increased back to room temperature. To the mixture was added sodium nitrite (1.13 g), stirred further for 2 hours, added water (200 ml), and extracted with ether (150 ml×1, 100 ml×2). The ether layer was washed with a solution (saturated brine: water=1:1, v/v) (100 ml×2), dried over calcium chloride, and the solvent was evaporated in vacuo. To the residue, benzene (20 ml), benzylalcohol (1.32 ml) and p-toluenesulfonic acid mono hydrate (0.33 g) were added and heated under reflux for an hour using Dean-stark apparatus. After cooling down to room temperature, the crude product, which was gained by evaporating the solvent, was purified by silica gel chromatography, eluting with a mixed solvent of ethyl acetate and hexane (1:19 V/V). The fractions containing the desired product were combined and evaporated in vacuo to obtain benzyl (S)-2-chloro-3-(2-fluorophenyl)propionate (2.24 g).

NMR (CDCl$_3$,δ): 3.25 (dd,1H),3.40 (dd,1H),4.57 (t,1H), 5.16 (s,2H),6.98– 7.40 (m,9H)

EI-MS: 292 [M]$^+$

Preparation 152

Benzyl (S)-2-chloro-3-(2-fluorophenyl)propionate (0.90 g) was used instead of benzyl (S)-2-chloro-3-(4-methoxyphenyl) propionate. Except above matter, Boc-MeLeu-D-o-FPhLac-OBzl (1.30 g) was obtained according to a similar matter to that of Preparation 2.

NMR (CDCl$_3$,δ): 0.89 (d,6H),1.38–1.63 (m,12H), 2.58–2.70 (m,3H),3.10– 3.38 (m,2H),4.6–4.78 (m) and 5.1–5.38 (m) (4H),6.97–7.42 (m,9H)

FAB-MS: 402 [M-Boc+H]+
Preparation 153
Boc-MeLeu-D-o-FPhLac-OBzl (1.26 g) was used instead of Boc-MeLeu-D-p-Me₂NPhLac-OBzl. Except above matter, Boc-MeLeu-D-o-FPhLac-OH (1.07 g) was obtained according to a similar manner to that of Preparation 25.
NMR (CDCl₃,δ): 0.82–1.02 (m,6H),1.19–1.82 (m,12H), 2.63–2.88 (m,3H), 3.08–3.9 (m,2H),4.26–4.42 (m) and 4.6–4.8 (m) and 5.23–5.44 (m) (2H),6.99–7.4 (m,4H)
Preparation 154
Boc-MeLeu-D-o-FPhLac-OH (1.03 g) was used instead of Boc-MeLeu-D-p-Me₂NPhLac-OH. Except above matter, Boc-MeLeu-D-o-FPhLac-MeLeu-D-Lac-OBzl (1.45 g) was obtained according to a similar manner to that of Preparation 26.
NMR (CDCl₃,δ): 0.80–1.05 (m,12H),1.18–1.83 (m,18H), 2.7–3.2 (m,8H), 4.6–4.8 (m) and 4.88–5.6 (m) (6H), 6.99–7.43 (m,9H)
FAB-MS: 601 [M-Boc+H]+
Preparation 155
Boc-MeLeu-D-o-FPhLac-MeLeu-D-Lac-OBzl (0.70 g) was used instead of Boc-MeLeu-D-p-Me₂NPhLac-OBzl. Except above matter, Boc-MeLeu-D-o-FPhLac-MeLeu-D-Lac-OH (0.57 g) was obtained according to a similar manner to that of
Preparation 25.
NMR (CDCl₃,δ): 0.79–1.03 (m,12H),1.08–1.85 (m,18H), 2.59–3.38 (m,8H), 4.6–4.98 (m) and 5.05–5.6 (m) and 5.83–6.0 (m) (4H),6.99–7.38 (m,4H)
Preparation 156
Boc-MeLeu-D-o-FPhLac-MeLeu-D-Lac-OBzl (0.61 g) was used instead of Boc-MeLeu-D-p-Me₂NPhLac-MeLeu-D-Lac-OBzl. Except above matter, HCl.H-MeLeu-D-o-FPhLac-MeLeu-D-Lac-OBzl (0.53 g) was obtained according to a similar manner to that of Preparation 28.
NMR (CDCl₃,δ): 0.62–1.03 (m,12H),1.2–2.05 (m,9H), 2.58–2.75 (m, 3H),2.98–3.36 (m,5H),3.62–3.82 (m,1H), 5.02–5.38 (m) and 5.46–5.63 (m) (5H),6.99–7.43 (m,9H)
Preparation 157
Boc-MeLeu-D-o-FPhLac-MeLeu-D-Lac-OH (0.55 g) was used instead of Boc-MeLeu-D-p-Me₂NPhLac-OH, and HCl.H-MeLeu-D-o-FPhLac-MeLeu-D-Lac-OBzl (0.51 g) was used instead of HCl.H-MeLeu-D-Lac-OBzl. Except above matter, Boc-MeLeu-D-o-FPhLac-MeLeu-D-Lac-MeLeu-D-o-FPhLac-MeLeu-D-Lac-OBzl (0.97 g) was obtained according to a similar manner to that of Preparation 26.
NMR (CDCl₃, δ): 0.78–1.04 (m,24H),1.10–1.82 (m,27H),2.7–3.23 (m,16H), 4.6–4.8 (m) and 5.02–5.61 (m) (10H),6.98–7.42 (m,13H)
FAB-MS: 1093 [M-Boc+H]+
Preparation 158
Boc-MeLeu-D-o-FPhLac-MeLeu-D-Lac-MeLeu-D-o-FPhLac-MeLeu-D-Lac-OBzl (0.89 g) was used instead of Boc-MeLeu-D-p-Me₂NPhLac-OBzl. Except above matter, Boc-MeLeu-D-o-FPhLac-MeLeu-D-Lac-MeLeu-D-o-FPhLac-MeLeu-D-Lac-OH (0.84 g) was obtained according to a similar manner to that of Preparation 25.
NMR (CDCl₃,δ): 0.78–1.05 (m,24H),1.12–1.82 (m,27H), 2.62–3.29 (m,16H), 4.5–5.87 (m,8H),6.98–7.38 (m,8H)
Preparation 159
(S)-3-fluorophenylaniline (5.20 g) was used instead of (S)-2-fluorophenylaniline. Except above matter, benzyl (S)-2-chloro-3-(3-fluorophenyl) propionate (7.04 g) was obtained according to a similar manner to that of Preparation 151.
NMR (CDCl₃,δ): 3.17 (dd,1H),3.36 (dd,1H)),4.47 (t,1H), 5.17 (s,2H),6.82–7.04 (m,3H),7.18–7.5 (m,6H)

EI-MS: 292 [M]+
Preparation 160
Benzyl (S)-2-chloro-3-(3-fluorophenyl)propionate (1.76 g) was used instead of benzyl (S)-2-chloro-3-(4-methoxyphenyl) propionate. Except above matter, Boc-MeLeu-D-m-FPhLac-OBzl (1.13 g) was obtained according to a similar manner to that of Preparation 2.
NMR (CDCl₃,δ): 0.9 (d,6H),1.39–1.78 (m,12H),2.6–2.77 (m,3H),3.03–3.22 (m,2H),4.63–4.79 (m) and 4.92–5.36 (m) (4H),6.8–7.0 (m,3H), 7.18–7.42 (m,6H)
FAB-MS: 402 [M-Boc+H]+
Preparation 161
Boc-MeLeu-D-m-FPhLac-OBzl (1.11 g) was used instead of Boc-MeLeu-D-p-Me₂NPhLac-OBzl. Except above matter, Boc-MeLeu-D-m-FPhLac-OH (1.00 g) was obtained according to a similar manner to that of Preparation 25.
NMR (CDCl₃,δ): 0.82–1.00 (m,6H),1.2–1.8 (m,12H), 2.76–2.85 (m,3H), 3.02–3.25 (m,2H),4.38–4.5 (m) and 4.62–4.79 (m) and 5.19–5.41 (m) (2H),6.86–7.04 (m,3H), 7.19–7.38 (m,1H)
Preparation 162
Boc-MeLeu-D-m-FPhLac-OH (0.99 g) was used instead of Boc-MeLeu-D-p-Me₂NPhLac-OH. Except above matter, Boc-MeLeu-D-m-FPhLac-MeLeu-D-Lac-OBzl (1.32 g) was obtained according to a similar manner to that of Preparation 26.
NMR (CDCl₃,δ): 0.80–1.01 (m,12H),1.39–1.79 (m,18H), 2.73–3.18 (m,8H), 5.03–5.57 (m,6H),6.88–7.07 (m,3H), 7.21–7.42 (m,6H)
FAB-MS: 601 [M-Boc+H]+
Preparation 163
Boc-MeLeu-D-m-FPhLac-MeLeu-D-Lac-OBzl (0.65 g) was used instead of Boc-MeLeu-D-p-Me₂NPhLac-OBzl. Except above matter, Boc-MeLeu-D-m-FPhLac-MeLeu-D-Lac-OH (0.69 g) was obtained according to a similar manner to that of
Preparation 25.
NMR CCDCl₃,δ): 0.8–1.02 (m,12H),1.1–1.8 (m,18H), 2.63–3.3 (m,8H), 4.62–5.59 (m) and 5.73–5.85 (m) (4H), 6.83–7.1 (m,3H),7.19–7.38 (m,1H)
Preparation 164
Boc-MeLeu-D-m-FPhLac-MeLeu-D-Lac-OBzl (0.65 g) was used instead of Boc-MeLeu-D-p-Me₂NPhLac-MeLeu-D-Lac-OBzl. Except above matter, HCl.H-MeLeu-D-m-FPhLac-MeLeu-D-Lac-OBzl (0.59 g) was obtained according to a similar manner to that of Preparation 28.
NMR (CDCl₃,δ): 0.69–1.03 (m,12H),1.18–2.03 (m,9H), 2.58–2.7 (m,3H), 2.82–3.0 (m,3H),3.03–3.21 (m,2H), 3.62–3.82 (m,1H),5.01–5.38 (m) and 5.41–5.58 (m) (5H), 6.94–7.07 (m,3H),7.17–7.43 (m,6H)
Preparation 165
Boc-MeLeu-D-m-FPhLac-MeLeu-D-Lac-OH (0.69 g) was used instead of Boc-MeLeu-D-p-Me₂NPhLac-OH, HCl.H-MeLeu-D-m-FPhLac-MeLeu-D-Lac-OBzl (0.59 g) was used instead of HCl.H-MeLeu-D-Lac-OBzl. Except above matter, Boc-MeLeu-D-m-FPhLac-MeLeu-D-Lac-MeLeu-D-m-FPhLac-MeLeu-D-Lac-OBzl (1.06 g) was obtained according to a similar manner to that of Preparation 26.
NMR (CDCl₃,δ): 0.77–1.04 (m,24H),1.04–1.95 (m,27H), 2.6–3.3 (m,16H), 4.62–4.79 (m) and 4.88–5.58 (m) (10H), 6.82–7.14 (m,6H),7.19–7.42 (m,7H)
FAB-MS: 1094 [M-Boc+H]+
Preparation 166
Boc-MeLeu-D-m-FPhLac-MeLeu-D-Lac-MeLeu-Do-m-FPhLac-MeLeu-D-Lac-OBzl (0.97 g) was used instead of Boc-MeLeu-D-p-Me₂NPhLac-OBzl. Except above matter, Boc-MeLeu-D-m-FPhLac-MeLeu-D-Lac-MeLeu-D-m-FPhLac-MeLeu-D-Lac-OH (0.81 g) was obtained according to a similar manner to that of Preparation 25.

NMR (CDCl$_3$,δ): 0.77–1.05 (m,24H),1.05–1.83 (m,27H), 2.58–3.22 (m,16H), 4.6–4.79 (m) and 4.88–5.78 (m) (8H) 6.85–7.08 (m,6H),7.18–7.39 (m,2H)

Preparation 167

(S)-4-fluorophenylaniline (5.00 g) was used instead of (S)-2-fluorophenylaniline. Except above matter, benzyl (S)-2-chloro-3-4-fluorophenyl) propionate (1.8 g) was obtained according to similar manner to that of Preparation 151.

NMR (CDCl$_3$,δ): 3.16 (dd,1H),3.33 (dd,1H),4.44 (t,1H), 5.15 (s,2H),6.88–7.42 (m,9H)

EI-MS: 292 [M]$^+$

Preparation 168

Benzyl (S)-2-chloro-3-(4-fluorophenyl)propionate (2.21 g) was used instead of benzyl (S)-2-chloro-3-(4-methoxyphenyl) propionate. Except above matter, Boc-MeLeu-D-p-FPhLac-OBzl (1.55 g) was obtained according to a similar manner to that of Preparation 2.

NMR (CDCl$_3$,δ): 0.9 (d,6H),1.3–1.62 (m,12H),2.58–2.67 (m,3H),3.0–3.12 (m,2H),4.6–4.79 (m) and 4.9–5.27 (m) (4H),6.9–7.42 (m,9H)

FAB-MS: 402 [M-Boc+H]$^+$

Preparation 169

Boc-MeLeu-D-p-FPhLac-OBzl (1.45 g) was used instead of Boc-MeLeu-D-p-Me$_2$NPhLac-OBzl. Except above matter, Boc-MeLeu-D-p-FPhLac-OH (1.25 g) was obtained according to a similar manner to that of Preparation 25.

NMR (CDCl$_3$,δ): 0.83–1.00 (m,6H),1.41–1.78 (m,12H), 2.7–2.84 (m,3H), 3.02–3.23 (m,2H),4.41–5.39 (m,3H), 6.9–7.06 (m,2H),7.1–7.26 (m,2H)

Preparation 170

Boc-MeLeu-D-p-FPhLac-OH (1.23 g) was used instead of Boc-MeLeu-D-p-Me$_2$NPhLac-OH. Except above matter, Boc-MeLeu-D-p-FPhLac-MeLeu-D-Lac-OBzl (2.06 g) was obtained according to a similar manner to that of Preparation 26.

NMR (CDCl$_3$,δ): 0.7–1.04 (m,12H),1.1–1.97 (m,18H), 2.63–2.96 (m,6H), 3.0–3.18 (m,2H),4.6–5.5 (m,6H), 6.88–7.1 (m,2H),7.15–7.5 (m,7H)

FAB-MS: 601 [M-Boc+H]$^+$

Preparation 171

Boc-MeLeu-D-p-FPhLac-MeLeu-D-Lac-OBzl (0.9 g) was used instead of Boc-MeLeu-D-p-Me$_2$NPhLac-OBzl. Except above matter, Boc-MeLeu-D-p-FPhLac-MeLeu-D-Lac-OH (0.78 g) was obtained according to a similar manner to that of
Preparation 25.

NMR (CDCl$_3$,δ): 0.8–1.02 (m,12H),1.05–1.8 (m,18H), 2.62—3.3 (m,8H), 4.6–5.85 (m,4H),6.88–7.05 (m,2H), 7.12–7.28 (m,2H)

Preparation 172

Boc-MeLeu-D-p-FPhLac-MeLeu-D-Lac-OBzl (0.89 g) was used instead of Boc-MeLeu-D-p-Me$_2$NPhLac-MeLeu-D-Lac-OBzl. Except above matter, HCl.H-MeLeu-D-p-FPhLac-MeLeu-D-Lac-OBzl (0.85 g) was obtained according to a similar manner to that of Preparation 28.

NMR (CDCl$_3$,δ): 0.68–1.05 (m,12H),1.18–2.05 (m,9H), 2.53–2.68 (m,3H), 2.82–3.0 (m,3H),3.0–3.18 (m,2H), 3.63–3.81 (m,1H),5.02–5.38 (m,4H), 5.4–5.59 (m,1H), 6.96–7.07 (m,2H),7.15–7.42 (m,7H)

Preparation 173

Boc-MeLeu-D -p-FPhLac-MeLeu-D-Lac-OH (0.77 g) was used instead of Boc-MeLeu-D-p-Me$_2$NPhLac-OH, and HCl.H-MeLeu-D-p-FPhLac-MeLeu-D-Lac-OBzl (0.84 g) was used instead of HCl.H-MeLeu-D-Lac-OBzl. Except above matter, Boc-MeLeu-D-p-FPhLac-MeLeu-D-Lac-MeLeu-D-p-FPhLac-MeLeu-D-Lac-OBzl (1.32 g) was obtained according to a similar manner to that of Preparation 26.

NMR (CDCl$_3$,δ): 0.78–1.07 (m,24H),1.13–1.9 (m,27H), 2.62–3.28 (m,16H), 4.6–4.8 (m) and 4.9–5.57 (m) (10H), 6.86–7.07 (m,4H),7.07–7.42 (m,9H)

FAB-MS: 1094 [M-Boc+H]$^+$

Preparation 174

Boc-MeLeu-D-p-FPhLac-MeLeu-D-Lac-MeLeu-D-p-FPhLac-MeLeu-D-Lac-OBzl (1.31 g) was used instead of Boc-MeLeu-D-p-Me$_2$NPhLac-OBzl. Except above matter, Boc-MeLeu-D-p-FPhLac-MeLeu-D-Lac-MeLeu-D-p-FPhLac-MeLeu-D-Lac-OH (0.99 g) was obtained according to a similar manner to that of Preparation 25.

NMR (CDCl$_3$,δ): 0.79–1.05 (m,24H),1.18–1.93 (m,27H), 2.62–3.24 (m,16H), 4.58–5.8 (m,8H),6.88–7.04 (m,4H), 7.1–7.38 (m,4H)

Preparation 175

Boc-MeLeu-D)-p-MeOPhLac-MeLeu-D-Lac-OH (0.96 g) was used instead of Boc-MeLeu-D-p-Me$_2$NPhLac-OH, and HCl.H-MeLeu-D-PhLac-MeLeu-D-Lac-OBzl (1.42 g) was used instead of, HCl.H-MeLeu-D-Lac-OBzl. Except above matter, Boc-MeLeu-D-p-MeOPhLac-MeLeu-D-Lac-MeLeu-D-PhLac-MeLeu-D-Lac-OBzl (1.28 g) was obtained according to a similar manner to that of Preparation 26.

NMR (CDCl$_3$,δ): 0.77–1.02 (m,24H),1.02–1.96 (m,27H), 2.6–3.25 (m,16H), 3.78 (s,3H),4.6–4.8 (m) and 4.95–5.57 (m) (10H),6.78–6.90 (m,2H), 7.04–7.4 (m,12H)

FAB-MS: 1087 [M-Boc+H]$^+$

Preparation 176

Boc-MeLeu-D-p-MeOPhLac-MeLeu-D-Lac-MeLeu-D-PhLac-MeLeu-D-Lac-OBzl (1.13 g) was used instead of Boc-MeLeu-D-p-Me$_2$NPhLac-OBzl. Except above matter, Boc-MeLeu-D-p-MeOPhLac-MeLeu-D-Lac-MeLeu-D-PhLac-MeLeu-D-Lac-OH (0.98 g)was obtained according to a similar manner to that of Preparation 25.

NMR (CDCl$_3$,δ): 0.72–1.04 (m,24H),1.04–1.9 (m,27H), 2.6–3.25 (m,16H), 3.78 (s,3H),4.58—4.8 (m) and 4.82–5.56 (m) and 5.65–5.82 (m) (8H),6.78–6.9 (m,2H),7.03–7.38 (m,7H)

Preparation 177

Benzyl chloroacetate (1.85 g) was used instead of benzyl (S)- 2-chloro-3-(4-methoxyphenyl)propionate. Except above matter, Boc-MeLeu-Glycol-OBzl (4.0 g) was obtained according to a similar manner to that of Preparation 2.

NMR (CDCl$_3$,δ): 0.93 (d,6H),1.45 (s,9H),1.4–1.8 (m,3H),2.78 (s) and 2.80 (s) (3H),4.6–5.0 (m,3H),5.29 (s,2H),7.35 (s,5H)

IR (KBr): 1740,1695 cm$^{-1}$

Preparation 178

Boc-MeLeu-Glycol-OBzl (1.50 g) was used instead of Boc-MeLeu-D-p-Me$_2$NPhLac-MeLeu-D-Lac-OBzl. Except above matter, HCl.H-MeLeu-Glycol-OBzl (1.32 g) was obtained according to a similar manner to that of Preparation 28.

IR (KBr): 1753 cm$^{-1}$

Preparation 179

Boc-MeLeu-D-p-MeOPhLac-OH (0.69 g) was used instead of Boc-MeLeu-D-p-Me$_2$NPhLac-OH, and HCl.H-MeLeu-Glycol-OBzl (0.59 g) was used instead of HCl.H-MeLeu-D-Lac-OBzl. Except above matter, Boc-MeLeu-D-p-MeOPhLac-MeLeu-Glycol-OBzl (0.79 g) was obtained according to a similar manner to that of Preparation 26.

NMR (CDCl$_3$,δ): 0.8–1.0 (m,12H),1.2–1.8 (m,6H),1.42 (s) and 1.47 (s) (9H),2.7–3.0 (m,6H),3.03 (d,2H),3.78

(s,3H),4.66 (s,2H),4.6–5.5 (m, 3H),5.28 (s,2H),6.82 (d,2H), 7.14 (d,2H),7.3–7.4 (m,5H)

IR (KBr): 1740,1694,1664 cm$^{-1}$

APCI-MS: 599 [M+H]$^+$

Preparation 180

Boc-MeLeu-D-p-MeOPhLac-MeLeu-Glycol-OBzl (0.39 g) was used instead of Boc-MeLeu-D-p-Me$_2$NPhLac-OBzl. Except above matter, Boc-MeLeu-D-p-MeOPhLac-MeLeu-Glycol-OH (0.32 g) was obtained according to a similar manner to that of Preparation 25.

IR (KBr): 1744,1691,1663 cm$^{-1}$

Preparation 181

Boc-MeLeu-D-p-MeOPhLac-MeLeu-Glycol-OBzl (0.39 g) was used instead of Boc-MeLeu-D-p-Me$_2$NPhLac-MeLeu-D-Lac-OBzl. Except above matter, HCl.H-MeLeu-D-p-MeOPhLac-MeLeu-Glycol-OBzl (0.38 g) was obtained according to a similar manner to that of Preparation 28.

IR (KBr): 1745,1653 cm$^{-1}$

Preparation 182

Boc-MeLeu-D-p-MeOPhLac-MeLeu-Glycol-OH (0.32 g) was used instead of Boc-MeLeu-D-p-Me$_2$NPhLac-OH, and HCl.H-MeLeu-D-p-MeOPhLac-MeLeu-Glycol-OBzl (0.37 g) was used instead of HCl.H-MeLeu-D-Lac-OBzl. Except above matter, Boc-MeLeu-D-p-MeOPhLac-MeLeu-Glycol-MeLeu-D-p-MeOPhLac-MeLeu-Glycol-OBzl (0.603 g) was obtained according to a similar manner to that of Preparation 26.

NMR (CDCl$_3$,δ): 0.8–1.05 (m,24H),1.41 (s) and 1.47 (s) (9H),1.21–1.9 (m,12H),2.65–3.1 (m,16H),3.78 (s,6H), 4.60–4.85 (m) and 5.15– 5.5 (m) (10H),5.16 (s,2H), 6.75–6.90 (m,2H),7.05–7.2 (m,2H),7.3–7.4 (m,5H)

IR (KBr): 1744,1689,1667 cm$^{-1}$

FAB-MS: 1189M+H]$^+$

Preparation 183

Boc-MeLeu-D-p-MeOPhLac-MeLeu-Glycol-MeLeu-D-p-MeOPhLac-MeLeu-Glycol-OBzl (0.58 g) was used instead of Boc-MeLeu-D-p-Me$_2$NPhLac-OBzl. Except above matter, Boc-MeLeu-D-p-MeOPhLac-MeLeu-Glycol-MeLeu-D-p-MeOPhLac-MeLeu-Glycol-OH (0.55 g) was obtained according to a similar manner to that of Preparation 25.

IR (KBr): 1742, 1664cm$^{-1}$

Preparation 184

Boc-MeLeu-D-p-MeOPhLac-MeLeu-Glycol-MeLeu-D-p-MeOPhLac-MeLeu-Glycol-OH (0.55 g) was used instead of Boc-MeLeu-D-p-Me$_2$NPhLac-MeLeu-D-Lac-OBzl. Except above matter, HCl.H-MeLeu-D-p-MeOPhLac-MeLeu-Glycol-MeLeu-D-p-MeOPhLac-MeLeu-Glycol-OH (0.53 g) was obtained according to a similar manner to that of Preparation 28.

IR (KBr): 1741,1646 cm$^{-1}$

EXAMPLE 1

To a solution of Boc-MeLeu-D-p-MeOPhLac-MeLeu-D-Lac-MeLeu-D-p-MeOPhLac-MeLeu-D-Lac-OC$_6$F$_5$ (0.4 g) in methylene chloride (4 ml) was added under ice-cooling, trifluoroacetic acid (2 ml) and stirred for 2 hours successively. The solvent was evaporated in vacuo, and the residue was dissolved in dioxane (30 ml). After adding the mixture dropwise for 5 hours into pyridine (629 ml) which was heated at 90° C., it was stirred for 2 and ½ hours successively. The solvent was evaporated in vacuo, azeotroped by toluene (30 ml). To the residue was added ethyl acetate (200 ml), washed with 10% aqueous citric acid solution, water, aqueous saturated sodium bicarbonate solution, water in order, dried over anhydrous sodium sulfate, and concentrated in vacuo. The resultant crude product was purified by silica gel chromatography, and eluted with mixture of ethyl acetate and hexane (1.5:1, v/v). The fractions containing the desired product were combined and evaporated in vacuo to obtain

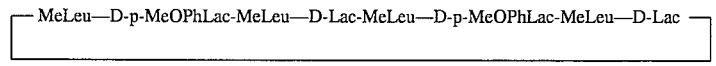

(0.16 g).

NMR (CDCl$_3$,δ): 0.79–1.00 (m,24H), 1.10–1.80 (m,18H), 2.73–3.09 (m,16H), 3.78 (s,6H), 4.40–4.54 (m), and 5.00–5.67 (m) (8H), 6.82 (d, 4H), 7.15 (d,4H).

IR (KBr): 1741,1662 cm$^{-1}$

FAB-MS: 1009 (M+H)$^+$

EXAMPLE 2

Boc-MeLeu-D-Man-MeLeu-D-Lac-MeLeu-D-Man-MeLeu-D-Lac-OC$_6$F$_5$ was used instead of Boc-MeLeu-D-p-MeOPhLac-MeLeu-D-Lac-MeLeu-D-p-MeOPhLac-MeLeu-D-Lac-OC$_6$F$_5$. Except above matter,

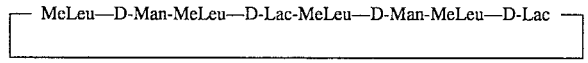

(0.11 g) was obtained according to a similar manner to that of Example 1.

NMR (CDCl$_3$,δ): 0.70–1.00 (m,24H), 1.10–1.98 (m,18H), 2.75–3.10 (m,12H),4.60–5.70 (m,6H), 6.44 (s,2H),7.30–7.60 (m,10H).

IR (KBr): 1750,1677 cm$^{-1}$,

FAB-MS: 921 (M+H)$^+$

EXAMPLE 3

To a solution of 3HCl.H-MeLeu-D-p-Me$_2$NPhLac-MeLeu-D-Lac-MeLeu-D-p-Me$_2$NPhLac-MeLeu-D-Lac-OH (0.825 g) in dichloromethane was (700 ml) was added under ice-cooling, triethylamine (0.45 ml) and bis(2-oxo-3-oxazolidinyl) phosphinic chloride (0.27 g), and stirred for 14 hours successively, and further stirred for 4 hours at room temperature. The solvent was evaporated in vacuo, was added water (50 ml), and extracted with ethyl acetate (40 ml×3). The ethyl acetate layer was washed with saturated brine, dried over anhydrous sodium sulfate. The solvent was evaporated in vacuo, the resultant crude product was purified by silica gel chromatography, and eluted with mixture of hexane, ethyl acetate and ethanol (60:35:5, v/v). The fractions containing the desired product were combined and evaporated in vacuo to obtain ⌐ MeLeu—D-p-Me₂NPhLac-MeLeu—D-Lac-MeLeu—D-p-Me₂NPLac-MeLeu—D-Lac ⌐
                                                                    ⌐

(0.40 g).
NMR (CDCl₃,δ) 0.75–1.1 (m,24H),1.4–1.85 (m,18H), 2.7–3.1 (m,28H), 4.4–5.8 (m,8H),6.64 (d,4H),7.08 (d,4H)
IR (KBr): 1741,1662 cm⁻¹
FAB-MS: 1035 [M+H]⁺

EXAMPLE 4

⌐ MeLeu—D-p-Me₂NPhLac-MeLeu—D-Lac-MeLeu—D-p-Me₂NPhLac-MeLeu—D-Lac ⌐
                                                                    ⌐

(0.145 g)
was dissolved in 4N-hydrogen chloride in ethyl acetate (2 ml).
The solvent was evaporated in vacuo, the residue was dissolved in 4N-hydrogen chloride in ethyl acetate (2 ml) again. After the solvent was evaporated in vacuo, azeotroped by toluene (10 ml) twice to give ⌐ MeLeu—D-p-Me₂NPhLac-MeLeu—D-Lac-MeLeu—D-p-Me₂NPhLac-MeLeu—D-Lac ⌐ 2HCl
                                                                    ⌐

(0.157 g).
NMR (CDCl₃,δ) 0.7–1.1 (m,24H),1.25–1.85 (m,18H), 2.8–3.4 (m,16H), 3.15 (bs,12H),4.6–5.75 (m,8H),7.35–7.5 (m,4H),7.6–7.75 (m,4H)
IR (KBr): 1742,1649 cm⁻¹

EXAMPLE 5

To a solution of 3HCl·H-MeLeu-D-p-MorPhLac-MeLeu-D-Lac-MeLeu-D-p-MorPhLac-MeLeu-D-Lac-OH (0.404 g) in dichloromethane (162 ml) were added sodium bicarbonate (0.27 g) and bis(2-oxo-3-oxazolidinyl) phosphinic chloride (0.13 g), and stirred for 71 hours successively. The solvent was evaporated in vacuo, added water (50 ml), and extracted with ethyl acetate (50ml×3). The ethyl acetate layer was washed with saturated brine, dried over anhydrous sodium sulfate. The solvent was evaporated in vacuo, the resultant crude product was purified by silica gel chromatography, and eluted with mixture of hexane, ethyl acetate, and ethanol (50:45:5, v/v). The fractions containing the desired product were combined and evaporated in vacuo to obtain ⌐ MeLeu—D-p-MorPhLac-Meleu—D-Lac-MeLeu—D-p-MorPhLac-MeLeu-D-Lac ⌐
                                                                    ⌐

(0.238 g).

NMR (CDCl$_3$,δ) 0.8–1.1 (m,24H),1.3–1.8 (m,18H), 2.7–3.2 (m,24H), 3.8–3.9 (m,8H),44–4.55 (m) and 5.0–5.7 (m) (8H),6.82 (d,4H),7.13 (d, 4H)

IR (KBr): 1740, 1662 cm$^{-1}$

FAB-MS : 1119 [M+H$^+$

EXAMPLE 6

3HCl.H-MeLeu-D-p-PyrPhLac-MeLeu-D-Lac-MeLeu-D-p-PyrPhLac-MeLeu-D-Lac-OH (0.80 g) was used instead of 3HCl.H-MeLeu-D-p-MorPhLac-MeLeu-D-Lac-MeLeu-D-p-MorPhLac-MeLeu-D-Lac-OH. Except above matter, ⌐ MeLeu—D-p-PyrPhLac-MeLeu—D-Lac-MeLeu—D-p-PyrPhLac-MeLeu—D-Lac ⌐
└                                                                  ┘

(0.238 g) was obtained according to a similar manner to that of

EXAMPLE 5.

NMR (CDCl$_3$,δ) 0.75–1.1 (m,24H),1.2–1.8 (m,18H), 1.9–2.05 (m,8H), 2.7–3.1 (m,16H),3.15–3.3 (m,8H), 4.4–4.55 (m) and 5.0–5.7 (m) (8H), 6.46 (d,4H),7.06 (d,4H)

IR (KBr): 1740,1664 cm$^{-1}$

FAB-MS: 1087 [M+H]$^+$

EXAMPLE 7

⌐ MeLeu—D—PhLac-MeLeu—D-Lac-MeLeu—D—PhLac-MeLeu—D-Lac⌐
└                                                      ┘

(0.382 g) was cooled down to −10° C. After fuming nitric acid (3.5 ml) was added dropwise in 15 minutes, the mixture was stirred for one hour at room temperature. The reaction solution was added gradually into saturated sodium bicarbonate (25 ml), and extracted with ethyl acetate (25 ml×3). After washing the ethyl acetate layer with saturated brine, dried over anhydrous sodium sulfate, and the solvent was evaporated in vacuo to give crude product of ⌐ MeLeu—D-p-NO$_2$PhLac-MeLeu—D-Lac-MeLeu—D-p-NO$_2$PhLac-MeLeu—D-Lac ⌐
└                                                                       ┘

(0.465 g).

NMR (CDCl$_3$; δ) 0.65–1.1 (m,24H),1.2–1.8 (m,18H), 2.7–3.3 (m,16H), 44–4.55 (m) and 5.0–5.7 (m) (8H), 7.35–7.55 (m,4H),8.05–8.15 (m, 4H)

IR (KBr): 1742,1662,1519,1343 cm$^{-1}$

FAB-MS: 1039 [M+H]$^+$

EXAMPLE 8

To a ethanol (5 ml) solution of crude product (72 mg) of

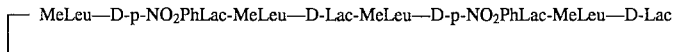

were added 37% aqueous formaldehyde (0.4 ml) and 10% palladium on carbon (0.1 g), and hydrogenated for 2 hours at room temperature under hydrogen gas atmospheric pressure. The catalyst was filtered off and the crude product which was gained by evaporating the solvent was purified by silica gel column chromatography, eluting with a mixed solvent of hexane, ethyl acetate and ethanol (75:20:5, v/v). The fractions containing the desired product were combined and evaporated in vacuo to obtain

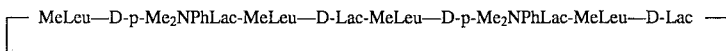

(42 mg).

NMR (CDCl$_3$; δ) 0.75–1.1 (m,24H),1.4–1.85 (m,18H), 2.7–3.1 (m,28H), 4.4–5.8 (m,8H),6.64 (d,4H),7.08 (d,4H)
IR (KBr): 1741,1662 cm$^{-1}$

EXAMPLE 9

To a methanol (10 ml) solution of crude product (312 mg) of

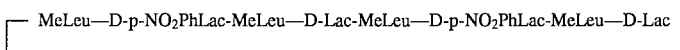

was added 10% palladium on carbon (0.1 g), and hydrogenated for 2 hours at room temperature under hydrogen gas atmospheric pressure. The catalyst was filtered off and the crude product which was gained by evaporating the solvent was purified by silica gel column chromatography, eluting with a mixed solvent of hexane, ethyl acetate and ethanol (40:55:5, v/v). The fractions containing the desired product were combined and evaporated in vacuo to obtain

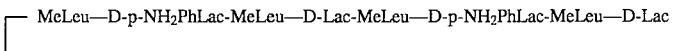

(144 mg).

NMR (CDCl$_3$,δ): 0.75–1.1 (m,24H),1.4–1.85 (m,18H), 2.7–3.1 (m, 16H),4.4–5.8 (m,8H),6.64 (d,4H),7.08 (d,4H)
IR (KBr): 1741,1662 cm$^{-1}$
FAB-MS: 979 [M+H]$^+$

EXAMPLE 10

To a methanol (10 ml) solution of

┌─ MeLeu—D-p-NH₂PhLac-MeLeu—D-Lac-MeLeu—D-p-NH₂PhLac-MeLeu—D-Lac ─┐
└─────────────────────────────────────────────────────────────────┘

(250 mg) were added acetaldehyde (0.56 g) and 10% palladium on carbon (0.15 g), and hydrogenated for 4 hours at room temperature under hydrogen gas atmospheric pressure. The catalyst was filtered off and the crude product which was gained by evaporating the solvent was purified by silica gel column chromatography, eluting with a mixed solvent of hexane, ethyl acetate, and ethanol (25:20:5, v/v). The fractions containing the desired product were combined and evaporated in vacuo to obtain ┌─ MeLeu—D-p-Et₂NPhLac-MeLeu—D-Lac-MeLeu—D-p-Et₂NPhLac-MeLeu—D-Lac ─┐
└───────────────────────────────────────────────────────────────────┘

(147 mg).
NMR (CDCl₃,δ): 0.7–1.9 (m,54H),2.65–3.1 (m,12H), 3.2–3.4 (m,8H), 4.4–4.5 (m) and 5.0–5.8 (m) (8H),6.45–6.6 (m,4H),7.0–7.1 (m,4H)
IR (KBr):1741,1662 cm⁻¹
FAB-MS: 1091 [M+H]⁺

EXAMPLE 11

To a methanol (10 ml) solution of

┌─ MeLeu—D-p-NH₂PhLac-MeLeu—D-Lac-MeLeu—D-p-NH₂PhLac-MeLeu—D-Lac ─┐
└─────────────────────────────────────────────────────────────────┘

(250 mg) were added n-hexanal (0.62 g) and 10% palladium on carbon (0.15 g), and hydrogenated for 11 hours at room temperature under hydrogen gas atmospheric pressure. The catalyst was filtered off and the crude product which was gained by evaporating the solvent was purified by silica gel column chromatography, eluting with a mixed solvent of hexane, ethyl acetate, and ethanol (25:70:5, v/v). The fractions containing the desired product were combined and evaporated in vacuo. To the resultant residue was added 4N-hydrogen chloride in ethyl acetate (5 ml), and the solvent was evaporated, repeated the same procedure again to give ┌─ MeLeu—D-p-Hex₂NPhLac-MeLeu—D-Lac-MeLeu—D-p-Hex₂NPhLac-MeLeu—D-Lac ─┐ 2HCl
└─────────────────────────────────────────────────────────────────────┘

(147 mg).
NMR (CDCl₃,δ): 0.7–2.1 (m,86H),2.7–3.6 (m,24H), 4.4–4.6 (m) and 5.0–5.7 (m) (8H),7.3–7.45 (m,4H),7.6–7.75 (m,4H)
IR (KBr): 1743,1656 cm⁻¹
FAB-MS: 1315 [M+H]⁺

EXAMPLE 12

3HCl.H-MeLeu-D-p-PipPhLac-MeLeu-D-Lac-MeLeu-D-p-PipPhLac-MeLeu-D-Lac-OH (1.24 g) was used instead of 3HCl.H-MeLeu-D-p-MorPhLac-MeLeu-D-Lac-MeLeu-D-p-MorPhLac-MeLeu-D-Lac-OH. Except above matter,

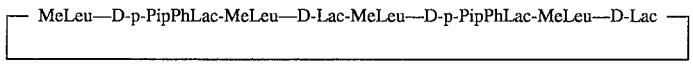

(0.82 g) was obtained according to a similar manner to that of Example 5.

NMR (CDCl$_3$,δ): 0.7–1.1 (m,24H),1.2–1.9 (m,30H), 2.65–3.2 (m,24H), 4.4–4.55 (m) and 5.0–5.7 (m) (8H),6.84 (d,4H),7.09 (d,4H)

IR (KBr): 1740,1663 cm$^{-1}$
FAB-MS: 1115 [M+H]$^+$

EXAMPLE 13

A suspension of
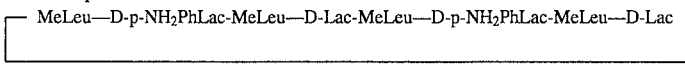

(0.228 g),2,5-dimethoxytetrahydrofuran (0.045 ml) and acetic acid (1 ml) were stirred for 3 hours at room temperature, and further stirred for 3 hours at 50° C. Further more, to the mixture was added 2,5-dimethoxytetrahydrofuran (0.045 ml) and stirred for 3 hours successively. The reaction solution was poured into ice-aqueous saturated sodium bicarbonate solution and extracted with ethyl acetate (20 ml×2). After washing the ethyl acetate layer with saturated brine, dried over anhydrous sodium sulfate, the crude product which was gained by evaporating the solvent was purified by silica gel column chromatography, eluting with a mixed solvent of hexane, ethyl acetate, and ethanol (50:45:5, v/v). The fractions containing the desired product were combined and evaporated in vacuo to obtain

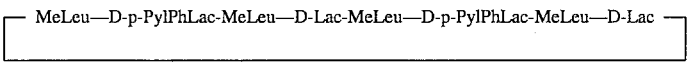

(56.6 mg).

NMR (CDCl$_3$,δ): 0.77–1.1 (m,24H),1.2–1.82 (m,18H), 2.7–3.23 (m, 16H),52–5.73 (m,8H),6.28–6.39 (m,4H), 6.56–6.7 (m,4H),6.96–7.38 (m, 8H)

IR (KBr): 1742,1663 cm$^{-1}$
FAB-MS: 1079 [M+H]$^+$

EXAMPLE 14

To a trifluoroacetic acid (0.5 ml) solution of

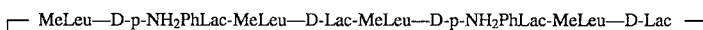

(48 mg) was added at room temperature, sodium nitrite (8 mg), after the reaction solution was stirred for 1 hour at 60° C., the solvent was evaporated in vacuo and the residue was azeotroped by toluene. To the residue were added sodium bicarbonate (84 mg), water (0.5 ml), dioxane (2.5 ml) and after the mixture was stirred for 15 hours at room temperature, water (50 ml) was added and extracted with ethyl acetate (25 ml×3). After washing the ethyl acetate layer with saturated brine, dried over anhydrous sodium sulfate, the crude product which was gained by evaporating the solvent was purified by silica gel column chromatography, eluting with a mixed solvent of hexane, ethyl acetate, and ethanol (65:30:5, v/v). The fractions containing the desired product were combined and evaporated in vacuo to obtain ┌─ MeLeu—D-p-OHPhLac-MeLeu—D-Lac-MeLeu—D-p-OHPhLac-MeLeu—D-Lac ─┐
└                                                                ┘

(40.4 mg).

NMR (CDCl$_3$,δ): 0.70–1.8 (m,42H),2.7–3.15 (m,16H), 4.38–4.55 (m) and 4.97–5.68 (m) (8H),6.65–6.83 (m,4H), 6.94–7.17 (m,4H)

IR (KBr): 1741,1648 cm$^{-1}$
FAB-MS: 981 [M+H]$^+$

EXAMPLE 15

A suspension of

┌─ MeLeu—D-p-OHPhLac-MeLeu—D-Lac-MeLeu—D-p-OHPhLac-MeLeu—D-Lac ─┐
└                                                                ┘

(0.3 g), dimethylformamide (2 ml), potassium carbonate (128.5 mg) and ethyl iodide (0.08 ml) were stirred for 18 hours at room temperature, and then water (30 ml) was added and extracted with ethyl acetate (20 ml×3). After washing the ethyl acetate layer with saturated brine, dried over anhydrous sodium sulfate, the crude product which was gained by evaporating the solvent was purified by silica gel column chromatography, eluting with a mixed solvent of hexane and ethyl acetate (1:1, v/v). The fractions containing the desired product were combined and evaporated in vacuo to obtain ┌─ MeLeu—D-p-EtOPhLac-MeLeu—D-Lac-MeLeu—D-p-EtOPhLac-MeLeu—D-Lac ─┐
└                                                                  ┘

(0.188 g).

NMR (CDCl$_3$,δ): 0.76–1.09 (m,24H),1.3–1.82 (m,16H), 2.7–3.15 (m, 16H),3.99 (q,4H),4.4–4.58 (m) and 4.9–5.8 (m) (8H),6.76–6.88 (m,4H), 7.07–7.39 (m,4H)

IR (KBr): 1743,1664 cm$^{-1}$
FAB-MS: 1037 [M+H]$^+$

EXAMPLE 16 n-Hexyl bromide (0.25 ml) was used instead of ethyl iodide. Except above matter, ┌─ MeLeu—D-p-HexOPhLac-MeLeu—D-Lac-MeLeu—D-p-HexOPhLac-MeLeu—D-Lac ─┐
└                                                                    ┘

(0,179 g) was obtained according to a similar manner to that of Example 15.

NMR (CDCl$_3$,δ): 0.70–1.9 (m,64H),2.68–3.2 (m,16H), 3.91 (t,4H),4.42–4.56 (m) and 5.03–5.9 (m) (8H),6.69–6.84 (m,4H),7.05–7.2 (m,4H)

IR (KBr): 1742,1661 cm$^{-1}$
FAB-MS: 1149 [M+H]$^+$

EXAMPLE 17

To Boc-MeLeu-D-p-MEPhLac-MeLeu-D-Lac-MeLeu-D-p-MEPhLac-MeLeu-D-Lac-OH (1.03 g) was added 4N-hydrogen chloride in ethyl acetate solution (20 ml), and stirred for 50 minutes at 0° C. After the solvent was evaporated in vacuo, the residue was azeotroped by toluene, was added dichloromethane (850 ml), cooled down to 0° C., added triethylamine (0.47 ml) and bis (2-oxo-3-oxazolidinyl) phosphinic chloride (0.32 g), and stirred for 14 hours successively. The solvent was evaporated in vacuo, was added 5% citric acid (100 ml) and extracted with ethyl acetate (100 ml×2). After washing the ethyl acetate layer with aqueous saturated sodium bicarbonate and saturated brine, dried over anhydrous sodium sulfate, the crude product which was gained by evaporating the solvent was purified by silica gel column chromatography, eluting with a mixed solvent of hexane, ethyl acetate, and ethanol (60:35:5, v/v). The fractions containing the desired product were combined and evaporated in vacuo to obtain ⌐ MeLeu—D-p-MEPhLac-MeLeu—D-Lac-MeLeu—D-p-MEPhLac-MeLeu—D-Lac ⌐
⌊_____⌋

(0.506 g).
NMR (CDCl$_3$,δ): 0.78–1.08 (m,24H),1.2–1.9 (m,18H), 2.62–3.09 (m, 16H),3.45 (s,6H),3.65–3.82 (m,4H), 4.02–4.19 (m,4H),4.6–4.78 (m) and 5.01–5.7 (m) (8H), 6.8–6.96 (m,4H),7.12–7.22 (m,4H)
IR (KBr): 1740,1662 cm$^{-1}$
FAB-MS: 1097 [M+H]$^+$

EXAMPLE 18

A suspension of

⌐ MeLeu—D-p-OHPhLac-MeLeu—D-Lac-MeLeu—D-p-OHPhLac-MeLeu—D-Lac ⌐
⌊_____⌋

(0.3 g), dimethylformamide (2 ml), potassium carbonate (128.5 mg),1-bromo- 2-(2-methoxyethoxy)ethane (0.93 ml), and sodium iodide (92.9 mg) were stirred for 17 hours at room temperature and stirred for 24 hours at 50° C. Further, to the mixture was added sodium iodide (92.9 mg) and stirred for 8 hours successively. To the mixture was added water (30 ml) and extracted with ether (20 ml×3). After washing the ether layer with saturated brine, dried over anhydrous sodium sulfate, the crude product which was gained by evaporating the solvent was purified by silica gel column chromatography and eluting with a mixed solvent of hexane, ethyl acetate, and ethanol (30:65:5, v/v). The fractions containing the desired product were combined and evaporated in vacuo to obtain ⌐ MeLeu—D-p-MEEPhLac-MeLeu—D-Lac-MeLeu—D-p-MEEPhLac-MeLeu—D-Lac ⌐
⌊_____⌋

(0.105 g).
NMR (CDCl$_3$,δ): 0.71–1.82 (m,54H),2.84–3.23 (m,16H), 3.39 (s,6H), 3.59–3.63 (m,4H),3.63–3.79 (m,4H),3.79–3.92 (m,4H),4.03–4.2 (m,4H), 4.39–4.56 (m) and 5.0–5.77 (m) (8H),6.83 (d,4H),7.13 (d,4H)
IR (KBr): 1743,1662 cm$^{-1}$
FAB-MS: 1185 [M+H]$^+$

EXAMPLE 19

Boc-MeLeu-D-o-MeOPhLac-MeLeu-D-Lac-MeLeu-D-o-MeOPhLac-MeLeu-D-Lac-OH (1.24 g) was used instead of Boc-MeLeu-D-p-MEPhLac-MeLeu-D-Lac-MeLeu-D-p-MEPhLac-MeLeu-D-Lac-OH. Except above matter, ⌐ MeLeu—D-o-MeOPhLac-MeLeu—D-Lac-MeLeu—D-o-MeOPhLac-MeLeu—D-Lac ⌐
⌊_____⌋

(0.87 g) was obtained according to a similar manner to that of EXAMPLE 17.

NMR (CDCl$_3$,δ): 0.79–1.08 (m,24H),1.20–1.81 (m,18H), 2.71–3.15 (m, 16H),3.85 (s) and 3.86 (s) (6H),4.40–5.89 (m,8H),6.82–6.93 (m,4H),7.12–7.27 (m,4H)

IR (KBr):1741,1663cm$^{-1}$

FAB-MS: 1009 [M+H]$^+$

EXAMPLE 20

Boc-MeLeu-D-m-MeOPhLac-MeLeu-D-Lac-MeLeu-D-m-MeOPhLac-MeLeu-D-Lac-OH (0.79 g) was used instead of Boc-MeLeu-D-p-MEPhLac-MeLeu-D-Lac-MeLeu-D-p-MEPhLac-MeLeu-D-Lac-OH. Except above matter, ⎡—MeLeu—D-m-MeOPhLac-MeLeu—D-Lac-MeLeu—D—m-MeOPhLac-MeLeu—D-Lac—⎤

(0.51 g) was obtained according to a similar manner to that of Example 17.

NMR (CDCl$_3$,δ): 0.75–1.15 (m,24H),1.20–1.85 (m,18H), 2.70–3.18 (m, 16H),3.78 (s,6H),4.40–5.78 (m,8H), 6.70–6.88 (m,6H),7.10–7.25 (m,2H)

IR (KBr):1739,1661cm$^{-1}$

FAB-MS: 1009M+H]$^+$

EXAMPLE 21

Boc-MeLeu-D-3,4-DMOPhLac-MeLeu-D-Lac-MeLeu-D- 3,4-DMOPhLac-MeLeu-D-Lac-OH (0.26 g) was used instead of Boc-MeLeu-D-p-MEPhLac-MeLeu-D-Lac-MeLeu-D-p-MEPhLac-MeLeu-D-Lac-OH. Except above matter, ⎡— MeLeu—D-3,4-DMOPhLac-MeLeu—D-Lac-MeLeu—D-3,4-DMO—PhLac-MeLeu—D-Lac —⎤

(0.14 g) was obtained according to a similar manner to that of EXAMPLE 17.

NMR (CDCl$_3$,δ): 0.72–1.00 (m,24H),1.21–1.80 (m,18H), 2.72–3.15 (m, 16H),3.85 (s,6H),3.86 (s,6H),4.42–5.72 (m,8H),6.72–6.81 (m,6H)

IR (KBr): 1740,1661 cm$^{-1}$

FAB-MS: 1069 [M+H]$^+$

EXAMPLE 22

Boc-MeLeu-D-2,4-DMOPhLac-MeLeu-D-Lac-MeLeu-D- 2,4-DMOPhLac-MeLeu-D-Lac-OH (1.49 g) was used instead of Boc-MeLeu-D-p-MEPhLac-MeLeu-D-Lac-MeLeu-D-p-MEPhLac-MeLeu-D-Lac-OH. Except above matter, ⎡— MeLeu—D-2,4-DMOPhLac-MeLeu—D-Lac-MeLeu—D-2,4-DMO—PhLac-MeLeu—D-Lac —⎤

(0.95 g) was obtained according to a similar manner to that of Example 17.

NMR (CDCl$_3$,δ): 0.78–1.12 (m,24H),1.20–1.80 (m,18H), 2.70–3.16 (m, 16H),3.75–3.90 (m,12H),4.40–5.83 (m,8H), 6.35–6.43 (m,4H),7.01–7.12 (m,2H)

IR (KBr): 1740,1661 cm$^{-1}$

FAB-MS: 1069 [M+H]$^+$

EXAMPLE 23

Boc-MeLeu-D-3,4-MODPhLac-MeLeu-D-Lac-MeLeu-D-3,4-MODPhLac-MeLeu-D-Lac-OH (0.59 g) was used instead of Boc-MeLeu-D-p-MEPhLac-MeLeu-D-Lac-MeLeu-D-p-MEPhLac-MeLeu-D-Lac-OH. Except above matter, ⎡— MeLeu—D-3,4-MODPhLac-MeLeu—D-Lac-MeLeu—D-3,4-MODPhLac-MeLeu—D-Lac —⎤

(0.29 g) was obtained according to a similar manner to that of Example 17.

NMR (CDCl$_3$,δ): 0.80–1.12 (m,24H),1.22–2.00 (m,18H), 2.63–3.20 (m, 16H),4.35–4.53 (m) and 5.00–5.70 (m) (8H), 5.82–6.00 (m,4H),6.60–6.82 (m,6H)

IR (KBr):1740,1661 cm$^{-1}$
FAB-MS: 1037 [M+H]$^+$

EXAMPLE 24

3HCl.H-MeLeu-D-3MA-4MOPhLac-MeLeu-D-Lac-MeLeu-D- 3MA-4MOPhLac-MeLeu-D-Lac-OH (1.18 g) was used instead of 3HCl.H-MeLeu-D-p-MorPhLac-MeLeu-D-Lac-MeLeu-D-p-MorPhLac-MeLeu-D-Lac-OH. Except above matter, ┌─ MeLeu—D-3MA-4MOPhLac-MeLeu—D-Lac-MeLeu—D-3MA-4MOPhLac-MeLeu—D-Lac ─┐
└──────────────────────────────────────────────────────────────────────┘

(0.390 g) was obtained according to a similar manner to that of Example 5.

NMR (CDCl$_3$,δ): 0.75–1.1 (m,24H),1.2–2.1 (m,18H), 2.6–3.3 (m,28H), 3.85 (s,6H),4.4–4.55 (m) and 5.0–5.7 (m) (8H),67–6.9 (m,6H)

IR (KBr):1741,1663 cm$^{-1}$
FAB-MS: 1095 [M+H]$^+$

EXAMPLE 25

Boc-MeLeu-D-3,4-DMAPhLac-MeLeu-D-Lac-MeLeu-D- 3,4-DMAPhLac-MeLeu-D-Lac-OH (0.35 g) was used instead of Boc-MeLeu-D-p-MEPhLac-MeLeu-D-Lac-MeLeu-D-p-MEPhLac-MeLeu-D-Lac-OH, and N-methylmorpholine (0.186 ml) was used instead of triethylamine. Except above matter, ┌─ MeLeu—D-3,4-DMAPhLac-MeLeu—D-Lac-MeLeu—D-3,4-DMAPhLac-MeLeu—D-Lac ─┐
└──────────────────────────────────────────────────────────────────────┘

(0.19 g) was obtained according to a similar manner to that of Example 17.

NMR (CDCl$_3$,δ): 0.70–1.10 (m,24H),1.15–1.90 (m,18H), 2.68–3.20 (m,40H),4.39–4.60 (m) and 4.95–5.75 (m) (8H), 6.65–6.80 (m,6H)

IR (KBr):1739,1662 cm$^{-1}$
FAB-MS: 1121 [M+H]$^+$

EXAMPLE 26

Boc-MeLeu-D-o-FPhLac-MeLeu-D-Lac-MeLeu-D-o-FPhLac-MeLeu-D-Lac-OH (0.82 g) was used instead of Boc-MeLeu-D-p-MEPhLac-MeLeu-D-Lac-MeLeu-D-p-MEPhLac-MeLeu-D-Lac-OH. Except above matter, ┌─ MeLeu—D-o-FPhLac-MeLeu—D-Lac-MeLeu—D-o-FPhLac-MeLeu—D-Lac ─┐
└──────────────────────────────────────────────────────────────┘

(0.58 g) was obtained according to a similar manner to that of Example 17.
NMR (CDCl$_3$,δ): 0.64–1.13 (m,24H),1.21–1.83 (m,18H), 2.63–3.22 (m,16H),4.4–4.57 (m) and 5.02–5.82 (m) (8H), 6.98–7.38 (m,8H)
IR (KBr): 1743,1663 cm$^{-1}$
FAB-MS: 985 [M+H]$^+$

EXAMPLE 27

Boc-MeLeu-D-m-FPhLac-MeLeu-D-Lac-MeLeu-D-m-FPhLac-MeLeu-D-Lac-OH (0.77 g) was used instead of Boc-MeLeu-D-p-MEPhLac-MeLeu-D-Lac-MeLeu-D-p-MEPhLac-MeLeu-D-Lac-OH. Except above matter, ⎡— MeLeu—D-m-FPhLac-MeLeu—D-Lac-MeLeu—D-m-FPhLac-MeLeu—D-Lac —⎤

(0.534 g) was obtained according to a similar manner to that of Example 17.
NMR (CDCl$_3$,δ): 0.7–1.06 (m,24H),1.1–1.95 (m,18H), 2.6–3.27 (m,16H),4.4–4.58 (m) and 5.0–5.78 (m) (8H), 6.82–7.1 (m,6H),7.18–7.38 (m,2H)
IR (KBr): 1741,1663 cm$^{-1}$
FAB-MS: 985 [M+H]$^+$

EXAMPLE 28

Boc-MeLeu-D-p-FPhLac-MeLeu-D-Lac-MeLeu-D-p-FPhLac-MeLeu-D-Lac-OH (0.99 g) was used instead of Boc-MeLeu-D-p-MEPhLac-MeLeu-D-Lac-MeLeu-D-p-MEPhLac-MeLeu-D-Lac-OH. Except above matter, ⎡— MeLeu—D-p-FPhLac-MeLeu—D-Lac-MeLeu—D-p-FPhLac-MeLeu—D-Lac—⎤

(0.686 g) was obtained according to a similar manner to that of Example 17.
NMR (CDCl$_3$,δ): 0.7–1.1 (m,24H),1.18–1.9 (m,18H), 2.62–3.23 (m,16H),4.4–4.58 (m) and 5.0–5.75 (m) (8H), 6.89–7.07 (m,4H),7.07–7.25 (m,4H)
IR (KBr): 1741,1662 cm$^{-1}$
FAB-MS: 985 [M+H]$^+$

EXAMPLE 29

Boc-MeLeu-D-p-MeOPhLac-MeLeu-D-Lac-MeLeu-D-PhLac-MeLeu-D-Lac-OH (0.96 g) was used instead of Boc-MeLeu-D-p-MEPhLac-MeLeu-D-Lac-MeLeu-D-p-MEPhLac-MeLeu-D-Lac-OH. Except above matter, ⎡— MeLeu—D-p-MeOPhLac-MeLeu—D-Lac-MeLeu—D-PhLac-MeLeu—D-Lac —⎤

(0.461 g) was obtained according to a similar manner to that of Example 17.
NMR (CDCl$_3$,δ): 0.78–1.06 (m,24H),1.3–1.82 (m,18H), 2.64–3.21 (m,16H),3.78 (s,3H),4.6–4.78 (m) and 5.02–5.8 (m) (8H),6.78–6.93 (m,2H),7.1–7.4 (m,7H)
IR (KBr): 1741,1663 cm$^{-1}$
FAB-MS: 979 [M+H]$^+$

EXAMPLE 30

HCl.H-MeLeu-D-p-MeOPhLac-MeLeu-Glycol-MeLeu-D-p-MeOPhLac-MeLeu-Glycol-OH (0.52 g) was used instead of HCl.H-MeLeu-D-p-MorPhLac-MeLeu-D-Lac-MeLeu-D-p-MorPhLac-MeLeu-D-Lac-OH. Except above matter, ⎡— MeLeu—D-p-MeOPhLac-MeLeu-Glycol-MeLeu—D-MeOPhLac- MeLeu-Glycol —⎤

(0.26 g) was obtained according to a similar manner to that of Example 5.
NMR (CDCl$_3$,δ): 0.75–1.1 (m,24H),1.2–1.8 (m,12H), 2.7–3.2 (m,16H), 3.78 (s,3H),3.79 (s,3H),42–5.8 (m,10H), 6.75–6.9 (m,4H),7.05–7.2 (m,4H)
IR (KBr): 1741,1663 cm$^{-1}$
FAB-MS: 981 [M+H]$^+$

EXAMPLE 31

To an aqueous suspension (5 ml) of oxydiacetaldehyde bis(diethylacetal) (0.50 g) was added five drops of acetic acid and heated for half an hour at 100° C. To the resultant oxydiacetaldehyde solution was added acetonitrile solution (5 ml) of ⎡ MeLeu—D-p-NH₂PhLac-MeLeu—D-Lac-MeLeu—D-p-NH₂PhLac-MeLeu—D-Lac ⎤

(0.198 g) and after stirring for half an hour at room temperature, adjusted to pH7.0 by aqueous saturated sodium bicarbonate solution. To the mixture was added sodium cyanoborohydride (0.055 g) and pH was kept under 7.5 with acetic acid and in the meanwhile, it was stirred for 2 hours at room temperature. To the resultant reaction solution was added water (50 ml) and aqueous saturated sodium bicarbonate solution (5 ml), and extracted with ethyl acetate. After washing the ethyl acetate layer with saturated brine, dried over anhydrous sodium sulfate. The solvent was evaporated in vacuo, the resultant crude product was purified by silica gel chromatography, and eluted with mixture of hexane, ethyl acetate, and ethanol (55:40:5, v/v). The fractions containing the desired product were combined and evaporated in vacuo to obtain ⎡ MeLeu—D-p-MorPhLac-MeLeu—D-Lac-MeLeu—D-p-MorPhLac-MeLeu—D-Lac ⎤

(0.045 g).

NMR (CDCl₃,δ): 0.8–1.1 (m,24H),1.3–1.8 (m,18H), 2.7–3.2 (m,24H), 3.8–3.9 (m,8H),4.4–4.55 (m) and 5.0–5.7 (m) (8H),6.82 (d,4H),7.13 (d, 4H)

IR (KBr): 1740,1662 cm⁻¹

FAB-MS: 1119 [M+H]⁺

What we claim is:

1. A compound of the general formula (I):

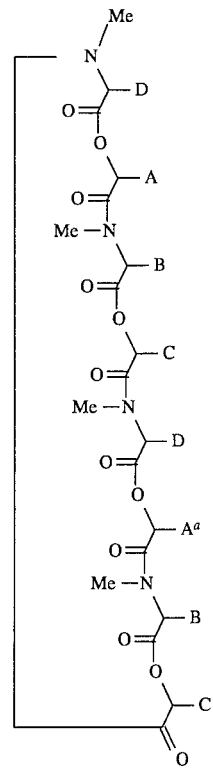

wherein

A is a substituted benzyl group or a phenyl group which may have substituent(s), Aᵃ is a benzyl group which may have substituent(s) or a phenyl group which may have substituent(s), B and D are each lower alkyl, and C is hydrogen or lower alkyl, or a pharmaceutically acceptable salt thereof.

2. A compound of claim 1, wherein A and $A^a$ are each a benzyl group substituted by cyclic amino, dilower alkylamino or lower alkoxy, B and D are each isopropyl, and C is methyl.

3. A compound of claim 1, wherein A and $A^a$ are each a benzyl group substituted by morpholino, dimethylamino or methoxy.

4. A compound of claim 1, wherein A and $A^a$ are each a benzyl group substituted by amino, nitro or hydroxy, B and D are each isopropyl, and C is methyl.

5. A compound of the formula:

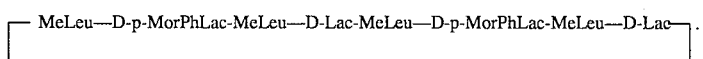

6. A compound of the formula:

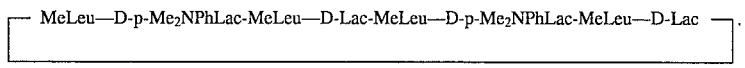

7. A process for preparation of a compound of the general formula:

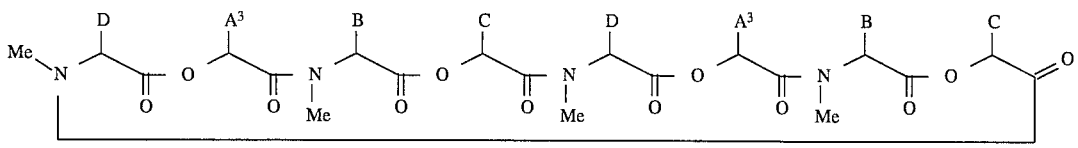

or a salt thereof, which comprises subjecting a compound of the general formula:

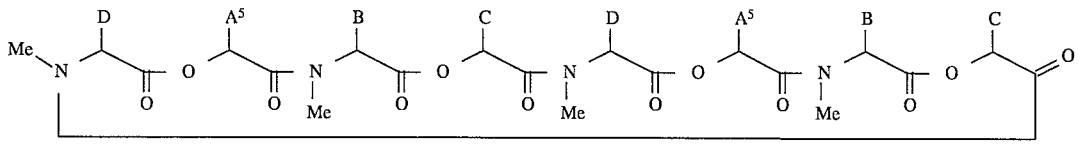

or a salt thereof, to a monoalkylation reaction followed by an intramolecular reaction, wherein B and D are each lower alkyl, C is hydrogen or lower alkyl, $A^3$ is a benzyl group substituted by amino, or a benzyl group substituted by amino and lower alkoxy, and $A^5$ is a benzyl group substituted by cyclic amino, or a benzyl group substituted by cyclic amino and lower alkoxy.

8. A process for preparation of a compound of the general formula:

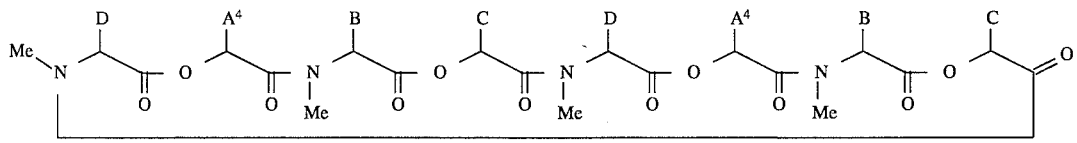

or a salt thereof, which comprises
subjecting a compound of the general formula:

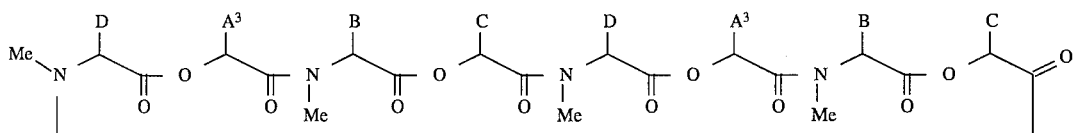

or a salt thereof, to an alkylation reaction,
wherein B and D are each lower alkyl,
C is hydrogen or lower alkyl,
$A^3$ is a benzyl group substituted by amino, or a benzyl group substituted by amino and lower alkoxy, and
$A^4$ is a benzyl group substituted by mono- or di-lower alkylamino, or a benzyl group substituted by mono- or di-lower alkylamino and lower alkoxy.

9. An anthelmintic agent which comprises a compound or a pharmaceutically acceptable salt thereof of claim 1 as an active ingredient.

10. The compound of claim 1 wherein B and D are each an isobutyl group.

11. The compound of claim 1 wherein A and $A^a$ are each a benzyl group substituted by a para-methoxy group.

12. The process of claim 7 wherein B and D are each an isobutyl group.

* * * * *